US005460949A

United States Patent [19]

Saunders et al.

[11] Patent Number: 5,460,949

[45] Date of Patent: Oct. 24, 1995

[54] METHOD AND COMPOSITION FOR INCREASING THE ACCUMULATION OF SQUALENE AND SPECIFIC STEROLS IN YEAST

[75] Inventors: Court A. Saunders, Clarendon Hills; Fred R. Wolf, Naperville; Indrani Mukharji, Evanston, all of Ill.

[73] Assignee: Amoco Corporation, Naperville, Ill.

[21] Appl. No.: 783,861

[22] Filed: Oct. 28, 1991

Related U.S. Application Data

[63] Continuation-in-part of Ser. No. 613,380, Nov. 15, 1990, abandoned.

[51] Int. Cl.[6] .............................. C12N 9/02; C12N 15/53; C12P 33/00; C12P 33/16

[52] U.S. Cl. .............................. 435/55; 435/52; 435/189; 435/254.21; 435/320.1; 536/23.2

[58] Field of Search .......................... 435/52, 69.1, 172.3, 435/189, 190, 255, 256, 320.1, 55, 254.21; 935/28, 42, 43; 514/183; 536/23.2

OTHER PUBLICATIONS

Bard, M. et al. *Lipids* 12:645–655 (1977).
Basson, M. E. et al. *Mol. and Cell. Biol.* 8(9):3797–3808 (1988).
Serrouse, M. et al. *Biochem. J.* 240:541–547 (1986).
Gil, G. et al. *Cell* 41:249–258 (1985).
Kunkel et al, *Proc. Natl. Acad. Sci.,* USA, 82:4778–4782 (1985).
Avruch et al., *Can. J. Biochem,* 54:657–665 (1976).
Basson et al., *Proc. Natl. Acad. Sci.,* USA, 83:5563–5567, (1986).
Boeke et al., *Science,* 239:280–282 (1988).
Stinchcomb, *Nature,* 282:39–43 (1979).
Ito et al., *Journal of Bacteriology,* 152:163–168 (1983).
Boeke et al., *Mol. Gen. Genet* 197:345–346 (1984).
Holm et al., *Gene,* 42:169–173 (1986).
Woods et al., *Microbis,* 10:73–80 (1974).
Parks et al., *CRC Critical Reviews in Microbiology* :301–341 (1978).
Liscum et al., *The Journal of Biological Chemistry,* 260:522–530 (1985).
Johnston et al., *Proc. Natl. Acad. Sci.,* 79:6791–6975, (1982).
Chin et al., *Nature,* 308:613–617 (1984).
Odell et al., *Nature,* 313 (1985).
Rine et al., *Proc. Natl. Acad. Sci.,* 80:6750–6754 (1983).
Brown et al., Journal of Lipid Research, 21:505–517 (1980).
Caberera et al., J. Biol. Chem., 261(8):3578–3583 (1986).
Hasumi et al., Eur. J. Biochem, 164:547–552 (1987).
Jordan–Stark et al., J. of Biol. Chem., 264:17919–17923 (1989).
Orci et al., Cell, 36:835–845 (1984).
Chin et al., Proc. Natl. Acad. Sci., USA 79:1185–1189 (1982).
Goldstein et al., Nature, 343:425–430 (1990).
Luskey, K. L. Molecular and Cellular Biology, 7(5):1881–1893 (1987).
Benfey et al., Science, 244:174 (1989).
Toriyama et al., Biotechnology, 6:1072 (1988).

*Primary Examiner*—Robert A. Wax
*Assistant Examiner*—Dian Jacobson
*Attorney, Agent, or Firm*—Norval B. Galloway

[57] ABSTRACT

A method of increasing the accumulation of squalene and specific sterols in yeast comprising increasing the expression level of a structural gene encoding a polypeptide having HMG-CoA reductase activity in a mutant yeast having single or double defects in the expression of sterol biosynthetic enzymes is provided. The expression level of a structural gene is preferably increased by transforming yeast with a recombinant DNA molecule comprising a vector operatively linked to an exogenous DNA segment that encodes a polypeptide having HMG-CoA reductase activity and a promoter that is suitable for driving the expression of the encoded polypeptide in the transformed yeast. The polypeptide having HMG-CoA reductase activity is preferably a truncated, active HMG-CoA reductase enzyme. Recombinant DNA molecules useful for transforming yeast and mutant yeast transformed with such recombinant DNA molecules are also disclosed.

30 Claims, 20 Drawing Sheets

```
TTTATTAACT TATTTTTTTC TTCTTTCTAC CCAATTCTAG TCAGGAAAAG ACTAAGGGCT   60

GGAACATAGT GTATCATTGT CTAATTGTTG ATACAAAGTA GATAAATACA TAAAACAAGC  120

ATG CCG CCG CTA TTC AAG GGA CTG AAA CAG ATG GCA AAG CCA ATT GCC    168
Met Pro Pro Leu Phe Lys Gly Leu Lys Gln Met Ala Lys Pro Ile Ala
  1               5                  10                  15

TAT GTT TCA AGA TTT TCG GCG AAA CGA CCA ATT CAT ATA ATA CTT TTT    216
Tyr Val Ser Arg Phe Ser Ala Lys Arg Pro Ile His Ile Ile Leu Phe
             20                  25                  30

TCT CTA ATC ATA TCC GCA TTC GCT TAT CTA TCC GTC ATT CAG TAT TAC    264
Ser Leu Ile Ile Ser Ala Phe Ala Tyr Leu Ser Val Ile Gln Tyr Tyr
         35                  40                  45

TTC AAT GGT TGG CAA CTA GAT TCA AAT AGT GTT TTT GAA ACT GCT CCA    312
Phe Asn Gly Trp Gln Leu Asp Ser Asn Ser Val Phe Glu Thr Ala Pro
     50                  55                  60

AAT AAA GAC TCC AAC ACT CTA TTT CAA GAA TGT TCC CAT TAC TAC AGA    360
Asn Lys Asp Ser Asn Thr Leu Phe Gln Glu Cys Ser His Tyr Tyr Arg
 65                  70                  75                  80
```

FIGURE 2-1

```
GAT TCC TCT CTA GAT GGT TGG GTA TCA ATC ACC GCG CAT GAA GCT AGT      408
Asp Ser Ser Leu Asp Gly Trp Val Ser Ile Thr Ala His Glu Ala Ser
                 85                  90                  95

GAG TTA CCA GCC CCA CAC CAT TAC TAT CTA TTA AAC CTG AAC TTC AAT      456
Glu Leu Pro Ala Pro His His Tyr Tyr Leu Leu Asn Leu Asn Phe Asn
            100                 105                 110

AGT CCT AAT GAA ACT GAC TCC ATT CCA GAA CTA GCT AAC ACG GTT TTT      504
Ser Pro Asn Glu Thr Asp Ser Ile Pro Glu Leu Ala Asn Thr Val Phe
        115                 120                 125

GAG AAA GAT AAT ACA AAA TAT ATT CTG CAA GAA GAT CTC AGT GTT TCC      552
Glu Lys Asp Asn Thr Lys Tyr Ile Leu Gln Glu Asp Leu Ser Val Ser
    130                 135                 140

AAA GAA ATT TCT TCT ACT GAT GGA ACG AAA TGG AGG TTA AGA AGT GAC      600
Lys Glu Ile Ser Ser Thr Asp Gly Thr Lys Trp Arg Leu Arg Ser Asp
145                 150                 155                 160

AGA AAA AGT CTT TTC GAC GTA AAG ACG TTA GCA TAT TCT CTC TAC GAT      648
Arg Lys Ser Leu Phe Asp Val Lys Thr Leu Ala Tyr Ser Leu Tyr Asp
                165                 170                 175
```

FIGURE 2-2

```
GTA TTT TCA GAA AAT GTA ACC CAA GCA GAC CCG TTT GAC GTC CTT ATT     696
Val Phe Ser Glu Asn Val Thr Gln Ala Asp Pro Phe Asp Val Leu Ile
            180                 185                 190

ATG GTT ACT GCC TAC CTA ATG ATG TTC TAC ACC ATA TTC GGC CTC TTC     744
Met Val Thr Ala Tyr Leu Met Met Phe Tyr Thr Ile Phe Gly Leu Phe
        195                 200                 205

AAT GAC ATG AGG AAG ACC GGG TCA AAT TTT TGG TTG AGC GCC TCT ACA     792
Asn Asp Met Arg Lys Thr Gly Ser Asn Phe Trp Leu Ser Ala Ser Thr
    210                 215                 220

GTG GTC AAT TCT GCA TCA TCA CTT TTC TTA GCA TTG TAT GTC ACC CAA     840
Val Val Asn Ser Ala Ser Ser Leu Phe Leu Ala Leu Tyr Val Thr Gln
225                 230                 235                 240

TGT ATT CTA GGC AAA GAA GTT TCC GCA TTA ACT CTT TTT GAA GGT TTG     888
Cys Ile Leu Gly Lys Glu Val Ser Ala Leu Thr Leu Phe Glu Gly Leu
                245                 250                 255

CCT TTC ATT GTA GTT GTT GTT GGT TTC AAG CAC AAA ATC AAG ATT GCC     936
Pro Phe Ile Val Val Val Val Gly Phe Lys His Lys Ile Lys Ile Ala
            260                 265                 270
```

FIGURE 2-3

```
CAG TAT GCC CTG GAG AAA TTT GAA AGA GTC GGT TTA TCT AAA AGG ATT     984
Gln Tyr Ala Leu Glu Lys Phe Glu Arg Val Gly Leu Ser Lys Arg Ile
        275                 280                 285

ACT ACC GAT GAA ATC GTT TTT GAA TCC GTG AGC GAA GAG GGT GGT CGT    1032
Thr Thr Asp Glu Ile Val Phe Glu Ser Val Ser Glu Glu Gly Gly Arg
    290                 295                 300

TTG ATT CAA GAC CAT TTG CTT TGT ATT TTT GCC TTT ATC GGA TGC TCT    1080
Leu Ile Gln Asp His Leu Leu Cys Ile Phe Ala Phe Ile Gly Cys Ser
305                 310                 315                 320

ATG TAT GCT CAC CAA TTG AAG ACT TTG ACA AAC TTC TGC ATA TTA TCA    1128
Met Tyr Ala His Gln Leu Lys Thr Leu Thr Asn Phe Cys Ile Leu Ser
                325                 330                 335

GCA TTT ATC CTA ATT TTT GAA TTG ATT TTA ACT CCT ACA TTT TAT TCT    1176
Ala Phe Ile Leu Ile Phe Glu Leu Ile Leu Thr Pro Thr Phe Tyr Ser
            340                 345                 350

GCT ATC TTA GCG CTT AGA CTG GAA ATG AAT GTT ATC CAC AGA TCT ACT    1224
Ala Ile Leu Ala Leu Arg Leu Glu Met Asn Val Ile His Arg Ser Thr
        355                 360                 365
```

FIGURE 2-4

```
ATT ATC AAG CAA ACA TTA GAA GAA GAC GGT GTT GTT CCA TCT ACA GCA     1272
Ile Ile Lys Gln Thr Leu Glu Glu Asp Gly Val Val Pro Ser Thr Ala
    370                 375                 380

AGA ATC ATT TCT AAA GCA GAA AAG AAA TCC GTA TCT TCT TTC TTA AAT     1320
Arg Ile Ile Ser Lys Ala Glu Lys Lys Ser Val Ser Ser Phe Leu Asn
385                 390                 395                 400

CTC AGT GTG GTT GTC ATT ATC ATG AAA CTC TCT GTC ATA CTG TTG TTT     1368
Leu Ser Val Val Val Ile Ile Met Lys Leu Ser Val Ile Leu Leu Phe
                405                 410                 415

GTT TTC ATC AAC TTT TAT AAC TTT GGT GCA AAT TGG GTC AAT GAT GCC     1416
Val Phe Ile Asn Phe Tyr Asn Phe Gly Ala Asn Trp Val Asn Asp Ala
            420                 425                 430

TTC AAT TCA TTG TAC TTC GAT AAG GAA CGT GTT TCT CTA CCA GAT TTT     1464
Phe Asn Ser Leu Tyr Phe Asp Lys Glu Arg Val Ser Leu Pro Asp Phe
        435                 440                 445

ATT ACC TCG AAT GCC TCT GAA AAC TTT AAA GAG CAA GCT ATT GTT AGT     1512
Ile Thr Ser Asn Ala Ser Glu Asn Phe Lys Glu Gln Ala Ile Val Ser
    450                 455                 460
```

FIGURE 2-5

```
GTC ACC CCA TTA TTA TAT TAC AAA CCC ATT AAG TCC TAC CAA CGC ATT    1560
Val Thr Pro Leu Leu Tyr Tyr Lys Pro Ile Lys Ser Tyr Gln Arg Ile
465                 470                 475                 480

GAG GAT ATG GTT CTT CTA TTG CTT CGT AAT GTC AGT GTT GCC ATT CGT    1608
Glu Asp Met Val Leu Leu Leu Leu Arg Asn Val Ser Val Ala Ile Arg
                485                 490                 495

GAT AGG TTC GTC AGT AAA TTA GTT CTT TCC GCC TTA GTA TGC AGT GCT    1656
Asp Arg Phe Val Ser Lys Leu Val Leu Ser Ala Leu Val Cys Ser Ala
            500                 505                 510

GTC ATC AAT GTG TAT TTA TTG AAT GCT GCT AGA ATT CAT ACC AGT TAT    1704
Val Ile Asn Val Tyr Leu Leu Asn Ala Ala Arg Ile His Thr Ser Tyr
        515                 520                 525

ACT GCA GAC CAA TTG GTG AAA ACT GAA GTC ACC AAG AAG TCT TTT ACT    1752
Thr Ala Asp Gln Leu Val Lys Thr Glu Val Thr Lys Lys Ser Phe Thr
    530                 535                 540

GCT CCT GTA CAA AAG GCT TCT ACA CCA GTT TTA ACC AAT AAA ACA GTC    1800
Ala Pro Val Gln Lys Ala Ser Thr Pro Val Leu Thr Asn Lys Thr Val
545                 550                 555                 560
```

FIGURE 2-6

```
ATT TCT GGA TCG AAA GTC AAA AGT TTA TCA TCT GCG CAA TCG AGC TCA      1848
Ile Ser Gly Ser Lys Val Lys Ser Leu Ser Ser Ala Gln Ser Ser Ser
                565                 570                 575

TCA GGA CCT TCA TCA TCT AGT GAG GAA GAT GAT TCC CGC GAT ATT GAA      1896
Ser Gly Pro Ser Ser Ser Ser Glu Glu Asp Asp Ser Arg Asp Ile Glu
            580                 585                 590

AGC TTG GAT AAG AAA ATA CGT CCT TTA GAA GAA TTA GAA GCA TTA TTA      1944
Ser Leu Asp Lys Lys Ile Arg Pro Leu Glu Glu Leu Glu Ala Leu Leu
        595                 600                 605

AGT AGT GGA AAT ACA AAA CAA TTG AAG AAC AAA GAG GTC GCT GCC TTG      1992
Ser Ser Gly Asn Thr Lys Gln Leu Lys Asn Lys Glu Val Ala Ala Leu
    610                 615                 620

GTT ATT CAC GGT AAG TTA CCT TTG TAC GCT TTG GAG AAA AAA TTA GGT      2040
Val Ile His Gly Lys Leu Pro Leu Tyr Ala Leu Glu Lys Lys Leu Gly
625                 630                 635                 640

GAT ACT ACG AGA GCG GTT GCG GTA CGT AGG AAG GCT CTT TCA ATT TTG      2088
Asp Thr Thr Arg Ala Val Ala Val Arg Arg Lys Ala Leu Ser Ile Leu
                645                 650                 655
```

FIGURE 2-7

```
GCA GAA GCT CCT GTA TTA GCA TCT GAT CGT TTA CCA TAT AAA AAT TAT    2136
Ala Glu Ala Pro Val Leu Ala Ser Asp Arg Leu Pro Tyr Lys Asn Tyr
            660                 665                 670

GAC TAC GAC CGC GTA TTT GGC GCT TGT TGT GAA AAT GTT ATA GGT TAC    2184
Asp Tyr Asp Arg Val Phe Gly Ala Cys Cys Glu Asn Val Ile Gly Tyr
        675                 680                 685

ATG CCT TTG CCC GTT GGT GTT ATA GGC CCC TTG GTT ATC GAT GGT ACA    2232
Met Pro Leu Pro Val Gly Val Ile Gly Pro Leu Val Ile Asp Gly Thr
    690                 695                 700

TCT TAT CAT ATA CCA ATG GCA ACT ACA GAG GGT TGT TTG GTA GCT TCT    2280
Ser Tyr His Ile Pro Met Ala Thr Thr Glu Gly Cys Leu Val Ala Ser
705                 710                 715                 720

GCC ATG CGT GGC TGT AAG GCA ATC AAT GCT GGC GGT GGT GCA ACA ACT    2328
Ala Met Arg Gly Cys Lys Ala Ile Asn Ala Gly Gly Gly Ala Thr Thr
                725                 730                 735

GTT TTA ACT AAG GAT GGT ATG ACA AGA GGC CCA GTA GTC CGT TTC CCA    2376
Val Leu Thr Lys Asp Gly Met Thr Arg Gly Pro Val Val Arg Phe Pro
            740                 745                 750
```

FIGURE 2-8

```
ACT TTG AAA AGA TCT GGT GCC TGT AAG ATA TGG TTA GAC TCA GAA GAG      2424
Thr Leu Lys Arg Ser Gly Ala Cys Lys Ile Trp Leu Asp Ser Glu Glu
        755                 760                 765

GGA CAA AAC GCA ATT AAA AAA GCT TTT AAC TCT ACA TCA AGA TTT GCA      2472
Gly Gln Asn Ala Ile Lys Lys Ala Phe Asn Ser Thr Ser Arg Phe Ala
    770                 775                 780

CGT CTG CAA CAT ATT CAA ACT TGT CTA GCA GGA GAT TTA CTC TTC ATG      2520
Arg Leu Gln His Ile Gln Thr Cys Leu Ala Gly Asp Leu Leu Phe Met
785                 790                 795                 800

AGA TTT AGA ACA ACT ACT GGT GAC GCA ATG GGT ATG AAT ATG ATT TCT      2568
Arg Phe Arg Thr Thr Thr Gly Asp Ala Met Gly Met Asn Met Ile Ser
                805                 810                 815

AAA GGT GTC GAA TAC TCA TTA AAG CAA ATG GTA GAA GAG TAT GGC TGG      2616
Lys Gly Val Glu Tyr Ser Leu Lys Gln Met Val Glu Glu Tyr Gly Trp
            820                 825                 830

GAA GAT ATG GAG GTT GTC TCC GTT TCT GGT AAC TAC TGT ACC GAC AAA      2664
Glu Asp Met Glu Val Val Ser Val Ser Gly Asn Tyr Cys Thr Asp Lys
        835                 840                 845
```

FIGURE 2-9

```
AAA CCA GCT GCC ATC AAC TGG ATC GAA GGT CGT GGT AAG AGT GTC GTC     2712
Lys Pro Ala Ala Ile Asn Trp Ile Glu Gly Arg Gly Lys Ser Val Val
    850                 855                 860

GCA GAA GCT ACT ATT CCT GGT GAT GTT GTC AGA AAA GTG TTA AAA AGT     2760
Ala Glu Ala Thr Ile Pro Gly Asp Val Val Arg Lys Val Leu Lys Ser
865                 870                 875                 880

GAT GTT TCC GCA TTG GTT GAG TTG AAC ATT GCT AAG AAT TTG GTT GGA     2808
Asp Val Ser Ala Leu Val Glu Leu Asn Ile Ala Lys Asn Leu Val Gly
                885                 890                 895

TCT GCA ATG GCT GGG TCT GTT GGT GGA TTT AAC GCA CAT GCA GCT AAT     2856
Ser Ala Met Ala Gly Ser Val Gly Gly Phe Asn Ala His Ala Ala Asn
            900                 905                 910

TTA GTG ACA GCT GTT TTC TTG GCA TTA GGA CAA GAT CCT GCA CAA AAT     2904
Leu Val Thr Ala Val Phe Leu Ala Leu Gly Gln Asp Pro Ala Gln Asn
        915                 920                 925

GTT GAA AGT TCC AAC TGT ATA ACA TTG ATG AAA GAA GTG GAC GGT GAT     2952
Val Glu Ser Ser Asn Cys Ile Thr Leu Met Lys Glu Val Asp Gly Asp
    930                 935                 940
```

FIGURE 2-10

```
TTG AGA ATT TCC GTA TCC ATG CCA TCC ATC GAA GTA GGT ACC ATC GGT      3000
Leu Arg Ile Ser Val Ser Met Pro Ser Ile Glu Val Gly Thr Ile Gly
945                 950                 955                 960

GGT GGT ACT GTT CTA GAA CCA CAA GGT GCC ATG TTG GAC TTA TTA GGT      3048
Gly Gly Thr Val Leu Glu Pro Gln Gly Ala Met Leu Asp Leu Leu Gly
                965                 970                 975

GTA AGA GGC CCG CAT GCT ACC GCT CCT GGT ACC AAC GCA CGT CAA TTA      3096
Val Arg Gly Pro His Ala Thr Ala Pro Gly Thr Asn Ala Arg Gln Leu
            980                 985                 990

GCA AGA ATA GTT GCC TGT GCC GTC TTG GCA GGT GAA TTA TCC TTA TGT      3144
Ala Arg Ile Val Ala Cys Ala Val Leu Ala Gly Glu Leu Ser Leu Cys
        995                 1000                1005

GCT GCC CTA GCA GCC GGC CAT TTG GTT CAA AGT CAT ATG ACC CAC AAC      3192
Ala Ala Leu Ala Ala Gly His Leu Val Gln Ser His Met Thr His Asn
    1010                1015                1020

AGG AAA CCT GCT GAA CCA ACA AAA CCT AAC AAT TTG GAC GCC ACT GAT      3240
Arg Lys Pro Ala Glu Pro Thr Lys Pro Asn Asn Leu Asp Ala Thr Asp
1025                1030                1035                1040
```

FIGURE 2-11

```
ATA AAT CGT TTG AAA GAT GGG TCC GTC ACC TGC ATT AAA TCC         3282
Ile Asn Arg Leu Lys Asp Gly Ser Val Thr Cys Ile Lys Ser
                1045                1050

TAAACTTAGT CATACGTCAT TGGTATTCTC TTGAAAAAGA AGCACAACAG CACCATGTGT  3342

TACGTAAAAT ATTTACTT                                              3360
```

FIGURE 2-12

METHOD AND COMPOSITION FOR INCREASING THE ACCUMULATION OF SQUALENE AND SPECIFIC STEROLS IN YEAST

DESCRIPTION

CROSS -REFERENCE TO RELATED APPLICATION

This application is a continuation-in-part application of application Ser. No. 07/613,380, filed Nov. 15, 1990, now abandoned.

TECHNICAL FIELD

The present invention relates to a method and composition for increasing the accumulation of squalene and specific sterols in yeast. Squalene and sterol accumulation is increased by increasing the expression level of a gene encoding a polypeptide having HMG-CoA reductase activity.

BACKGROUND OF THE INVENTION

As used herein, the term "sterol" refers to derivatives of a fused, reduced ring system, cyclopenta[α] -phenanthrene, comprising three fused cyclohexane rings (A, B and C) in a phenanthrene arrangement, and a terminal cyclopentane ring (D) having the formula and carbon atom position numbering shown below:

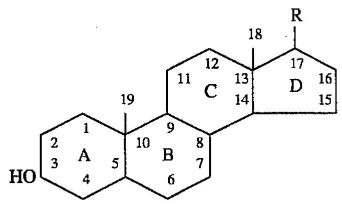

where R is an 8 to 10 carbon-atom sidechain.

Sterols are metabolically derived from acetate. Acetyl coenzyme A (CoA) reacts with acetoacetyl CoA to form 3-hydroxy-3-methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through the sequential steps of isomerization, condensation and dehydrogenation, IPP is converted to geranyl pyrophosphate (GPP). GPP combines with IPP to form farnesyl pyrophosphate (FPP), two molecules of which are reductively condensed to form squalene, a 30-carbon precursor of sterols.

In yeast, squalene is converted to squalene epoxide, which is then cyclized to form lanosterol. Lanosterol has two methyl groups at position 4, a methyl group at position 14, a double bond at position 8(9) and an 8 carbon sidechain of the formula:

$$CH_3CH(CH_2)_2CH{=}C(CH_3)_2.$$

Lanosterol is sequentially demethylated at positions 14 and 4 to form zymosterol (cholesta-8,24-dienol), which is converted to ergosterol (ergosta-5,7,22-trienol), the most abundant sterol of naturally occurring, wild-type yeast via a series of five enzymatic reactions schematically diagramed in FIG. 1.

The five reactions are:

a. methylation of the carbon at position 24, catalyzed by a 24-methyltransferase;

b. movement of the double bond at position 8(9) to position 7(8), catalyzed by a Δ8→Δ7 isomerase;

c. introduction of a double bond at position 5(6), catalyzed by a 5-dehydrogenase (desaturase);

d. introduction of a double bond at position 22(23), catalyzed by a 22-dehydrogenase (desaturase); and e. removal of a double bond at position 24(28), catalyzed by a 24(28)-hydrogenass (reductase).

In wild-type yeast of the species *Saccharomyces cerevisiae* (*S. cerevisiae*), the predominant order of these reactions is thought to be a, b, c, d and e. [Parks et al., *CRC Critical Reviews in Microbioloy,* 6:301–341 (1978)].

According to such a predominant pathway, zymosterol is converted sequentially to fecosterol [ergosta-8,24(28)-dienol], episterol [ergosta-7,24(28)-dienol], ergosta-5,7,24(28)-trienol, ergosta-5,7,22,24(28)-tetraenol, and finally ergosterol.

If the enzymes catalyzing the reactions involved in the predominant pathway are substrate specific, then one would expect to find only the six sterols set forth above in yeast. Such, however, is not the case. Eighteen sterols have been found and described. [See, e.g., Parks et al., *CRC Critical Reviews in Microbioloy,* 6:301–341 (1978); Woods et al., *Microbios,* 10(A):73–80 (1974); Bard et al., *Lipids,* 12:645–654 (1977) (See Table 1)]. Thus, at least some of the enzymes are not substrate specific.

TABLE 1

| Sterol | Required* Enzymes |
|---|---|
| 1. Zymosterol (cholesta-8,24-dienol) | none |
| 2. fecosterol (ergosta-8,24(28)-dienol) | a |
| 3. episterol (ergosta-7,24(28)-dienol) | a,b |
| 4. ergosta-5,7,24(28)-trienol | a,b,c |
| 5. ergosta-5,7,22,24(28)-tetraenol | a,b,c,d |
| 6. ergosterol (ergosta-5,7,22-trienol) | a,b,c,d,e |
| 7. ergosta-7,22,24(28)-trienol | a,b,d |
| 8. cholesta-7,24-dienol | b |
| 9. cholesta-5,7,24-trienol | b,c |
| 10. cholesta-5,7,22,24-tetraenol | b,c,d |
| 11. ergosta-5,7-dienol | a,b,c,e |
| 12. ergosta-7,22-dienol | a,b,d,e |
| 13. ergosta-7-enol | a,b,e |
| 14. ergosta-5,8-dienol | a,c,e |
| 15. ergosta-5,8,22-trienol | a,c,d,e |
| 16. ergosta-8,22-dienol | a,d,e |
| 17. ergosta-8-enol | a,e |
| 18. ergosta-8,14,24(28)-trienol | a |

*Enzymes theoretically required for the synthesis of the designated sterol.

Despite the lack of substrate specificity, one might expect that specific alterations in the sterol biosynthetic pathway would have predictable consequences. Currently available data show that such predictability is not present.

For example, mutant *S. cerevisiae* with a defect in the expression of zymosterol-24-methyl-transferase (enzyme a), which mutants are designated erg6, might be expected to accumulate sterols 1 and 8–10 of Table 1, which sterols theoretically do not require the action of enzyme a for their synthesis. Parks et al., *CRC Critical Reviews in Microbiology,* 6:301–341 (1978), however, report that erg6 mutants accumulate only zymosterol (#1), cholesta-5,7,24-trienol (#9) and cholesta-5,7,22,24-tetranol (#10). Bard, M. et al., *Lipids,* 12:645–654 (1977), on the other hand, report that erg6 mutants accumulate only sterols #1 and #10.

Mutant *S. cerevisiae* with a defect in the expression of ergosta-5,7,24(28)-trienol-22-dehydrogenase (enzyme d), designated erg5, might be expected to accumulate sterols 1–4, 6, 8, 9, 11, 13, 14, 17 and 18. Parks et al., *CRC Critical Reviews in Microbiology,* 6:301–341 (1978) report, that erg5 mutants accumulate only ergosta-5,7-dienol (#11), ergosta-5,7,24(28)-trienol (#4), ergosta-8,14,24(28)-trienol (#18) and episterol (#3). In contrast, Bard et al., *Lipids,* 12:645–654 (1977) report that erg5 mutants accumulate zymosterol (#1), ergosta-5,7-dienol (#11), ergosta-5,7,24(28)-trienol (#4), ergosta-7,24(28)-dienol (#3) and ergosta-8,14,24(28)-trienol (#18).

Still further, mutant *S. cerevisiae* with a defect in episterol-5-dehydrogenase (enzyme c), designated erg3, might be expected to accumulate sterols 1–3, 7, 8, 12, 13 and 16–18. Parks et al., *CRC Critical Reviews in Microbiology,* 6:301–341 (1978) report that erg3 mutants accumulate only ergosta-7,22-dienol (#12), ergosta-8,22-dienol (#16), ergosta-7,22,24(28)-trienol (#7), fecosterol (#2) and episterol (#3).

These data, taken together, show that specific defects in the expression of one sterol synthetic enzyme do not lead to predictable changes in sterol accumulation. A similar degree of unpredictability is found when sterol accumulation is examined in mutants having two defects in enzymes of the sterol biosynthetic pathway.

Thus, for example, erg5-erg6 double mutants (defects in enzymes d and a) might be expected to accumulate sterols 1, 8 and 9. Parks et al. and Bard et al., above, report that erg5-erg6 double mutants accumulate only zymosterol (#1) and cholesta-5,7,24-trienol (#9).

These data relating to sterol accumulation in yeast show that specific alterations in enzyme activity do not result in predictable changes in sterol accumulation. The data further show a lack of agreement between different investigators studying identical alterations. The present invention furnishes a solution to the problem of unpredictability by providing a method and composition for increasing the accumulation of squalene and specific sterols in yeast.

SUMMARY OF THE INVENTION

The present invention generally provides a method of increasing squalene and specific sterol accumulation in mutant yeasts having a single or double defect in the expression of sterol biosynthetic pathway enzymes. This method comprises transforming such mutant yeasts with a recombinant DNA molecule comprising a vector operatively linked to an exogenous DNA segment that encodes a polypeptide having HMG-CoA reductase activity and a promoter suitable for driving the expression of HMG-CoA reductase in the transformed yeast.

The structural gene encoding a polypeptide having HMG-CoA reductase activity preferably encodes an active, truncated HMG-CoA reductase enzyme, which enzyme comprises the catalytic and at least a portion of the linker region that is free from the membrane binding region of HMG-CoA reductase enzyme. The copy number of the structural gene is increased by transforming a mutant yeast with a recombinant DNA molecule comprising a vector operatively linked to an exogenous DNA segment that encodes a polypeptide having a HMG-CoA reductase activity and a promoter that is suitable for driving the expression of the encoded polypeptide in the transformed yeast.

Suitable promoters include promoters that are subject to inducible regulation by factors either extrinsic or intrinsic to yeast. Preferably, both the promoter and the exogenous DNA segment are integrated into the chromosomal DNA of the transformed yeast.

The present invention most preferably provides a method of increasing squalene, zymosterol, cholesta-7,24-dienol and cholesta-5,7,24-trienol accumulation in yeast of the species *S. cerevisiae* comprising increasing the expression level of a structural gene encoding a polypeptide having HMG-CoA reductase activity in a mutant *S. cerevisiae* having defects in the expression of zymosterol-24-methyltransferase (erg6) and ergosta-5,7,24 (28)-trienol-22-dehydrogenase (erg5).

In further preferred embodiments, transformation of a mutant yeast having a defect in the expression of the enzyme episterol-5-dehydrogenase (erg3) results in a transformed, mutant yeast which overaccumulates squalene, ergosta-8,22-dienol, ergosta-7,22-dienol, ergosta-8-enol and ergosta-7-enol. Transformation of a mutant yeast having a double defect in the expression of zymosterol-24-methyltransferase and episterol-5-dehydrogenase enzymes (erg6 and erg3) results in a transformed mutant yeast which overaccumulates squalene, zymosterol and cholesta-7,24-dienol. Transformation of a mutant yeast having a defect in the expression of ergosta-5,7,24(28)-trienol-22-dehydrogenase (erg5) results in a transformed mutant yeast which overaccumulates zymosterol and a mixture of ergosta-5,7,24(28)-trienol and ergosta-5,7-dienol.

Transformation of mutant yeast is preferably accomplished using a recombinant DNA molecule selected from the group of plasmid vectors consisting of plasmids pSOC725ARC, pSOC106ARC, pARC306E, pARC300D, pARC300S, pARC300T and pARC304S. Most preferred is plasmid pARC304S.

The present invention further provides for a mutant species of *S. cerevisiae,* which mutant has a double defect in the expression of zymosterol-24-methyltransferase and ergosta-5,7,24(28)-trienol-22-dehydrogenase enzymes (erg5 and erg6). That mutant *S. cerevisiae* is designated ATC0402mu.

The present invention still further provides for a mutant species of *S. cerevisiae* having a single or double defect in the expression of enzymes that catalyze the conversion of squalene to ergosterol that is transformed with a recombinant DNA molecule comprising as described before.

The present invention still further provides for recombinant DNA molecules used to transform mutant yeasts such that the transformed mutant yeast overaccumulates squalene and specific sterols. Preferred recombinant DNA molecules are plasmids pARC304S, pARC300S, pARC300T, pARC300D, pARC306E, pSOC106ARC and pSOC725ARC.

The present invention provides several benefits and advantages.

One advantage of the present invention is the provision of methods known to result in the predictable accumulation of specific sterols.

Another advantage of the present invention is the ability to accumulate specific sterols to levels markedly greater than levels found in non-transformed yeast.

Still further benefits and advantages will be apparent to the skilled worker from the description that follows.

BRIEF DESCRIPTIONS OF THE DRAWINGS

FIG. 1 is a schematic diagram illustrating the various transformation steps involved in the metabolic conversion of zymosterol to ergosterol as shown and discussed in Bard et al., *Lipids,* 12(8):645 (1977). The letters (a–e) indicate the five enzymes responsible for catalyzing the individual transformation steps. Numerals alone or with the letter "C" and an enzymic name indicate the position of the enzymes' activities and the activity of each enzyme.

FIG. 2, shown as twelve panels designated FIG. 2-1 through 2-12, is the nucleotide base sequence (SEQ ID NO:1) and derived amino acid residue sequence (SEQ ID NO:2) for *S. cerevisiae* HMG-CoA reductase 1 published by Basson et al., *Mol. Cell Biol.,* 8(9):3797–3808 (1988). Nucleotides are numbered (left-hand side) in the 5' to 3' direction. Position 1 corresponds to the first nucleotide of the ATG triplet coding for the initiator methionine. The predicted amino acid sequence is shown below the nucleotide sequence. The amino acid residues are numbered (right-hand side) beginning with the initiator methionine.

FIG. 3 is a schematic diagram showing the physical structure and genetic organization of plasmid pSOC725ARC. Plasmid pSOC725ARC was constructed to place a coding sequence for a truncated HMG-CoA reductase gene under control of a GAL 1-10 promoter. This plasmid also contains the TRP-1 gene and the yeast 2 micron origin of replication. Certain restriction sites indicated by lines linked to the arcs and abbreviation for their respective restriction endonuclease enzymes are indicated.

FIG. 4 is a schematic diagram showing the physical structure and genetic organization of plasmid pSOC106ARC. Plasmid pSOC106ARC was constructed to place a coding sequence for an intact HMG-CoA reductase gene under the control of a GAL 1-10 promoter. Plasmid pSOC106ARC also contains the TRP-1 gene and the yeast 2 micron origin of replication. Certain restriction sites are indicated as in FIG. 3.

FIG. 5 is a schematic diagram showing the physical structure and genetic organization of plasmid pARC306E. Plasmid pARC306E was constructed to place a coding sequence for a truncated HMG-CoA reductase gene under control of a GAL-1 promoter. Plasmid pARC306E also contains the TRP-1 gene. Certain restriction sites are indicated as in FIG. 3.

FIG. 6 is schematic diagram showing the physical structure and genetic organization of plasmid pARC300D. Plasmid pARC300D was constructed to place a coding sequence for a truncated HMG-CoA reductase gene under the control of a PGK promoter. Plasmid pARC300D also contains the TRP-1 gene. Certain restriction sites are indicated as in FIG. 3.

FIG. 7 is a schematic diagram showing the physical structure and genetic organization of plasmid pARC300S. Plasmid pARC300S was constructed to place a coding sequence for a truncated HMG-CoA reductase gene under control of a PGK promoter. Plasmid pARC300S also contains a URA 3 selectable marker. Certain restriction sites are indicated as in FIG. 3.

FIG. 8 is a schematic diagram showing the physical structure and genetic organization of plasmid pARC300T. Plasmid pARC300T was constructed to place a coding sequence for a truncated HMG-CoA reductase gene under control of a PGK promoter. Plasmid pARC300T also contains a URA 3 selectable marker. Certain restriction sites are indicated as in FIG. 3.

FIG. 9 is a schematic diagram showing the physical structure and genetic organization of plasmid pARC304S. Plasmid pARC304S was constructed to place a coding sequence of a truncated HMG-CoA reductase gene under the control of an ADH promoter. Plasmid pARC304S also contains a URA 3 selectable marker. Certain restriction sites are indicated as in FIG. 3.

DETAILED DESCRIPTION OF THE INVENTION

I. Definitions

Figure 1:
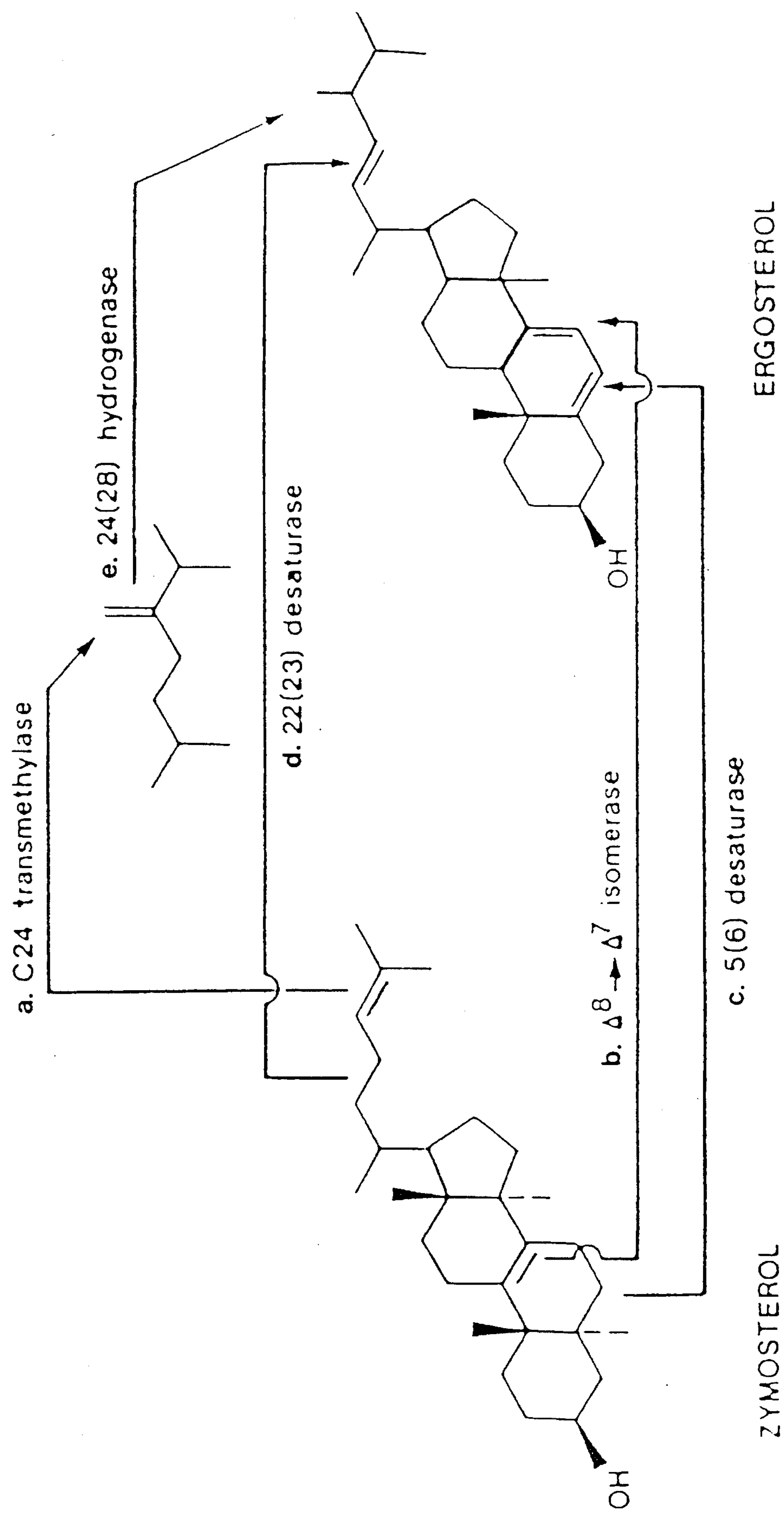

The following words and phrases have the meanings set forth below.

Expression: The combination of intracellular processes, including transcription and translation, undergone by a structural gene to produce a polypeptide.

Expression vector: A DNA sequence that forms control elements that regulate expression of structural genes when operatively linked to those genes.

Operatively linked: A structural gene is covalently bonded in correct reading frame to another DNA (or RNA as appropriate) segment, such as to an expression vector so that the structural gene is under the control of the expression vector.

Promoter: A recognition site on a DNA sequence or group of DNA sequences that provide an expression control element for a structural gene and to which RNA polymerase specifically binds and initiates RNA synthesis (transcription) of that gene.

Recombinant DNA molecules: A hybrid DNA sequence comprising at least two nucleotide sequences not normally found together in nature.

Structural gene: A DNA sequence that is expressed as a polypeptide, i.e., an amino acid residue sequence.

Vector: A DNA molecule capable of replication in a cell and/or to which another DNA segment can be operatively linked so as to bring about replication of the attached segment. Alternatively, a vector can be a non-replicating vector that is integrated into the chromosome of the transformed cell. A plasmid is an exemplary vector.

II. The Invention

The present invention relates to compositions and methods for increasing the accumulation of squalene and specific sterols in yeast cultures as well as to the yeast that exhibit increased squalene and sterol accumulation relative to a non-transformed yeast. Preferred yeasts are yeasts of the Saccharomyces or Candida genus. A more preferred yeast is *Saccharomyces cerevisiae* (*S. cerevisiae*).

A yeast contemplated by this invention is transformed with an added structural gene that encodes a polypeptide having HMG-CoA reductase activity, that encoded polypeptide being expressed in the transformed yeast. Preferred non-transformed yeasts are mutant species having a single or double defect in the expression of enzymes involved in converting zymosterol to ergosterol (sterol biosynthetic pathway enzymes). The non-transformed and transformed yeasts compared are of the same species, such as *S. cerevisiae.*

Sterol production in a yeast culture of the present invention is increased by increasing the cellular activity of the enzyme HMG-CoA reductase, which enzyme catalyzes the conversion of 3-hydroxy-3-methylglutaryl Coenzyme A (HMG-CoA) to mevalonate. As used herein, "cellular activity" means the total catalytic activity of HMG-CoA reductase in a yeast cell.

Cellular HMG-CoA reductase activity is increased by increasing the expression level of a structural gene encoding a polypeptide having HMG-CoA reductase catalytic activity. Expression of that encoded structural gene enhances the cellular activity of that enzyme. The expression level is increased by methods well known in the art. For example, expression of a structural gene is increased by deregulating the promoter, which controls expression of such a structural gene. The promoter that regulates expression of the HMG-CoA reductase gene in a normal, wild-type yeast can be identified and excised from the genome. A new promoter, which allows for overexpression of the HMG-CoA reductase gene, is then inserted according to standard transformation techniques. A preferred means of increasing the expression level of a structural gene encoding a polypeptide having HMG-CoA reductase catalytic activity is to increase the copy number of a structural gene encoding such a polypeptide.

The copy number is increased by transforming a yeast cell with a recombinant DNA molecule comprising a vector operatively linked to an exogenous DNA segment that encodes a polypeptide having HMG-CoA reductase activity, and a promoter suitable for driving the expression of said polypeptide in said yeast. Such a polypeptide is catalytically active, and is preferably a truncated HMG-CoA reductase protein.

Thus, a transformed yeast cell has one or more added genes that encode a polypeptide having HMG-CoA reductase activity relative to a non-transformed yeast of the same species. As such, a transformed yeast can be distinguished from a non-transformed yeast by standard technology such as agarose separation of DNA fragments or mRNAs followed by transfer and appropriate blotting with DNA or RNA or by use of polymerase chain reaction technology, as are well known. Relative HMG-CoA reductase activity of the transformed and non-transformed yeasts can also be compared, with a relative increase in HMG-CoA reductase activity in transformed yeasts being indicative of transformation.

The accumulation of squalene and specific sterols can also be used to distinguish between non-transformed and transformed yeasts.

A. Structural Genes

The present invention contemplates transforming a yeast with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane binding region and the linker region.

The catalytic region contains the active site of the HMG-CoA reductase enzyme and comprises about forty percent of the total, localized on the COOH-terminal portion of intact HMG-CoA reductase enzyme. The membrane binding region contains hydrophobic amino acid residues and comprises about fifty percent of the total, localized on the $NH_2$-terminal portion of intact HMG-CoA reductase enzyme. The linker region connects the catalytic and membrane binding regions, and constitutes the remaining about ten percent of the intact enzyme.

As discussed in greater detail below, only the catalytic region of HMG-CoA reductase is needed herein. Thus, a structural gene that encodes a polypeptide corresponding to that catalytic region is the minimal gene required for transforming yeasts. However, larger polypeptide enzymes and their structural genes are preferred. Thus, the present invention contemplates use of truncated structural genes that encode the active catalytic region, or the catalytic region plus at least a portion of the linker region that is free from the membrane binding region of HMG-CoA reductase.

A structural gene encoding a polypeptide having HMG-CoA reductase activity can be obtained or constructed from a variety of sources and by a variety of methodologies, [See, e.g., Carlson et al., *Cell,* 28:145 (1982); Rine et al., *Proc. Nat. Acad. Sci. U.S.A.,* 80:6750 (1983)]. Exemplary of such structural genes are the mammalian and yeast genes encoding HMG-CoA reductase.

The mammalian genome contains a single gene encoding HMG-CoA reductase. The nucleotide base sequence of the hamster and human gene for HMG-CoA reductase have been described. A composite nucleotide sequence of cDNA corresponding to the mRNA, as well as the derived amino acid residue sequence, for hamster HMG-CoA reductase is found in Chin et al., *Nature,* 308:613 (1984) and SEQ ID NO:3. The composite nucleotide sequence in that paper, comprising about 4606 base pairs, includes the nucleotide sequence encoding the intact hamster HMG-CoA reductase enzyme.

Intact hamster HMG-CoA reductase comprises about 887 amino acid residues, shown in SEQ ID NO:4.

A preferred structural gene is one that encodes a polypeptide corresponding to only the catalytic region of the enzyme. Two catalytically active segments of hamster HMG-CoA reductase have been defined, [Liscum et al., *J. Biol. Chem.,* 260(1):522 (1985)]. One catalytic region has an apparent size of about 63 kDa and comprises amino acid residues from about position 373 to about position 887 of SEQ ID NO:4. A second catalytic region has an apparent size of about 53 kDa and comprises amino acid residues from about position 460 to about position 887 of SEQ ID NO:4. The about 63 kDa catalytically active segment is encoded by base pairs from about nucleotide position 1282 to about nucleotide position 2824 of the sequence in SEQ ID NO:3. The about 53 kDa catalytically active segment is encoded by base pairs from about nucleotide position 1543 to about nucleotide position 2824 of the sequence in SEQ ID NO:3.

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1183 to about nucleotide position 1282 or from about position 1183 to about position 1543 respectively of the sequence in SEQ ID NO:3. The structural gene encoding the linker region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme. A truncated hamster HMG-CoA reductase gene, designated HMGR-Δ227, comprising nucleotides 164–190 and 1187–2824 of the sequence in SEQ ID NO:3, which encodes amino acid residues 1–9 (from the membrane binding region) and 342–887 has been used to transform cells lacking HMG-CoA reductase, [Gil et al., *Cell,* 41:249 (1985)].

A structural gene encoding a polypeptide comprising a catalytically active, truncated or intact HMG-CoA reductase enzyme from other organisms such as yeast can also be used in accordance with the present invention.

Yeast cells contain two genes encoding HMG-CoA reductase. The two yeast genes, designated HMG1 and HMG2, encode two distinct forms of HMG-CoA reductase, designated HMG-CoA reductase 1 and HMG-CoA reductase 2. The nucleotide base sequence of HMG1 (SEQ ID NO:1) as well as the amino acid residue sequence of HMG-CoA reductase 1 (SEQ ID NO:2) are presented in FIG. 2, reprinted from Basson et al., *Mol. Cell Biol.,* 8(9):3797 (1988).

The entire HMG1 gene comprises about 3360 base pairs. Intact HMG-CoA reductase 1 comprises an amino acid sequence of about 1054 amino acid residues.

The entire HMG2 gene comprises about 3348 base pairs shown in SEQ ID NO:5. Intact HMG-CoA reductase 2 comprises about 1045 amino acid residues shown in SEQ ID NO:6 (Basson et al., above).

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about residue 1054: i.e., the COOH-terminus. A structural gene that encodes the catalytic region comprises base pairs from about nucleotide position 1974 to about position 3282 of FIG. 2 and SEQ ID NO:1.

The linker region of HMG-CoA reductase 1 comprises an amino acid sequence from about residue 525 to about residue 617. A structural gene that encodes the linker region comprises nucleotides from about position 1695 to about position 1974 of FIG. 2. A structural gene encoding a polypeptide comprising the catalytic region and at least a portion of the linker region of yeast HMG-CoA reductase 1 preferably comprises the structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane binding region of the enzyme. Such a structural gene preferably comprises base pairs from about nucleotide position 121 to about position 146 and from about position 1695 to about position 3282 of FIG. 2 and SEQ ID NO:1.

A construct similar to those above from an analogous portion of yeast HMG-CoA reductase 2 can also be utilized.

It will be apparent to those of skill in the art that the nucleic acid sequences set forth herein, either explicitly, as in the case of the sequences set forth above, or implicitly with respect to nucleic acid sequences generally known and not presented herein, can be modified due to the built-in redundancy of the genetic code and non-critical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall lengths. That minimal length defines the length of a DNA segment having a sequence that encodes a particular polypeptide having HMG-CoA reductase activity. As is well known in the art, so long as the required DNA sequence is present and in proper reading frame, (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, so long as the DNA segment is free of such interfering DNA sequences, the maximum size of a recombinant DNA molecule, particularly an expression vector, is governed mostly by convenience and the vector size that can be accommodated by a host cell, once all of the minimal DNA sequences required for replication and expression, when desired, are present. Typically, a DNA segment of the invention can be up to 15,000 base pairs in length. Minimal vector sizes are well known.

B. Recombinant DNA Molecules

A recombinant DNA molecule of the present invention can be produced by operatively linking a vector to a useful DNA segment to form a plasmid such as discussed herein. Particularly preferred recombinant DNA molecules are discussed in detail in Examples 2 to 7, hereafter. A vector capable of directing the expression of a polypeptide having HMG-CoA reductase activity is referred to herein as an "expression vector".

Such expression vectors contain expression control elements including the promoter. The polypeptide coding genes are operatively linked to the expression vector to permit the promoter sequence to direct RNA polymerase binding and expression of the desired polypeptide coding gene. Useful in expressing the polypeptide coding gene are promoters that are inducible, viral, synthetic, constitutive as described by Poszkowski et al., *EMBO J.,* 3:2719 (1989) and Odell et al., *Nature,* 313:810 (1985), and temporally regulated, spatially regulated, and spatiotemporally regulated as disclosed in Chau et al., *Science,* 244:174–181 (1989). The promoter preferably comprises a promoter sequence whose function in regulating expression of the structural gene is substantially unaffected by the amount of sterol in the cell. As used herein, the term "substantially unaffected" means that the promoter is not responsive to direct feedback control by the sterols accumulated in transformed cells.

A promoter is also selected for its ability to direct the transformed yeast's transcriptional activity to the structural gene encoding a polypeptide having HMG-CoA reductase activity. Structural genes can be driven by a variety of promoters in yeast.

Promoters utilized with the present invention are those preferably regulated by factors, which can be monitored and controlled in the internal or external environment of the transformed cell. Examples of promoters inducibly regulated by factors in the cell's external environment (extrinsic factors) are the GAL 1 promoter, the GAL 10 promoter, the GAL 1-10 promoter, the GAL 7 promoter, the metallothionine promoter, the a-factor promoter, the invertase promoter and the enolase promoter. Preferred are the well known GAL 1, the GAL 10 and the GAL 1-10 promoters.

Examples of promoters subject to inducible regulation by factors in the cell's internal environment (intrinsic factors) are the phosphoglycerate kinase (PGK) promoter, the triose-phosphate isomerase (TPI) promoter, the alcohol dehydrogenase (ADH) promoter and the repressible acid phosphatase promoter. Preferred are the well known PGK and the ADH promoters.

The choice of which expression vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene included in the DNA segment to which it is operatively linked.

The present method contemplates a plasmid vector. The plasmid vectors of the present invention can be incorporated either within (integrated) or without (episomal) the chromosomes of the transformed cell. An episomal plasmid includes an origin of replication for yeast, the nucleic acid sequence that encodes a polypeptide having HMG-CoA reductase activity, a promoter, and a selective marker. The selective marker can include genes conveying antibiotic resistance, or permitting an auxotrophic host to metabolize a substrate that it would not otherwise be able, but for the presence of the plasmid vector. However, the use of antibiotic resistance as a selective marker requires growing organisms in an antibiotic culture media. Due to the expense of the antibiotic, organisms dependent on antibiotics are difficult to develop commercially. Generally, auxotrophic organisms are used for yeast.

Auxotrophic organisms can be produced by mutation and culture techniques which are well known in the art. Selective markers which can complement an auxotrophic host organism include the well known TRP 1 gene encoding phosphoribosyl anthraniline isomerase, the URA 3 gene encoding orotine-5' phosphate decarboxylate, the LEU 2 gene encoding isopropylmalate isomerase, and the HIS 3 gene encoding histidinol dehydrogenase. A preferred selective marker for an auxotrophic host is TRP 1. Preferred episomal plasmid vectors are pSOC725ARC and pSOC106ARC.

Episomally replicating vectors are sometimes difficult to maintain in host organisms for long periods of time in liquid culture, especially when the selective pressure used to maintain the vector is complementation of a nutritional auxotrophy. A preferred embodiment of the present invention includes an integrating vector which requires little or no selective pressure to maintain base sequences for the polypeptide having HMG-CoA reductase activity and the promoter.

Integrating vectors, in accordance with the present invention, include base sequences that encode a polypeptide having HMG-CoA reductase activity, a promoter, a selective marker and sequences homologous to host chromosomal DNA that permit the base sequences to be incorporated within the chromosome via homologous recombination. The homologous region includes restriction sites that permit the plasmid to become linear. In linear form, the plasmid can recombine at homologous regions of the chromosome. Integrating vectors do not include origins of replication for the host organism.

Preferred integrating vectors are pARC300S, pARC300T, pARC300D, pARC306E and pARC304S. Plasmid vector pARC304S is most preferred as evidenced by its ability to generate the greatest enhancement in sterol accumulation (see Example 15). The basic genetic characteristics of preferred plasmid vectors are summarized in Table 2, below.

TABLE 2

| Plasmid Vector | Genetic Characteristics |
|---|---|
| pSOC106 | TRP1-2μori-GAL 1-HMG1* |
| pSOC725 | TRP1-2μori-GAL 10-tHMG1** |
| pARC306E | TRP1-PGK-tHMG1 |
| pARC300D | TRP1-PGK-tHMG1 |
| pARC300S,T | URA3-PGK-tHMG1-ura3 term |
| pARC304S | URA3-ADH-tHMG1-ura3 term |

*HMG1 - gene encoding intact *S. cerevisiae* HMG-CoA reductase 1.
**tHMG1 - gene encoding catalytic region and a portion of the linker region of *S. cerevisiae* HMG-CoA reductase 1.

Individuals skilled in the art will readily recognize that episomal and integrating vectors are often amplified in organisms other than the intended host and require means of replication and selection in the non-host organism. Generally, the non-host organism is *Escherichia coli* due to its well-known features and characteristics.

In preferred embodiments, the vector used to express the polypeptide coding gene includes a selection marker that is effective in a yeast cell, such as the URA 3 or TRP 1 markers. Other suitable selection means for use in amplifying the vectors in bacteria include antibiotic markers, such as genes encoding for beta lactamase (penicillin resistance), chloramphenicol transacetylase (chloramphenicol resistance), and neomycin phosphotransferase (kanamycin and neomycin resistance).

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

C. Transformed Yeasts and Methods of Transformation

The copy number of a gene coding for a polypeptide having HMG-CoA reductase activity is increased by transforming a desired yeast with a suitable vector that contains that structural gene. Expression of that gene in the transformed yeast enhances the activity of HMG-CoA reductase.

Yeast cells are transformed in accordance with the present invention by methods known and readily apparent to those of skill in the yeast transformation art, [See, e.g., Hinnen et al., *Proc. Natl. Acad. Sci. USA,* 75:1929-(1978); Ito et al., Bact., 5:163–168 (1983) ].

A preferred general method of transformation is the lithium acetate procedure of Ito et al., above. Yeast cells are grown to a concentration about $2\times10^7$ cells/ml in a medium containing yeast extract, bactopeptone and dextrose. Cells are collected by low speed centrification and resuspended in a transformation medium containing lithium acetate in a Tris-EDTA buffer.

Cells are maintained in the transformation medium for about one hour at about 30° C. Recombinant DNA molecules of desired composition are added to the transformation medium cell suspension and the mixture is maintained at about 30° C. for about one-half hour. Polyethylene glycol (M.W. 4000) is then added to the cell suspension such that the final concentration of polyethylene glycol is about 35 percent weight/volume (w/v). Cells are maintained in the polyethylene glycol-containing solution at about 30° C. for about two hours and then at about 42° C. for an additional five minutes. Sterile distilled water is added to the cell suspension, and the cells collected by low speed centrification. Further specifics are provided hereinafter.

Successfully transformed cells are identified by growing the transformed cells on selection medium, identifying cell characteristics indicative of transformation (i.e., increased accumulation of squalene or specific sterois), analyzing nucleic acids isolated from such transformed cells with standard techniques such as Southern blot analysis, [Holm et al., *Gene,* 42:169 (1986)].

D. Mutated Yeasts

The yeasts utilized in accordance with the present invention are mutated yeasts having single or double defects in the expression of enzymes that catalyze the conversion of zymosterol to ergosterol. Such enzymes are referred to herein as "erg" gene products. Table 3 below lists the particular erg designations for specific enzyme expression defects.

TABLE 3

| Enzyme Expression Defect | Mutant Designation |
|---|---|
| zymosterol-24-methyltransferase | erg6 |
| ergosta-5,7,24(28)-trienol-22-dehydrogenase | erg5 |
| episterol-5-dehydrogenase | erg3 |

Mutants used in accordance with the present invention can be purchased or generated from commercially available sources such as the Yeast Genetic Stock Center (Berkeley, Calif.). For example, erg5 and erg5-erg6 double mutants are produced from commercially available sources.

Mutant yeast ATC0402mu, an erg5-erg6 double mutant, is constructed by crossing a commercially available erg6 mutant yeast, M610-12B, with a commercially available erg5 mutant, po15αΔ22, and then crossing the resultant double mutant, ATC0403mu, with a wild-type yeast. Mutant yeast ATC0402mu and its derviative mutant yeast ATC0315rc are the most preferred mutants for transformation with the plasmid vectors of the present invention.

Alternatively, ATC0403 is crossed with a different wild-type, and mutants having desired genotypes are back-crossed twice with wild-type yeast to yield species ATC4124, an erg5 mutant.

Mutants are also obtained by well known methods of inducing mutations. See, e.g., Boeke et al., *Mol. Gen. Genet.,* 197:345–346 (1984); Sherman et al., *Methods and Yeast Genetics,* Cold Spring Harbor Laboratory, N.Y. (1986).

In a preferred embodiment, wild-type yeasts are transformed with an inducible "TY1-neo" transposon as a mutagenic agent. Plasmid pJEF1105, containing a GAL:TY1-neo expression cassette, is used as the transforming agent. Boeke et al., *Science,* 239:280–282 (1989). Competent transformants demonstrating both neomycin and nystatin resistance are then evaluated for sterol content.

Transformation of wild-type yeast with pJEF1105 yields mutant ATC6118, an erg3 mutant, and mutant ATC0501, an erg6 mutant.

Mutants having single expression defects are then crossed to generate mutants having double defects in enzyme expression. For example, the crossing of mutant ATC6118 with mutant ATC0501 yields mutant ATC6119, an erg3-erg6 double mutant.

The genotype of exemplary mutants contemplated for use in the present invention are presented in Table 4 below. Genotype symbols are used in accordance with convention cited in Mortimer et al. *Yeast,* 5:321–403 (1989) and Broach, *The Molecular Biology of the Yeast Saccharomyces. Life Cycle and Inheritance,* Strathern, Jones and Broach, eds., Cold Spring Harbor Laboratory, pp. 653–727 (1981).

TABLE 4

| Species | genotype |
|---|---|
| po15αΔ22 | a, erg5 |
| M610-12β | α, ile3, erg6-5, trpl, gal2 |
| DBY745 | α, adel, ura3-52, leu2-100, leu2-122, MEL, gal 1 gal 10 |
| YNN281 | α, trpl-Δ, his3Δ-200, ura 3-52, lys 2 |
| ATC0403mu | a, trpl, gal, erg5, erg6 |
| ATC0402mu | a, trpl, GAL, erg5, erg6 |
| ATC6118 | a, his3Δ-200, erg3, ura3-52, GAL |
| ATC4124 | α, erg5, trpl, GAL |
| ATC4154 | a, ura3-52, erg7, gal |
| ATC6119 | α, erg3, erg6, ura3-52, GAL |
| ATC1500cp | a, erg5, erg6 |
| ATC0315rc | a, ura3, erg5, erg6 |
| ATC1551 | a, erg5, erg6 |

E. Squalene and Sterol Accumulation in Transformed Yeast

The transformed mutant yeast species of the present invention overaccumulate squalene and specific sterols relative to non-transformed mutants of the same species. Relative to a non-transformed erg3 mutant, an erg3 mutant transformed with a plasmid vector used herein overaccumulates squalene, ergosta-8,22-dienol, ergosta-7,22-dienol, ergosta-8-enol and ergosta-7-enol.

Relative to a non-transformed erg5 mutant, an erg5 mutant transformed with a plasmid vector used herein overaccumulates squalene, zymosterol, and a mixture of ergosta-5,7,24(28)-trienol and ergosta-5,7 dienol.

Similar results are seen when mutants having double defects in enzymes of the sterol synthetic pathway are transformed. Relative to a non-transformed erg3-erg6 mutant, an erg3-erg6 mutant transformed with a useful plasmid vector overaccumulates squalene, zymosterol and cholesta-7,24-dienol.

Relative to a non-transformed erg5-erg6 mutant, an erg5-erg6 double mutant transformed with the plasmid vector useful herein overaccumulates squalene, zymosterol, cholesta-5,7,24-trienol and cholesta-7,24-dienol.

F. HMG-CoA Reductase Activity In Transformed Yeasts

The expression of a structural gens encoding a polypeptide having HMG-CoA reductase activity in the transformed yeast of the present invention enhances the cellular activity of said HMG-CoA reductase. As a result of transformation, the copy number of an added gens encoding a polypeptide having HMG-CoA reductase activity is increased from 1 to about 2 to about 10.

Cellular activity of HMG-CoA reductase in such transformed cells is almost linearly proportional to the increase in copy number through a copy number of about 6 and then falls slightly when a copy number of 9 is reached. Thus, when the copy number is increased to about 2, HMG-CoA reductase activity is elevated to a level about 1.4 times the activity observed in non-transformed yeast. A further increase in the copy number to a level of about 6 is accompanied by a further increase in HMG-CoA reductase activity to a level about 2.6 times that found in non-transformed yeast. Increases in the copy number beyond about 6 to about 9 are not accompanied by further increases in HMG-CoA reductase activity. A transformed yeast having a copy number of about 9 has a level of HMG-CoA reductase activity about equal to about twice that seen in non-transformed yeast.

G. Harvesting of Sterols

If desired, transformed yeasts are harvested to recover the sterol product. Most of the sterol in our genetically transformed yeast of this invention occurs in the form of fatty acid esters. To obtain free sterols, it is therefore necessary to saponify the "yeast pulp" in base, e.g., as described in the Examples below (2:1 EtOH/$H_2O$ containing 20 percent w/v KOH).

In a preferred embodiment, harvesting comprises:

(i) homogenizing sterol-containing transformed yeasts to produce a pulp; and (ii) extracting the sterol(s) from the pulp with an appropriate basic solvent such as an organic solvent or by supercritical extraction followed by base saponification in an appropriate solvent [Favati et al., *J. Food Sci.*, 53:1532 (1988) and the citations therein] to produce a sterol-containing liquid solution or suspension; and (iii) isolating the sterol(s) from the solution or suspension.

Transformed yeasts are homogenized to produce a pulp using methods well known to one skilled in the art. This homogenization can be done manually, by a machine, or by a chemical means. The pulp consists of a mixture of the sterol of interest, residual amounts of precursors, cellular particles and cytosol contents, which is subjected to extraction procedures.

Sterol(s) can be extracted from the pulp produced above to form a sterol-containing solution or suspension. Such extraction processes are common and well known to one skilled in this art. For example, the extracting step can consist of soaking or immersing the pulp in a suitable solvent. This suitable solvent is capable of dissolving or suspending the sterol present in the pulp to produce a sterol-containing solution or suspension. Solvents useful for such an extraction process are well known to those skilled in the art and include several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction.

Yeasts transformed with a structural gene for an active, truncated HMG-CoA reductase enzyme are grown under suitable culture conditions for a period of time sufficient for sterols to be synthesized. The sterol-containing yeast cells are then lysed chemically or mechanically, and the sterol is extracted from the lysed cells using a liquid organic solvent, as described before, to form a sterol-containing liquid solution or suspension. The sterol is thereafter isolated from the liquid solution or suspension by usual means such as chromatography.

The sterol is isolated from the solution or suspension produced above using methods that are well known to those skilled in the art of sterol isolation. These methods include, but are not limited to, purification procedures based on solubility in various liquid media, chromatographic techniques such as column chromatography and the like.

Best Mode For Carrying Out The Invention

The following examples illustrate the best mode of carrying out the invention and are not to be construed as limiting of the specification and claims in any way.

EXAMPLE 1

Transformation of *S. cerevisiae*

Yeast of the species *S. cerevisiae* were transformed in accordance with a lithium acetate procedure, [Ito et al., *J. Bacteriol.*, 153:163–168 (1983)]. Yeast cells were grown in about 50 ml of YEPD medium (yeast extract 1 percent w/v, bactopeptone, 2 percent w/v; and dextrose, 2 percent w/v) overnight at about 30° C. When the concentration of cells was about $2\times10^7$ cells/ml, the cells were collected by low speed centrifugation. Cells appearing in the pellet of the centrifugation were suspended in about 50 mls of TE buffer (10 mM Tris.Cl, 1 mM EDTA) and repelleted by centrifugation. The pellet from this second centrifugation was resuspended in about 1.0 ml of TE buffer. To 0.5 ml of this cell suspension were added 0.5 ml of 0.2M lithium acetate (LiOAc), and the suspension was maintained at about 30° C. for one hour with constant shaking.

Recombinant DNA (about 10 µg in up to 15 µl of TE buffer) was added to 100 µl of the TE-LiOAc cell suspension and the admixture maintained at about 30° C. for one-half hour without shaking. The DNA-containing cell suspension was then well mixed with polyethylene glycol (44 percent w/v) such that the final concentration of polyethylene glycol (PEG) was about 35 percent (w/v).

The cells were maintained in this PEG solution at about 30° C. for about two hours and then at about 42° C. for about five minutes. About 10 ml of sterile, distilled water was added to each suspension and the cells were collected by low speed centrifugation. This procedure was repeated, and the collected cells were dispersed in about 1.0 ml of distilled water. Approximately 100 to 200 µl of this suspension were then spread-plated on selective medium.

Transformation of cells was confirmed by growth on selection medium, identification of cell characteristics indicative of transformation (i.e., increased levels of selected sterols or squalene), and Southern blot analysis of nucleic acid isolated from such transformed cells [Holm et al., *Gene,* 42:169–173 (1986)].

EXAMPLE 2

Construction of Episomal Plasmid pSOC725ARC

Plasmid pSOC725ARC (See FIG. 3) was constructed to place a coding sequence for a truncated HMG1 gene under control of the GAL 1 portion of a GAL 1-10 promoter. Plasmid pSOC725ARC also contains the TRP 1 gene and the yeast 2 micron origin of replication (IR1). This plasmid was prepared from intermediate plasmids as follows.

The TRP 1-ARS gene of *S. cerevisiae* was removed from plasmid YRP12 [Stinchcomb et al. *Nature,* 282:39 (1979)] by digestion with Eco RI. The 1445 base pair DNA fragment containing the TRP 1-ARS gene was purified on an agarose gel and ligated into plasmid pUC8 (Viera et al., *Gene,* (1982)), which had been digested with Eco RI to form plasmid pSOC742.

A yeast episomal replication origin, obtained from purified *S. cerevisiae* two-micron plasmid DNA, was digested with Eco RI and then treated with the Klenow fragment of *E. coli* DNA polymerase 1 to yield an about 2240 base pair fragment containing the two-micron origin of DNA replication. The about 2240 base pair fragment was purified by agarose gel electrophoresis and ligated into plasmid pUC8, which had been digested with Sma I to form plasmid pSOC743.

Plasmid pSOC742 was cleaved with Bam HI and Bgl II to yield an 857 base pair, TRP 1-containing gene fragment, which was inserted into pSOC743 that had been cut with Bam HI to form plasmid pSOC744.

The MEL1 gene was removed from plasmid pMP550 [Sumner-Smith et al., *Gene,* 36:333–340 (1985)] with restriction endonucleases Eco RI and Bam HI, and the about 2858 base pair restriction fragment containing MEL1 was purified on an agarose gel. The purified fragment was then ligated into plasmid pUC8 which had been digested with Eco RI and Bam HI to form plasmid pSOC741.

The final stage of assembly of pSOC740 was achieved by purifying an about 3101 base pair, Eco RI restriction fragment of pSOC744 that contained the TRP 1 and two-micron origin, and ligating it into Eco RI-cleaved plasmid pSOC741 to form plasmid pSOC740.

The GAL 1-10 promoter was excised from pBM258, [Johnston et al., *Proc. Natl. Acad. Sci. USA,* 79:6971–6975 (1982)] as a 685 base pair Bam HI-Eco RI restriction fragment, and ligated into pUC18, which had been digested with Bam HI and Eco RI to form plasmid pSOC711.

Plasmid pSOC740 was digested with Eco RI and the resulting 3101 base pair fragment, containing the two-micron origin of replication and the TRP 1 gene, was isolated and ligated into the Eco RI digested plasmid p8OC711 to produce plasmid pSOC712, in which the TRP 1 gene is proximal to the GAL 1-10 promoter.

A Pst I restriction site spanning the coding sequence for amino acid residues 529–530 of HMG-CoA reductase 1 was chosen as the point at which to introduce both a new Bam HI restriction site and a new initiator methionine codon. A 1706 base pair Pst I-Eco RI restriction fragment, containing the coding sequence for the COOH-terminal half of HMG-CoA reductase 1, was purified from a digest of pJR59, [Basson et al., *Proc. Natl. Acad. Sci. USA,* 83:5563–5567 (1986)]. This purified pJR59 fragment and a synthetic oligonucleotide:

d5't-GATCCGTCGACGCATGCCTGCA-3' (SEQ ID NO:7)

d3'-GCAGCTGCGTACGG-5' (SEQ ID NO:8)

were ligated with pUC18 [Yanisch-Perron et al., *Gene,* 33:103–119 (1985)], which had been cleaved with Bam HI and Eco RI.

The resulting plasmid, pSOC937, contained a Bam HI restriction site 12 base pairs upstream of the truncated HMG-CoA reductase coding sequence initiator methionine. The polypeptide formed from initiation at that point had initial methionine and proline residues followed by amino acid residues 530 through 1054 of the natural HMG-CoA reductase 1.

Figure 3:
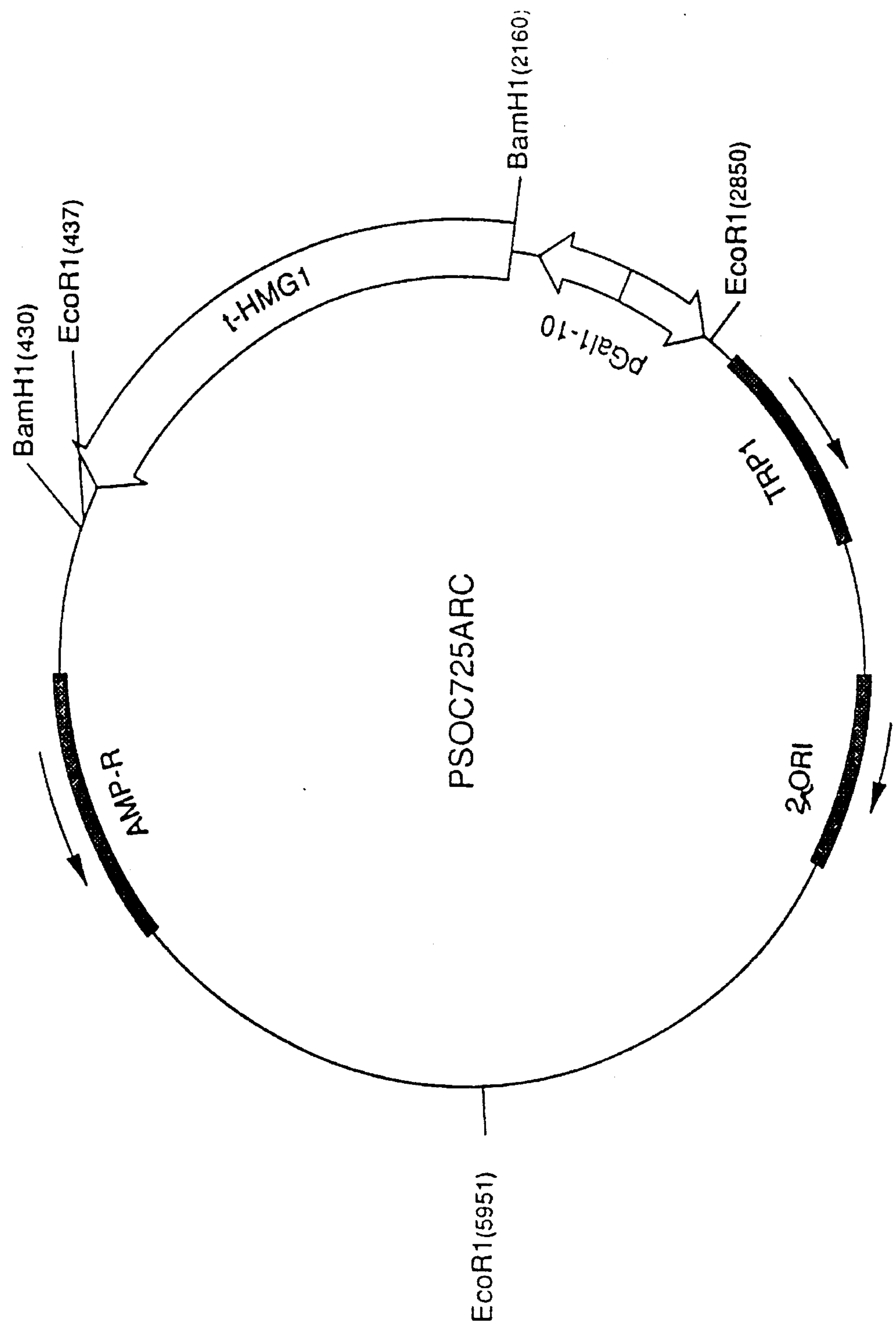

The Eco RI restriction site, which is at the 3' end of the gene, is located 135 base pairs past the end of the coding sequence for the truncated HMG-CoA reductase protein. The truncated gene for HMG-CoA reductase was placed into plasmid pSOC712 by converting the Eco RI site at the 3' end of the truncated reductase gene to a Bam HI site (Klenow polymerase filled, ligated to an oligonucleotide, d5-CG-GATCCG, specifying the Bam HI restriction site) and cleaving the preparation with endonuclease Bam HI. A purified, resulting 1728 base pair Bam HI ended restriction fragment from pSOC937 was ligated into the Bam HI-digested pSOC712 to produce plasmid pSOC725ARC, whose schematic restriction map is shown in FIG. 3.

EXAMPLE 3

Construction of Episomal Plasmid pSOC106ARC

Figure 4:
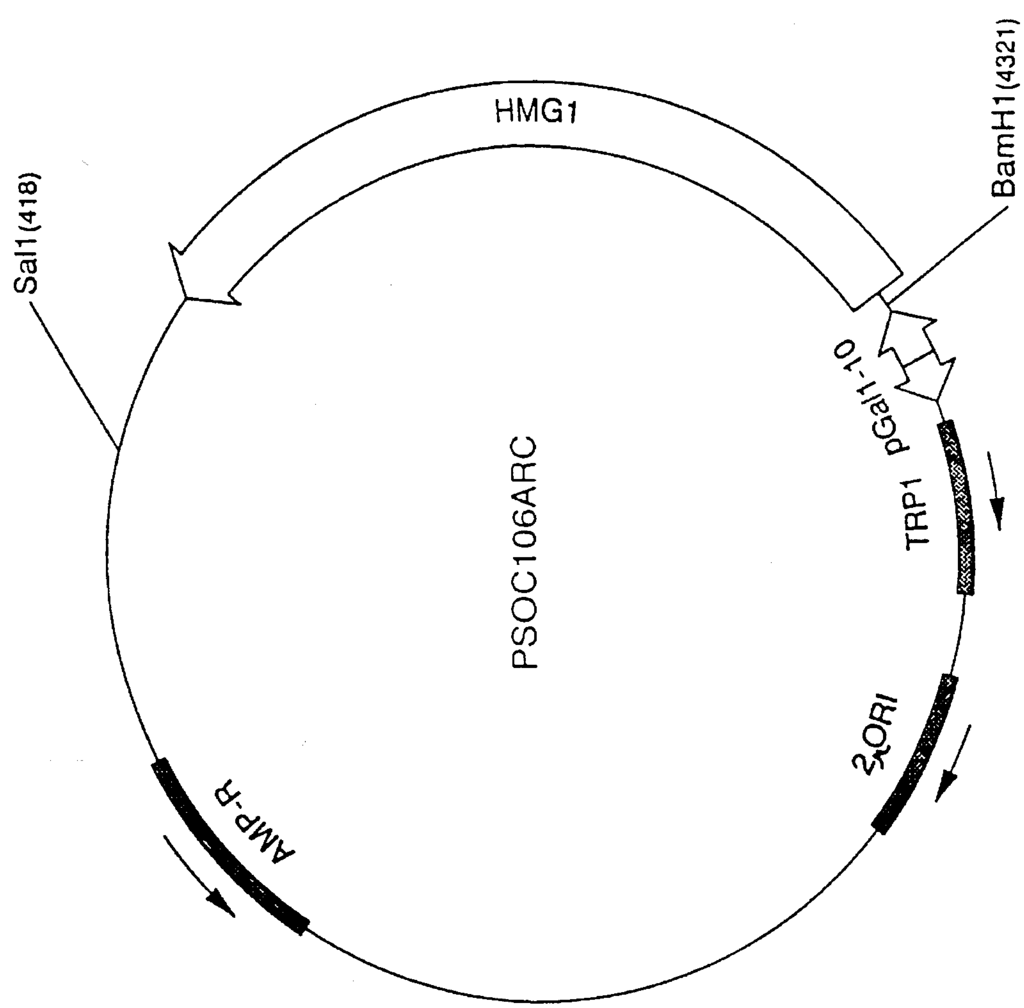

Plasmid pSOC106ARC (See FIG. 4) was constructed to place a coding sequence for intact HMG1 under the control of the GAL 1 portion of a GAL 1-10 promoter.

A 610 base pair Bgl II fragment from pJR59 (about positions 9026–9636), containing the DNA surrounding the beginning of the HMG-CoA reductase coding sequence, was isolated and further restricted with Dde I to provide a DNA fragment (about positions 9151–9636) starting 68 base pairs upstream of the first codon of the HMG-CoA reductase coding sequence.

The Dde I and Bgl II fragments were treated with the Klenow fragment of DNA polymerase to render the ends "blunt." The fragments were then ligated to oligonucleotide linkers, d5'-CCGGATCCGG-3 (SEQ ID NO:9), specifying a Bam HI cleavage site (BRL linkers). The ligated fragments were digested with Bam HI to produce ligateable Bam HI restriction ends, and the resulting 499 base pair fragment containing the start of the HMG-CoA reductase coding sequence was ligated into Bam HI digested pBR322 to form plasmid pSOC104.

The remainder of the HMG-CoA reductase coding sequence was reconstructed downstream of the new 5' Bam HI site by ligating a 1477 base pair Xba I-Sac I DNA fragment of pjR59, which specifies the 5' half of the HMG-CoA reductase coding sequence, and a 2101 base pair Sac I-Sal I fragment of pJR59, which specifies the 3' half of the HMG-CoA reductase coding sequence, into pSOC104 digested with Xba I and Sal I to form plasmid pSOC105 containing a 3903 base pair Bam HI-Sal I restriction fragment having the entire coding sequence for HMG-CoA reductase. This 3903 base pair fragment was ligated into Bam HI-Sal I-restricted pSOC712 (See Example 2) to form plasmid pSOC106ARC.

EXAMPLE 4

Construction of Integrating Plasmid pARC306E

Figure 5:
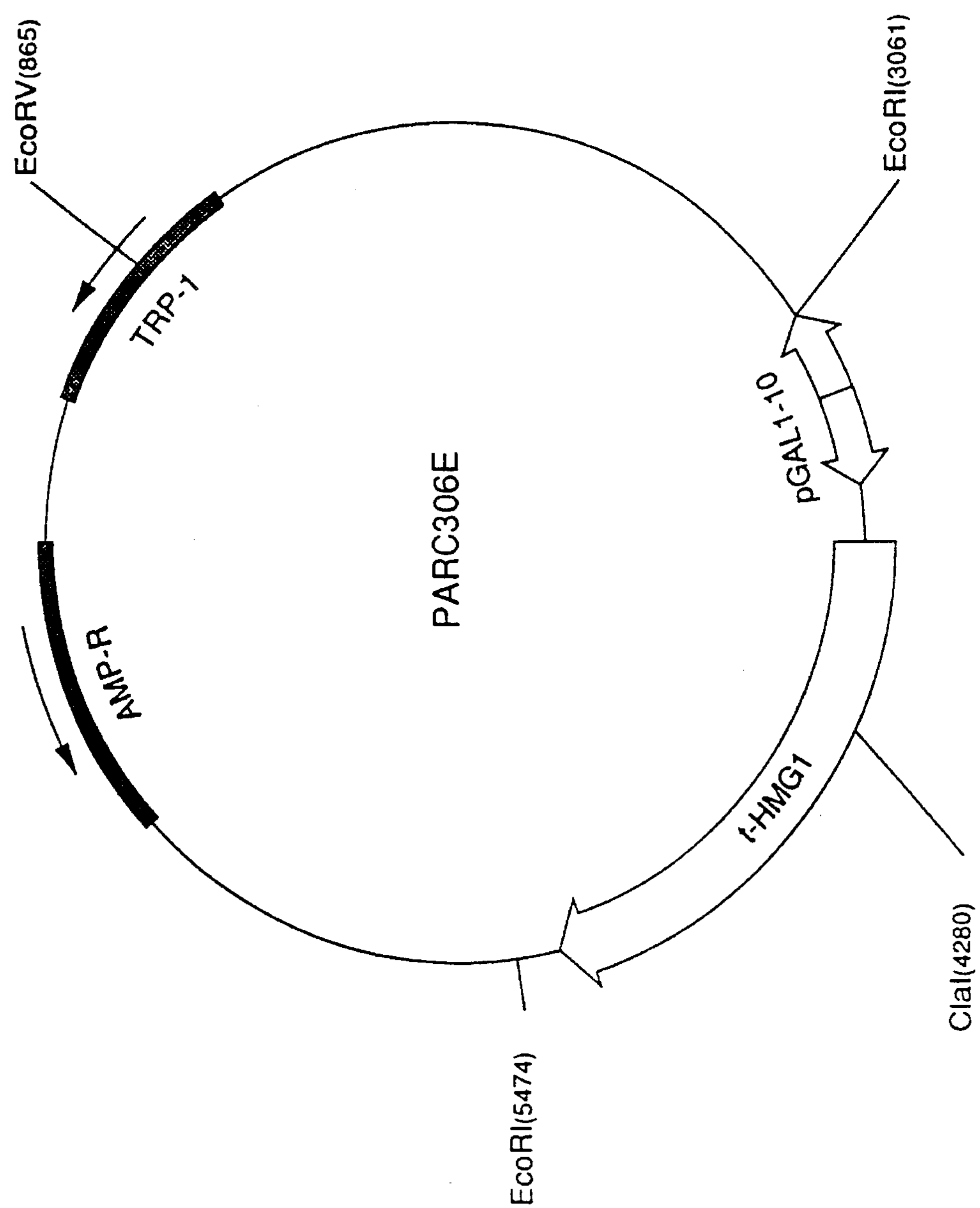

Plasmid pARC306E (See FIG. 5) was constructed to place a coding sequence for truncated HMG1 under control of the GAL 1 portion of a GAL 1-10 promoter.

Plasmid pARC306E contains the *S. cerevisiae* TRP 1 gene and a GAL 1 promoter-driven, truncated HMG-CoA reductase gene housed on an *E. coli* replicon, which specifies ampicillin resistance. There are no *S. cerevisiae* replicators on plasmid pARC306E. Unique restriction sites within both the TRP 1 gene (Eco RV, position 865) and the truncated HMG-CoA reductase gene (Cla I, position 4280) serve as sites for the generation of linear plasmids with DNA homologous to *S. cerevisiae* chromosomal DNA on both sides of the restriction site. Thus, plasmid pARC306E can be incorporated into the chromosome at either site via homologous recombination.

The multiple restriction recognition site of plasmid pUC8, located between the Eco RI and Hind III sites, was replaced by the oligonucleotide:

d5'-AGCTTTCGCGAGCTCGAGATCTAGATATCGATG (SEQ ID NO:10)

3'-AGCGCTCGAGCTCTAGATCTATAGCTACTTAA-5'(SEQ ID NO: 11)

to create plasmid pUC8NL, which has a single restriction site for the nuclease enzyme Cla I.

Plasmid pSOC712 (See Example 2) was digested with Eco RI and the fragments treated with nuclease S1 and bacteriophage T4 DNA polymerase plus deoxynucleotides to remove the overhanging 5' Eco RI restriction ends. These ends were ligated to the oligonucleotide:

d5'-CATCGATG-3' d3'-GTAGCTAC-5' and the fragments treated with Cla I nuclease to produce Cla I restriction ends.

The resulting 3108 base pair Cla I-Cla I fragment, containing the yeast TRP 1 gene and the two-micron replicator, was purified by gel electrophoresis and ligated into pUC8NL, which had been cleaved with Cla I, to create plasmid pARC300A.

A 2031 base pair fragment containing the two-micron replication origin was removed from pARC300A by treatment with nuclease Pst I. The resulting modified plasmid pARC300A was treated with nuclease S1 and bacteriophage T4 DNA polymerase plus deoxynucleotides to remove the Pst I restriction overhangs and with calf intestinal alkaline phosphatase to disallow reclosure of the plasmid. The modified pARC300A plasmid was coligated with the oligonucleotide:

d5'-CATCGATG-3' d3'-GTAGCATC-5' to introduce a Cla I site just downstream (to the 3' end) of the TRP 1 gene to form a plasmid, and then closed to form pARC306B. The TRP 1 gene was separate from yeast replicators, and bounded by Cla I restriction sites.

Plasmid pARC306B was digested with Cla I, purified by polyacrylamide gel electrophoresis and the Cla I-Cla I restriction fragment was introduced into plasmid pUC8, which had been cleaved with nuclease Acc I, to form plasmid pARC306C.

As the integration of exogenous DNA into yeast chromosomes is best carried out using homologous recombination, a dispensable fragment of yeast DNA was desired. This DNA would be used to drive homologous recombination if for some reason, recombination at the TRP 1 or HMG-CoA reductase gens were not utilizable. The DNA chosen for this purpose was the HIS3 gene.

An 1800 pair Bam HI-Bam HI restriction fragment was removed from plasmid YEP6 [Struhl et al., *Proc. Natl. Acad. Sci. USA*, 76:1035 (1979)] and introduced into plasmid pARC306C, which had been cleaved with Bam HI, to create plasmid pARC306D. Plasmid pSOC725 (See Example 2) was digested with Eco RI to yield a GAL 1-10 promoter linked to a truncated HMG-CoA reductase gene, which was then inserted into Eco RI-digested plasmid pARC306D, to form plasmid pARC306E.

EXAMPLE 5

Construction of Integrating Plasmid pARC300D

Figure 6:
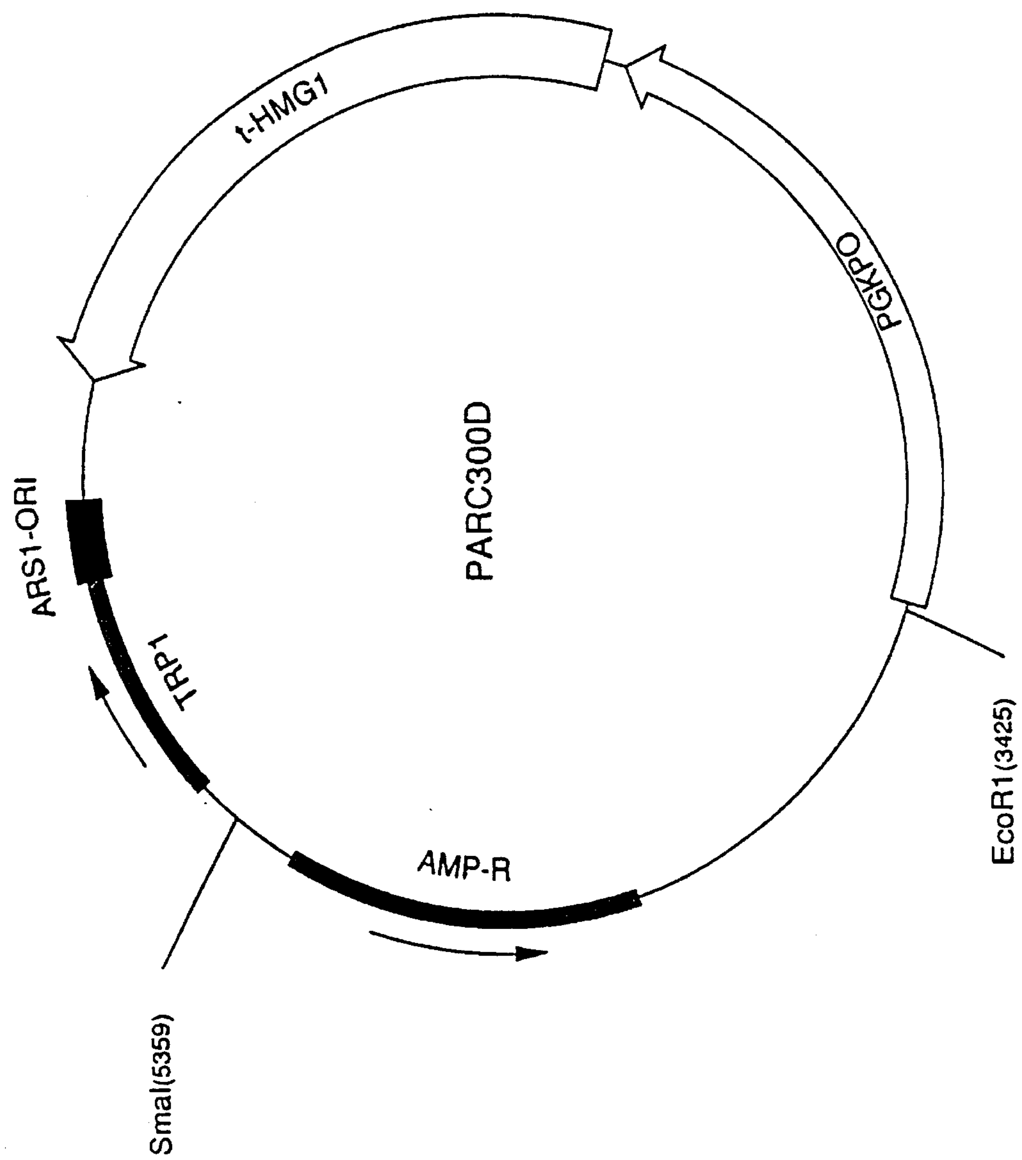

Plasmid pARC300D (See FIG. 6) was constructed to place a coding sequence for a truncated HMG1 gene under the control of a PGK promoter. This plasmid was prepared from intermediate plasmids as follows.

Plasmid pSOC611 was constructed to determine the efficacy of the mouse metallothionine promoter as a transcriptional driver for the truncated HMG-CoA reductase gene in yeast. Construction of pSOC611 began with restriction of plasmid pSOC744 (See Example 2) with Eco RI endonuclease, followed by treatment with Klenow Polymerase I and deoxynucleotide triphosphates to fill in the Eco RI restriction ends. The resulting about 3101 base pair 2-micron- and TRP 1-containing fragment of pSOC744 was ligated to pUC18 which had been cleaved with Hinc II, to form plasmid pSOC517.

Plasmid pSOC517 was then cleaved with Kpn I and Eco RI and the mouse metallothionine promoter was inserted as a Kpn I-Eco RI restriction fragment to form plasmid pSOC518. This promoter region is composed of the Kpn I to Bgl II fragment originally in pJYMMT(e) [Hammer et al., *Journal of Applied Molecular Genetics*, Vol. 1:273 (1982)] as well as a short Bgl II, Eco RI DNA fragment of unknown sequence.

The truncated HMG-CoA reductase gene was added to pSOC518 in two steps. First, the truncated HMG-CoA reductase gene was removed from pSOC725 as a Bam HI restriction fragment. This fragment was then ligated into M13mp7 which had been cleaved with Bam HI. The new M13 derivative formed was designated pSOC610. The truncated HMG-CoA reductase gene was removed from pSOC610 as an Eco RI fragment and inserted into Eco RI-digested plasmid pSOC518. The resulting plasmid was designated pSOC611.

Plasmid pUC8 was partially digested with restriction endonuclease Hae II and religated. Transformants arising from this procedure were screened to find a plasmid missing the Hae II restriction fragment containing the portion of the lac operon which was originally present in plasmid pUC8. This new plasmid was designated pSOC505ARC. Restriction sites for the endonucleases Eco RI, Hind III and Kpn I were introduced into the Nde I site of plasmid pSOC505ARC by ligation of the oligonucleotide:

d5'-TATCGAATTCAAGCTTGGTACCGA-3' (SEQ ID NO:12)

3'-AGCTTAAGTTCGAACCATGGCTAT-5' (SEQ ID NO:13)

into Nde I-digested pSOC505ARC to form plasmid pARC303A.

To form the new multi-cloning site, the normal multi-cloning site present in M13mp18 was altered by ligating the oligonucleotide:

d5'-GATCCAGCTGTGTAC-3' (SEQ ID NO:14)
d3'-GTCGACA-5' into Bam HI-Kpn I digested M13mp18. This resulted in an altered M13 virus, designated pARC303B. This construct lacked both the Kpn I and Sma I sites normally found in the M13mp18 multi-cloning site. The new multi-cloning site was removed as an Eco RI, Hind III restriction fragment from pARC303B, and was ligated into Eco RI, Hind III restricted plasmid pARC303A to form plasmid pARC303C.

In addition to a variation in the normal array of sites included in the multi-cloning site, another smaller multi-cloning site was introduced into the vector, at a point some distance away from the first multi-cloning site to allow for independent manipulation of yeast auxotrophic complementation markers and other features which did not have to be proximal to the promoters and coding sequences which would be inserted in the large multi-cloning site. The new array of restriction sites was introduced by ligation of the oligonucleotide:

d5'-CCCGGGATCGATCACGT-3' (SEQ ID NO:15)
d3'-TGCAGGGCCCTAGCTAG-5' (SEQ ID NO:16)

into pARC303C cleaved with endonuclease Aat II to form plasmid pARC300E, which contained the series of cloning sites, Aat II, Sma I, and Cla I at the former Aat II site.

The yeast TRP 1 gene was isolated as an 820 base pair fragment from pARC306B (See Example 4) with the restriction endonuclease Cla I. The 820 base pair Cla I-Cla I fragment was purified by agarose gel electrophoresis and ligated into plasmid pARC300E, which had been digested with Cla I, to create plasmid pARC300B.

Plasmid pSOC611 was digested with Bam HI and Ssp I to yield a 1667 base pair coding sequence for the truncated HMG-CoA reductase gene which was purified by agarose gel purification. The 1667 base pair fragment was ligated to Bam HI, Hinc II restricted plasmid pARC300B to generate plasmid pARC300C.

A source of an alternate promoter to the GAL 1-10 promoter which has been used to drive transcription of the truncated HMG-CoA reductase gene was desired. Use of the GAL 1-10 promoter requires that the yeast be cultured on galactose, an expensive substrate. In order to achieve high levels of transcription through the truncated HMG-CoA reductase gene during culture, growth in the presence of the much less expensive substrate, glucose, the promoter from the *S. cerevisiae* phosphoglycerate kinase (PGK) gene was isolated. The sequence of the gene is available from the literature, [Hitzeman, et al., *Nucl. Acid Res.*, 10:7791–7808 (1982)].

From the known sequence, an oligonucleotide probe sufficiently complementary to the gene to be used as a hybridization probe was synthesized:

d5'-ATAAAGACATTGTTTTTAGATCTGTTGTAA-3' (SEQ ID NO:17)

This probe was labelled by $T_4$ polynucleotide kinase treatment in the presence of $^{32}$P-ATP, and used to screen a library of bacteriophage λ subclones of the yeast genome, supplied by Maynard Olson (Washington University School of Medicine, Department of Genetics, St. Louis, Mo.). The gene was removed from this clone as an Eco RI-Hind III fragment, and subcloned into M13mp18, forming a new phage mARC127.

To make the PGK promoter useful, the restriction site at the 5', end of the promoter was changed to an Eco RI restriction site, and a Bgl II restriction site was introduced into the DNA fragment to the 3' side of the transcriptional start site. The Bgl II restriction site was introduced by using the oligonucleotide:

d5'-ATAAAGACATTGTTTTTAGATCTGTTGTAA-3' (SEQ ID NO:17), to mutagenize mARC127 according to the procedure of Kunkel et al., *Proc. Natl. Acad. Sci. USA*, 82:4778 (1985). This resulted in the M13 phage designated mARC128.

The Hind III site beyond the 5' end of the promoter region was converted to an Eco RI site by cutting mARC128 with nuclease Hind III, treating with the Klenow fragment of DNA polymerase and the four deoxrynucleotide triphosphates, followed by ligation in the presence of the oligonucleotide:

d5'-GGAATTCC-3', which specifies an Eco RI site. The resulting M13 derivative was designated pARC306L.

Plasmid pARC306L was digested with Eco RI and Bgl II and a 1500 base pair fragment containing the PGK promoter, was purified by agarose gel electrophoresis and ligated into pARC300C, which had been restricted with Eco RI and Bam HI, to produce plasmid pARC300D.

EXAMPLE 6

Construction of Integrating Plasmids pARC300S and DARC300T

Figure 7:
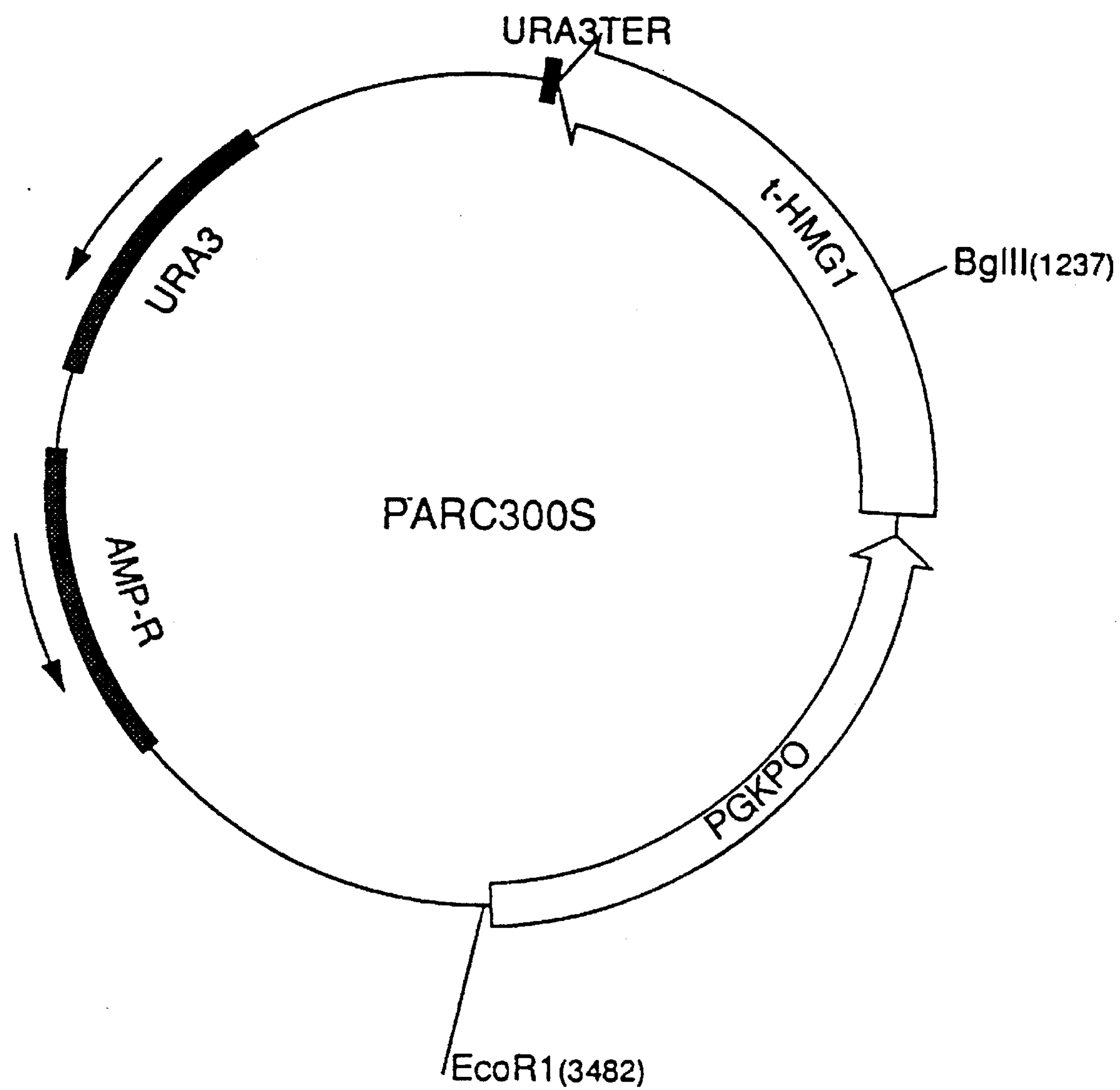
Figure 8:
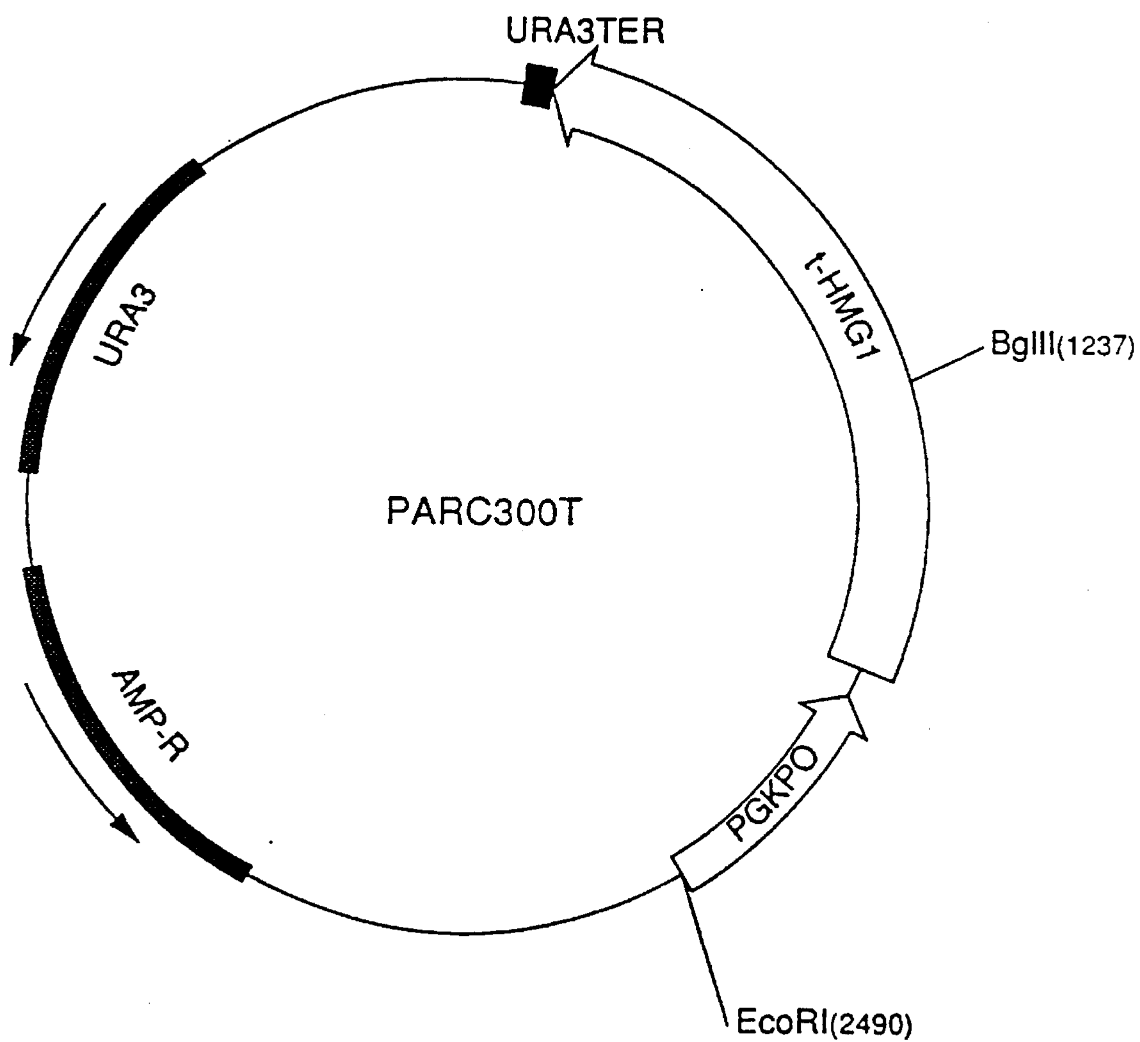

Plasmids pARC300S (See FIG. 7) and pARC300T (See FIG. 8) were constructed to incorporate a URA 3 selectable marker into an integrating vector, in which a coding sequence for a truncated HMG1 gene was under the control of a PGK promoter.

The only difference between plasmid pARC300S and pARC300T is the length of the PGK promoter driving transcription of the truncated reductase coding sequence. A unique Eco RV restriction site found within the URA 3 gene allows the plasmids to be linearized and integrated via homologous recombination into the chromosomal URA 3 gene.

The URA 3 gene from plasmid YEP24 (Botstein, et al., Gene, 8:17–24 (1979)) was removed as an 1127 base pair Eco RI-Sma I ended restriction fragment and ligated into plasmid pUC19, cut with Eco RI and Sma I to form a new plasmid LpARCLH550. An 1141 base pair Hind III ended restriction fragment was removed from LpARCLH550 and ligated into Hind III-cleaved pUC18 to form plasmid LpARCLH553a. An 1108 base pair Sma I-Hind III restriction fragment was removed from LpARCLH553a and inserted into Sma I-Hind III cleaved M13mp19 nucleic acid to create a new phage nucleic acid pARC306K. The unique PstI site within the URA 3 gene was eliminated by mutagenesis with the oligonucleotide:

d5'GATTTATCTTCGTTTCCTGCAAGTTTTTGTTC-3' (SEQ ID NO:18), using the method of Kunkel, L. M.; et al., *Proc. Nat'l. Acad. Sci. USA*, 82:4778 (1985), to form plasmid pARC300Z.

Plasmid pARC300Z was cut with Hind III, the ends filled in with the Klenow fragment of DNA polymerase and deoxynucleotide triphosphates, and the modified pARC300Z ligated with oligonucleotide d5'-CCCCGGGG-3', which specified a Sma I restriction site. This new M13 derivative, which contains the URA 3 gene on a Sma I restriction fragment, was named plasmid pARC300Y.

Plasmid pARC304A was constructed to provide a source of a modified URA 3 transcription terminator fragment which could then be introduced at the 3' end of the coding sequence region in a yeast integrating transformation vector. The transcription terminator would function to improve mRNA stability in species transformed with integrating vectors containing coding sequences either lacking the terminator or having only weak terminator sequences. Improved mRNA stability could mean increased activity of the protein encoded by the coding sequence region. The terminator chosen was a region of the *S. cerevisiae* URA 3, which functions as a terminator, [Yarger et al., *Molecular and Cellular Biology,* 6:1095 (1986)]. The terminator sequence was constructed using 4 synthetic oligomers:

d5'-AGCTTCGAAGAACGAAGGAAGGAGCACA-GACTTAG-3' (SEQ ID NO:19)

d5'-ATTGGTATATATACGCATATTGCGGC-CGCGGTAC-3' (SEQ ID NO:20)

d5'-CGCGGCCGCAATATGCGTATATATAC-3' (SEQ ID NO:21)

d5'-CAATCTAAGTCTGTGCTCCTTCCTTCGT-TCTTCGA-3' (SEQ ID NO:22)

These oligomers were designed to provide Mind III and Kpn I restriction ends, respectively. The modified URA 3 transcription terminator was assembled by ligating all four oligomers to each other and digesting the ligation product with Mind III and Kpn I to produce ligatable Mind III-Kpn I restriction ends. The 67 base pair fragment was isolated on a polyacrylamide gel, purified by electroeluting the DNA from the gel fragment, and then ligated into Mind III-Kpn I restricted pUC118, (ATCC 37462). This construction created a new plasmid designated pARC304A.

A 67 base pair Mind III-Kpn I fragment containing a URA 3 transcription terminator was isolated from plasmid pARC304A and ligated into Mind III-Kpn I restricted pARC300E to form plasmid pARC300M. A truncated HMG-CoA reductase coding sequence was isolated as a 1667 base pair Bam HI-Ssp I fragment from pSOC611, (See Example 5) purified by agarose gel electrophoresis, and ligated to pARC300M, which had been restricted with Bam HI and Minc II, to form plasmid pARC300R.

URA 3 complementing gene was removed from plasmid pARC300Y as an Xma I restriction fragment, and ligated into the Xma I site of pARC300R to create plasmid pARC300U.

One other change in the restriction sites available on the DNA specifying the PGK promoter was made. The minimum DNA required to specify full PGK promoter activity has been determined, [Stanway, *Nucleic Acids Research,* 15:6855–6873 (1987)]. A new Eco RI site was added to the DNA specifying the PGK promoter at a region just past the minimal 5' required DNA. The site was added by utilizing the oligonucleotide:

d5'-CTTTATGAGGGTAACATGAATTCAAGAAGG-3' (SEQ ID NO:23), to mutagenize mARC1228 by the method of Kunkel et al., *Proc. Natl, Acad. Sci. USA,* 82:4778 (1985). This new M13 derivative was designated pARC306M.

A 1500 base pair phosphoglycerate kinase promoter (PGK) was removed from plasmid pARC306L (See Example 5) using Eco RI and Bgl II restriction enzymes. The PGK promoter fragment was purified by agarose gel electrophoresis and ligated to Eco RI and Bam HI restricted pARC300U, to form plasmid pARC300S.

A shortened PGK promoter (555 base pair fragment) was isolated from Eco RI and Bgl II restricted plasmid pARC306M and inserted into Eco RI-Bam HI digested plasmid pARC300U to form plasmid pARC300T.

The only difference between plasmid pARC300S and plasmid pARC300T is the length of the PGK promoter driving transcription of the truncated reductase coding sequence. A unique Eco RV restriction site found within the URA 3 gene allows the plasmids to be linearized and integrated via homologous recombination into the chromosomal URA 3 gene.

EXAMPLE 7

Figure 9:
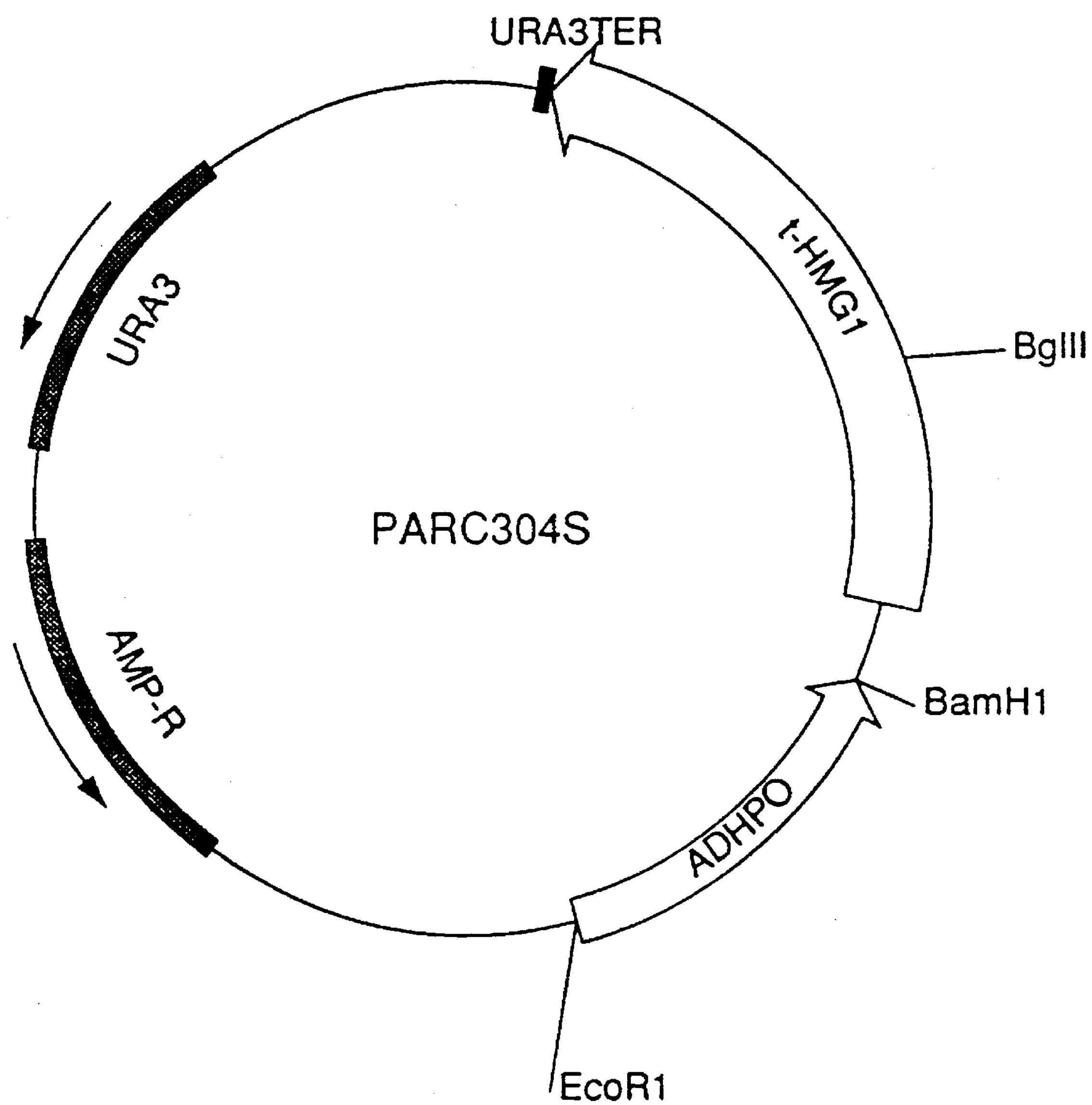

Construction of Plasmid pARC304S Plasmid pARC304S (see FIG. 9) was constructed to place the coding sequence of a truncated HMG1 gene under the control of an ADH promoter.

Plasmid pBR322 was digested with Eco RI and Bam HI to yield a fragment containing the ADH1 promoter. The ADH1-containing fragment was ligated into plasmid pARC300U (See Example 6), which had been cut with Eco RI and Bam HI, to form pARC304S.

Plasmid pARC304S was deposited pursuant to the Budapest Treaty requirements with the American Type Culture Collection (ATCC) at 12301 Parklawn Drive, Rockville, Md. 20852 U.S.A. on Nov. 9, 1990 and was assigned Accession No. ATCC40916.

EXAMPLE 8

Generation of Mutant *S. cerevisiae* ATC0402mu

Mutant ATC0402mu was generated to have the GAL, a, and trp1 phenotype as well as having defects in the expression of zymosterol-24-methyltransferase and ergosta-5,7,24(28)-trienol-22-dehydrogenase enzymes. These enzymes are respectively the erg6 and erg5 gene products of *S. cerevisiae.*

An erg6 deficient mutant *S. cerevisiae,* M61012B, obtained from the Yeast Genetic Stock Center (Univ. of California, Berkeley, Calif.), was crossed with an erg5 deficient mutant *S. cerevisiae* (obtained as a gift from Dr. Leo Parks, North Carolina State Univ., Raleigh, N.C.) to produce an erg6-erg5 double mutant, ATC0403mu.

ATC0403mu was then crossed with wild-type *S. cerevisiae,* DBY745 (Yeast Genetic Stock Center) to produce mutant ATC0402mu.

Mutant ATC0402mu was deposited pursuant to the Budapest Treaty Requirements with the American Type Culture Collection (ATCC) at 12301 Parklawn Drive, Rockville Md. 20852 U.S.A. on Nov. 9, 1990, and was assigned Accession No. ATCC 74027.

EXAMPLE 9

Generation of Transformed Mutants ATC1500cp, ATC1502, ATC1503, ATC1551 and ATC2401

Several mutants were generated from the transformation of ATC0402mu using the method of Example 1, with various expression systems (plasmids) containing HMG-CoA reductase coding sequences under the transcriptional control of various promoters. The introduction into ATC0402mu of plasmid pSOC106ARC, constructed according to the method of Example 3, created ATC1503.

The introduction into ATC0402mu of plasmid pSOC725ARC, constructed according to the method of Example 2, created ATC2401mu.

The introduction into ATCO402mu of plasmid pARC306E, constructed according to the method of Example 4, created ATC1502.

The introduction into ATC0402mu of plasmid pARC300D, constructed according to the method of Example 5, created ATC1500cp.

The creation of strain ATC1551 required the generation of a ura3 derivative of strain ATC1500cp, which has no auxotrophic markers. The ura3 derivative was created by transforming ATC1500cp with a mutagenic oligonucleotide using the method of Moerschell et al. [*Proc. Natl. Acad. Sci. USA,* 85:524–528 (1988)]. The sequence of the mutagenic oligonucleotide used is:

5'-GCCAAGTAGTTTTTACTCTTCAAGACA-GATAATTTGCTGACA-3' (SEQ ID NO:24 )

Mutated yeast cells were selected by their resistance to 5'-fluoro-orotic acid (5-FOA), as described in Ausubel et al., (eds.), *Current Protocols in Molecular Biology,* John Wiley and Sons, New York, (1989), and screened for their inability to grow in the absence of uracil. The resulting ura3 strain was designated ATC0315rc. Strain ATC0315rc was then transformed with plasmid pARC304S, constructed according to the method of Example 7, to create strain ATC1551.

Transformation of strain ATC0315rc with plasmid pARC304S of the present invention resulted in the greatest degree of sterol accumulation. Further, the growth of a transformed ATC0315rc mutant under conditions of restricted aeration as compared to usual culture conditions, resulted in an increased accumulation of squalene relative to other sterols as well as an increase in the total accumulation of squalene and total sterols.

Mutant ATC0315rc was deposited pursuant to the Budapest Treaty Requirements with the American Type Culture Collection (ATCC) at 12301 Parklawn Drive, Rockville, Md. 20852 U.S.A. on Sep. 16, 1991, and was assigned Accession No. ATCC 74090.

EXAMPLE 10

Generation of Mutant *S. cerevisiae* ATC6118, ATC05O1 and ATC6119

Mutants were obtained using an inducible "TY1-neo" transposon as the mutagenic agent, [Boeke, et al., *Science,* 239:280–282 (1989)].

Wild type *S. cerevisiae* JB516 was transformed with plasmid pJEF1105 [Boeke et al., *Science,* 239:280–282 (1989)], containing an inducible GAL:TY1neo expression cassette, and plasmid pCGS286, containing a GAL:lacZ control. The transformed yeast were then spread onto petri dishes containing two kinds of Xgal chromogenic indicator dye: synthetic dextrose (SD) agar media minus uracil and synthetic galactose (SG) agar media minus uracil. Yeast transformed with plasmid pJEF1105 appeared normal on dextrose but smaller than untransformed control yeast on galactose media.

The stability of plasmid pJEF1105 was confirmed by shuttling into *E. coli* for propagation and restriction analysis.

Once plasmid pJEF1105-transformed yeasts were shown to be competent, the pJEF1105 transformants were placed on SG-minus uracil agar at a density of no more than 1000 transformants per petri plate. The plates were incubated at 22° C. for five days, during which the mutagenic transposition of the plasmid borne TY1-neo occurred. The transformants were then replica plated onto another SG-minus uracil plate and incubated another five days. Those colonies that survived were replica plated onto YEPD agar plates containing 100 units/ml of nystatin to select for sterol production and 100 units/ml of G418 (a neomycin analog) to select for the "neo" phenotype. Transformants that were both nystatin and G418 resistant were evaluated for sterol content and distribution using gas chromatographic and mass spectrographic analysis and then classified as to the specific sterol biosynthetic step affected by the mutation.

A yeast deficient in the enzyme episterol-5-dehydrogenase (the erg3 gene product) was isolated and designated ATC6118.

A yeast deficient in the enzyme zymosterol-24-methyltransferase (erg6) was isolated from plasmid pJEF1105 mutated yeast DBY745 (Yeast Genetic Stock Center) and designated ATC0501.

ATC0501 was crossed with ATC6118 to produce an erg3-erg6 double mutant designated ATC6119.

EXAMPLE 11

Generation of Transformed Mutant S. cerevisiae ATC2100, ATC2104 and ATC2109

Following the method of Example 1, the introduction into ATC6119 of plasmids pARC300S and pARC300T, constructed according to the method of Example 6, created ATC2100 and ATC2104 respectively, whereas the introduction into ATC6118 of plasmid pARC300S created ATC2109.

EXAMPLE 12

Generation of Mutant S. cerevisiae ATC4124

ATC4124 (Yeast Genetic Stock Centers) was generated by crossing ATC0403mu with YNN281 (Yeast Genetic Stock Centers) and selecting for the desired mutation. The resulting segregants were then backcrossed twice with YNN281.

Resulting ATC4124 had a defect in the expression of cholesta-5,7,24(28)-trienol-22-dehydrogenase (the erg5 gene product).

EXAMPLE 13

Generation of Transformed Mutant S. cerevisiae ATC2107 and ATC2108

Following the method of Example 1, introduction into ATC4124 of plasmid pARC306E, constructed according to the method of Example 4, created ATC2107 and ATC2108.

EXAMPLE 14

HMG-CoA Reductase Activity in Mutant and Transformed Yeast

HMG-CoA reductase activity was measured in non-transformed and transformed erg5-erg6 mutant yeasts.

About 0.2 ml of 50 mM potassium phosphate buffer, pH 6.8, containing 125 mM sucrose, 20 mM EDTA and 100 mM KCl was combined with 10 mM DTT (freshly made), 1 mM NADPH, enzyme preparation and water to make an enzyme solution of about 0.475 ml final volume. The enzyme solution was preincubated at 37° C. for 20 minutes and the incubation reaction initiated with the addition of 100 μM $^{14}$C-HMG-CoA (60,000 dpm in 0,025 ml). After five minutes, the reaction was stopped by the addition of 50 μl of HCl (1:1) and further incubation at 37° C. for 30 minutes to lactonize the product. The product, mevalonolactone, was separated from HMG on an anion exchanger AGI-X8 (Bio-Rad) and the radioactivity associated with the product was counted in a scintillation counter. The results are shown in Table 5, below. The copy number of an added structural gene encoding a polypeptide having HMG-CoA reductase activity was estimated using standard procedures well known to those of skill in the transformation art.

TABLE 5

| Mutant | Estimated Copy # of Added Structural Gene | Specific Activity HMG-CoA Reductase (mmols/min/mg dry wt) |
|---|---|---|
| Non-transformed | 0 | 0.52 |
| ATC0402mu | | |
| Transformed | | |
| ATC1503 | 1,2 | 0.69 |
| ATC1500cp | 5,6 | 1.33 |
| ATC1512 | 8,9 | 1.01 |

EXAMPLE 15

Squalene and Sterol Accumulation in Yeast

The accumulation of squalene and specific sterols was determined in non-transformed and transformed mutant yeast cultures.

Fifty to one hundred mg of lyophilized yeast cells were extracted/saponified in 10 ml of an ethanol/water (2:1) solution containing 20 percent (w/v) KOH for two hours at 80° C. Extracts were partially neutralized with 10 ml 1N HCl and extracted twice with 15 ml n-heptane. The sterol-containing heptane fractions were evaporated to dryness under a stream of $N_2$ and resuspended to an appropriate volume with n-heptane containing an internal standard (5-alpha-cholestane).

The resuspended samples were analyzed for sterol accumulation by capillary GC with flame ionization detection.

Table 6 contains summary data for non-transformed (control) and transformed mutants having a single defect (erg3, erg5) in the expression of sterol biosynthetic pathway enzymes.

Table 7 contains summary data for non-transformed (control) and transformed mutants having double defects (erg3-erg6, erg5-erg6) in the expression of sterol biosynthetic pathway enzymes.

In both Table 6 and Table 7, the transformants were all made by transforming the control mutant having the same erg mutation.

Sterol levels are expressed as a percent of the dry biomass.

TABLE 6

ERG3 Mutants

| Sterol | Percent of Biomass: Non-transformed ATC6118 | Percent of Biomass: Transformed ATC2109 |
|---|---|---|
| a. Squalene | N.D.* | 0.26 |
| b. ergosta-8,22-dienol | 0.31 | 1.08 |
| c. ergosta-7,22-dienol | 0.66 | 1.64 |
| d. ergosta-8-enol | 0.27 | 0.42 |
| e. ergosta-7-enol | 0.63 | 0.72 |

ERG5 Mutants

| Sterol | Percent of Biomass: Non-transformed ATC4124 | Transformed ATC2107 | Transformed ATC2108 |
|---|---|---|---|
| a. Squalene | N.D. | 1.10 | 0.49 |
| b. Zymosterol | 0.05 | 0.25 | 0.25 |
| c. ergosta-5,7,24(28)-trienol and ergosta-5,7-dienol | 0.17 | 1.75 | 1.19 |

*Not Detectable

TABLE 7

ERG3–ERG6 Mutants

| Sterol | Percent of Biomass: Non-transformed ATC6119 | Transformed ATC2100 | Transformed ATC2104 |
|---|---|---|---|
| a. Squalene | N.D*** | 0.13 | 0.98 |
| b. Zymosterol | 0.21 | 1.10 | 1.80 |
| c. Cholesta-7,24-dienol | 0.53 | 1.10 | 1.50 |

ERG5–ERG6 Mutants

| Sterol | Non-transformed ATC0402mu (n = 4) | Transformed ATC1503 (n = 2) | Transformed ATC2401mu (n = 4) | Transformed ATC1502 (n = 2) | Transformed ATC1500cp (n = 1) | Transformed ATC1551 (n = 1) |
|---|---|---|---|---|---|---|
| a. Squalene | 0.026 | 0.336 | 0.947 | 1.078 | 0.27 | 2.992 |
| b. Zymosterol | 1.107 | 1.358 | 1.125 | 2.065 | 3.746 | 5.125 |
| c. C5,7,24* | 1.542 | 0.956 | 1.064 | 1.354 | 1.868 | 2.372 |
| d. C7,24** | 0.213 | 0.362 | 0.250 | 0.408 | 0.564 | 0.775 |

(Percent of Biomass)

*C5,7,24 is cholesta-5,7,24-trienol
**C7,24 is cholesta-7,24-dienol
***Not Detectable
n = number of observations The above data illustrate that transformation of mutants having a single defect in the expression of sterol biosynthetic pathway enzymes resulted in an increased accumulation of squalene and specific sterols (See Table 6).

Relative to a non-transformed erg3 mutant, erg3 mutants transformed with a plasmid vector useful in the present invention overaccumulated squalene, ergosta-8,22-dienol, ergosta-7,22-dienol, ergosta-8-enol and ergosta-7-enol.

Relative to a non-transformed erg5 mutant, erg5 mutants transformed with a plasmid vector useful in the present invention overaccumulated squalene, zymosterol, and a mixture of ergosta-5,7,24(28)-trienol and ergosta-5,7-dienol.

Similarly, transformation of mutants having double defects in the sterol biosynthetic pathway enzymes led to the overaccumulation of squalene and specific sterols.

Relative to a non-transformed erg3-erg6 mutant, erg3-erg6 mutants transformed with a plasmid vector useful in the present invention overaccumulated squalene, zymosterol and cholesta-7,24-dienol.

Relative to a non-transformed erg5-erg6 mutant, erg5-erg6 double mutants transformed with a plasmid vector useful in the present invention overaccumulated squalene, zymosterol, cholesta-5,7,24-trienol and cholesta-7,24-dienol.

The greatest increases in squalene and specific sterol accumulation are seen when erg5-erg6 mutant ATC0315rc is transformed with plasmid vector pARC304S (mutant ATC1551), as described in Example 9. Further, the data show that species ATC0402mu, the grandparent strain of mutant ATC0315rc, has elevated levels of sterols relative to either an erg5 or an erg6 single mutant (see Table 6).

EXAMPLE 16

Induction of Squalene Accumulation in Yeast Transformant ATC1551

It is generally known that restricted aeration induces squalene accumulation at the expense of sterols in yeast cultures. This occurs because oxygen is required for the enzymatic conversion of squalene to squalene monoepoxide, which in turn is converted into lanosterol and other yeast sterols.

To determine if high levels of squalene accumulation could be induced in transformants, cultures of ATC1551 were grown under varying degrees of aeration by varying the volume (and hence the surface-to-volume ratio) of growth medium in shake-flask cultures and assaying squalene and total sterol at one day intervals over a period of four days.

Triplicate 250 ml baffled shake-flasks respectively containing 50, 100, 150 and 200 ml of YEP/2 percent glucose growth medium were inoculated with two ml of a 24 hour liquid culture of ATC1551 grown on a rotary shaker (200 rpm) at 30° C. Fifty ml culture aliquots were harvested by centrifugation after one, two, three and four days growth under the aforementioned conditions and lyophilized overnight.

To insure efficient squalene extraction, approximately 100 mg of each lyophilized sample was agitated for 10 minutes in 15 ml conical tubes containing a suitable quantity of glass beads and a small amount of water. The disrupted cell material was then extracted three successive times with 10 ml of 100 percent ethanol with vigorous agitation for one hour at 80° C. The combined ethanol extracts were reduced to dryness under a stream of nitrogen and redissolved in two ml of heptane containing 5α-cholestane as the internal standard. GC analyses of squalene were conducted as previously described.

For total sterol analyses, the same samples were reduced under a stream of nitrogen and saponified in 5 ml of 95 percent ethanol/water solution containing 0.3M KOH for one hour at 80° C. An equivalent volume of water was added and the samples were twice extracted with 10 ml aliquots of heptane. The heptane extracts were combined, reduced to a suitable volume and analyzed by GC.

The results are shown in Table 8 (data averaged from triplicate cultures and expressed as percent of dry biomass).

TABLE 8

| | Growth Medium Volume | | | |
|---|---|---|---|---|
| Time to Harvest | 50 ml | 100 ml | 150 ml | 200 ml |
| | Percent of Dry Biomass | | | |
| Day 1 | | | | |
| squalene | 4.25 | 5.40 | 3.61 | 2.63 |
| total sterol | 9.40 | 9.52 | 6.81 | 5.46 |
| Day 2 | | | | |
| squalene | 4.78 | 6.43 | 11.89 | 8.32 |
| total sterol | 8.29 | 6.44 | 3.72 | 2.98 |
| Day 3 | | | | |
| squalene | 4.75 | 8.82 | 13.54 | 13.38 |
| total sterol | 7.96 | 7.65 | 4.36 | 4.19 |
| Day 4 | | | | |
| squalene | 4.03 | 7.08 | 15.99 | 14.72 |
| total sterol | 7.09 | 8.62 | 5.10 | 3.39 |

The data show that in transformed, erg5-erg6 mutants, squalene is preferentially accumulated as compared to total sterol by restricting the level of aeration as compared to usual culture conditions (50 mls of growth medium), particularly after more than about one day of culture. The data also show that restricting the level of aeration (lowering the surface-to-volume ratio) also increases the sum total of squalene and total sterol accumulation, after more than about two days of culure.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A method of increasing squalene, zymosterol, cholesta-7,24-dienol and cholesta-5,7,24-trienol accumulation in mutant yeast comprising increasing the expression level of a structural gene encoding a polypeptide having HMG-CoA reductase activity in a mutant yeast having defects in the expression of zymosterol-24-methyltransferase and ergosta-5,7,24(28)-trienol-22-dehydrogenase; and growing said mutant yeast under suitable culture conditions for a period of time sufficient for said accumulation to occur.

2. The method according to claim 1 wherein said encoded polypeptide is an active, truncated HMG-CoA reductase enzyme.

3. The method according to claim 2 wherein said encoded polypeptide is *S. cerevisiae* HMG-CoA reductase 1.

4. The method according to claim 2 wherein said encoded polypeptide is hamster HMG-CoA reductase.

5. The method according to claim 1 wherein the yeast is of the species *S. cerevisiae.*

6. The method according to claim 1 wherein squalene is accumulated relative to said zymosterol, cholesta-7,24-dienol and cholesta-5,7,24-trienol by culturing said yeast under conditions of restricted aeration.

7. The method according to claim 1 wherein the expression level is increased by increasing the copy number of a structural gene encoding a polypeptide having HMG-CoA reductase activity.

8. The method according to claim 7 wherein the copy number is increased by transforming said yeast with a recombinant DNA molecule comprising a vector operatively linked to an exogenous DNA segment that encodes a polypeptide having HMG-CoA reductase activity, and a promoter suitable for driving the expression of said polypeptide in said yeast.

9. The method according to claim 8 wherein the promoter is subject to inducible regulation by factors extrinsic to said yeast.

10. The method according to claim 9 wherein the promoter is selected from the group consisting of the GAL 1, GAL 10 and GAL 1–10 promoters.

11. The method according to claim 8 wherein the promoter is subject to inducible regulation by factors intrinsic to said yeast.

12. The method according to claim 11 wherein the promoter is the PGK or ADH promoter.

13. The method according to claim 8 wherein the promoter and the exogenous DNA segment are integrated into the chromosomal DNA of said yeast.

14. The method according to claim 8 wherein said encoded polypeptide is an active, truncated HMG-CoA reductase enzyme.

15. A mutant *S. cerevisiae* having defects in the expression of zymosterol-24-methyltransferase and ergosta-5,7,24(28)-trienol-22-dehydrogenase enzymes, which mutant species is designated ATC0402mu.

16. A mutant of *S. cerevisiae* having single or double defects in the expression of enzymes that catalyze the conversion of squalene to ergosterol transformed with a recombinant DNA molecule comprising a vector operatively linked to an exogenous DNA segment that encodes an HMG-CoA reductase enzyme and a promoter suitable for driving the expression of said reductase in said yeast.

17. The mutant according to claim 16 wherein the mutant is selected from the group consisting of mutants ATC0315rc, ATC1500cp, ATC1502, ATC1503, ATC1551, ATC2100, ATC2104, ACT2107, ACT2108, ATC2109 and ATC2401.

18. A recombinant DNA molecule designated plasmid pARC304S.

19. A recombinant DNA molecule designated plasmid pARC300S.

20. A recombinant DNA molecule designated plasmid pARC300T.

21. A recombinant DNA molecule designated plasmid pARC300D.

22. A recombinant DNA molecule designated plasmid pARC306E.

23. A recombinant DNA molecule designated plasmid pSOC106ARC.

24. A recombinant DNA molecule designated plasmid pSOC725ARC.

25. A method of increasing squalene, ergosta-8,22-dienol, ergosta-7,22-dienol, ergosta-8-enol, and ergosta-7-enol accumulation in mutant yeast of the species *S. cerevisiae* comprising transforming a mutant *S. cerevisiae* having a defect in the expression of episterol-5-dehydrogenase with a recombinant DNA molecule comprising a vector operatively linked to an exogenous DNA segment that encodes a polypeptide that is an active, truncated HMG-CoA reductase enzyme, and a promoter suitable for driving the expression of said reductase in said mutant yeast to form transformed mutant yeast; and growing said transformed mutant yeast under suitable culture conditions for a period of time sufficient for said accumulation to occur.

26. A method of increasing squalene, zymosterol and cholesta-7,24-dienol accumulation in mutant yeast of the species *S. cerevisiae* comprising transforming a mutant *S. cerevisiae* having a defect in the expression of zymosterol-24-methyltransferase and episterol-5-dehydrogenase with a recombinant DNA molecule comprising a vector operatively linked to an exogenous DNA segment that encodes a polypeptide that is an active, truncated HMG-CoA reductase enzyme, and a promoter suitable for driving the expression of said reductase in said yeast to form transformed mutant yeast; and growing said transformed mutant yeast under suitable culture conditions for a period of time sufficient for said accumulation to occur.

27. A method of increasing squalene, zymosterol, ergosta-5,7,24(28)-trienol and ergosta-5,7-dienol accumulation in mutant yeast of the species *S. cerevisiae* comprising transforming a mutant *S. cerevisiae* having a defect in the expression of ergosta-5,7,24(28)-trienol-22-dehydrogenase with a recombinant DNA molecule comprising a vector operatively linked to an exogenous DNA segment that encodes a polypeptide that is an active, truncated HMG-CoA reductase enzyme, and a promoter suitable for driving the expression of said reductase enzyme, and a promoter suitable for driving the expression of said reductase in said mutant yeast to form transformed mutant yeast; and growing said transformed mutant yeast under suitable culture conditions for a period of time sufficient for said accumulation to occur.

28. The method according to claim 25 wherein the recombinant DNA molecule is selected from the group of plasmid vectors consisting of plasmids pSOC725ARC, pSOC106ARC, pARC300D, pARC306E, pARC300S, pARC300T and pARC304S.

29. The method according to claim 26 wherein the recombinant DNA molecule is selected from the group of plasmid vectors consisting of plasmids pSOC725ARC, pSOC106ARC, pARC300D, pARC306E, pARC300S, pARC300T and pARC304S.

30. The method according to claim 27 wherein the recombinant DNA molecule is selected from the group of plasmid vectors consisting of plasmids pSOC725ARC, pSOC106ARC, pARC300D, pARC306E, pARC300S, pARC300T and pARC304S.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 3360 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 121..3282

( x i ) SEQUENCE DESCRIPTION: SEQ ID NO:1:

```
TTTATTAACT TATTTTTTTC TTCTTTCTAC CCAATTCTAG TCAGGAAAAG ACTAAGGGCT     60

GGAACATAGT GTATCATTGT CTAATTGTTG ATACAAAGTA GATAAATACA TAAAACAAGC    120

ATG CCG CCG CTA TTC AAG GGA CTG AAA CAG ATG GCA AAG CCA ATT GCC      168
Met Pro Pro Leu Phe Lys Gly Leu Lys Gln Met Ala Lys Pro Ile Ala
1               5                   10                  15

TAT GTT TCA AGA TTT TCG GCG AAA CGA CCA ATT CAT ATA ATA CTT TTT      216
Tyr Val Ser Arg Phe Ser Ala Lys Arg Pro Ile His Ile Ile Leu Phe
            20                  25                  30

TCT CTA ATC ATA TCC GCA TTC GCT TAT CTA TCC GTC ATT CAG TAT TAC      264
Ser Leu Ile Ile Ser Ala Phe Ala Tyr Leu Ser Val Ile Gln Tyr Tyr
        35                  40                  45

TTC AAT GGT TGG CAA CTA GAT TCA AAT AGT GTT TTT GAA ACT GCT CCA      312
Phe Asn Gly Trp Gln Leu Asp Ser Asn Ser Val Phe Glu Thr Ala Pro
    50                  55                  60

AAT AAA GAC TCC AAC ACT CTA TTT CAA GAA TGT TCC CAT TAC TAC AGA      360
Asn Lys Asp Ser Asn Thr Leu Phe Gln Glu Cys Ser His Tyr Tyr Arg
65                  70                  75                  80

GAT TCC TCT CTA GAT GGT TGG GTA TCA ATC ACC GCG CAT GAA GCT AGT      408
Asp Ser Ser Leu Asp Gly Trp Val Ser Ile Thr Ala His Glu Ala Ser
                85                  90                  95

GAG TTA CCA GCC CCA CAC CAT TAC TAT CTA TTA AAC CTG AAC TTC AAT      456
Glu Leu Pro Ala Pro His His Tyr Tyr Leu Leu Asn Leu Asn Phe Asn
            100                 105                 110

AGT CCT AAT GAA ACT GAC TCC ATT CCA GAA CTA GCT AAC ACG GTT TTT      504
Ser Pro Asn Glu Thr Asp Ser Ile Pro Glu Leu Ala Asn Thr Val Phe
        115                 120                 125

GAG AAA GAT AAT ACA AAA TAT ATT CTG CAA GAA GAT CTC AGT GTT TCC      552
Glu Lys Asp Asn Thr Lys Tyr Ile Leu Gln Glu Asp Leu Ser Val Ser
    130                 135                 140

AAA GAA ATT TCT TCT ACT GAT GGA ACG AAA TGG AGG TTA AGA AGT GAC      600
Lys Glu Ile Ser Ser Thr Asp Gly Thr Lys Trp Arg Leu Arg Ser Asp
145                 150                 155                 160

AGA AAA AGT CTT TTC GAC GTA AAG ACG TTA GCA TAT TCT CTC TAC GAT      648
Arg Lys Ser Leu Phe Asp Val Lys Thr Leu Ala Tyr Ser Leu Tyr Asp
                165                 170                 175

GTA TTT TCA GAA AAT GTA ACC CAA GCA GAC CCG TTT GAC GTC CTT ATT      696
Val Phe Ser Glu Asn Val Thr Gln Ala Asp Pro Phe Asp Val Leu Ile
            180                 185                 190

ATG GTT ACT GCC TAC CTA ATG ATG TTC TAC ACC ATA TTC GGC CTC TTC      744
Met Val Thr Ala Tyr Leu Met Met Phe Tyr Thr Ile Phe Gly Leu Phe
        195                 200                 205

AAT GAC ATG AGG AAG ACC GGG TCA AAT TTT TGG TTG AGC GCC TCT ACA      792
Asn Asp Met Arg Lys Thr Gly Ser Asn Phe Trp Leu Ser Ala Ser Thr
    210                 215                 220

GTG GTC AAT TCT GCA TCA TCA CTT TTC TTA GCA TTG TAT GTC ACC CAA      840
```

-continued

Val Val Asn Ser Ala Ser Ser Leu Phe Leu Ala Leu Tyr Val Thr Gln
225 230 235 240

TGT ATT CTA GGC AAA GAA GTT TCC GCA TTA ACT CTT TTT GAA GGT TTG 888
Cys Ile Leu Gly Lys Glu Val Ser Ala Leu Thr Leu Phe Glu Gly Leu
245 250 255

CCT TTC ATT GTA GTT GTT GTT GGT TTC AAG CAC AAA ATC AAG ATT GCC 936
Pro Phe Ile Val Val Val Val Gly Phe Lys His Lys Ile Lys Ile Ala
260 265 270

CAG TAT GCC CTG GAG AAA TTT GAA AGA GTC GGT TTA TCT AAA AGG ATT 984
Gln Tyr Ala Leu Glu Lys Phe Glu Arg Val Gly Leu Ser Lys Arg Ile
275 280 285

ACT ACC GAT GAA ATC GTT TTT GAA TCC GTG AGC GAA GAG GGT GGT CGT 1032
Thr Thr Asp Glu Ile Val Phe Glu Ser Val Ser Glu Glu Gly Gly Arg
290 295 300

TTG ATT CAA GAC CAT TTG CTT TGT ATT TTT GCC TTT ATC GGA TGC TCT 1080
Leu Ile Gln Asp His Leu Leu Cys Ile Phe Ala Phe Ile Gly Cys Ser
305 310 315 320

ATG TAT GCT CAC CAA TTG AAG ACT TTG ACA AAC TTC TGC ATA TTA TCA 1128
Met Tyr Ala His Gln Leu Lys Thr Leu Thr Asn Phe Cys Ile Leu Ser
325 330 335

GCA TTT ATC CTA ATT TTT GAA TTG ATT TTA ACT CCT ACA TTT TAT TCT 1176
Ala Phe Ile Leu Ile Phe Glu Leu Ile Leu Thr Pro Thr Phe Tyr Ser
340 345 350

GCT ATC TTA GCG CTT AGA CTG GAA ATG AAT GTT ATC CAC AGA TCT ACT 1224
Ala Ile Leu Ala Leu Arg Leu Glu Met Asn Val Ile His Arg Ser Thr
355 360 365

ATT ATC AAG CAA ACA TTA GAA GAA GAC GGT GTT GTT CCA TCT ACA GCA 1272
Ile Ile Lys Gln Thr Leu Glu Glu Asp Gly Val Val Pro Ser Thr Ala
370 375 380

AGA ATC ATT TCT AAA GCA GAA AAG AAA TCC GTA TCT TCT TTC TTA AAT 1320
Arg Ile Ile Ser Lys Ala Glu Lys Lys Ser Val Ser Ser Phe Leu Asn
385 390 395 400

CTC AGT GTG GTT GTC ATT ATC ATG AAA CTC TCT GTC ATA CTG TTG TTT 1368
Leu Ser Val Val Val Ile Ile Met Lys Leu Ser Val Ile Leu Leu Phe
405 410 415

GTT TTC ATC AAC TTT TAT AAC TTT GGT GCA AAT TGG GTC AAT GAT GCC 1416
Val Phe Ile Asn Phe Tyr Asn Phe Gly Ala Asn Trp Val Asn Asp Ala
420 425 430

TTC AAT TCA TTG TAC TTC GAT AAG GAA CGT GTT TCT CTA CCA GAT TTT 1464
Phe Asn Ser Leu Tyr Phe Asp Lys Glu Arg Val Ser Leu Pro Asp Phe
435 440 445

ATT ACC TCG AAT GCC TCT GAA AAC TTT AAA GAG CAA GCT ATT GTT AGT 1512
Ile Thr Ser Asn Ala Ser Glu Asn Phe Lys Glu Gln Ala Ile Val Ser
450 455 460

GTC ACC CCA TTA TTA TAT TAC AAA CCC ATT AAG TCC TAC CAA CGC ATT 1560
Val Thr Pro Leu Leu Tyr Tyr Lys Pro Ile Lys Ser Tyr Gln Arg Ile
465 470 475 480

GAG GAT ATG GTT CTT CTA TTG CTT CGT AAT GTC AGT GTT GCC ATT CGT 1608
Glu Asp Met Val Leu Leu Leu Leu Arg Asn Val Ser Val Ala Ile Arg
485 490 495

GAT AGG TTC GTC AGT AAA TTA GTT CTT TCC GCC TTA GTA TGC AGT GCT 1656
Asp Arg Phe Val Ser Lys Leu Val Leu Ser Ala Leu Val Cys Ser Ala
500 505 510

GTC ATC AAT GTG TAT TTA TTG AAT GCT GCT AGA ATT CAT ACC AGT TAT 1704
Val Ile Asn Val Tyr Leu Leu Asn Ala Ala Arg Ile His Thr Ser Tyr
515 520 525

ACT GCA GAC CAA TTG GTG AAA ACT GAA GTC ACC AAG AAG TCT TTT ACT 1752
Thr Ala Asp Gln Leu Val Lys Thr Glu Val Thr Lys Lys Ser Phe Thr
530 535 540

-continued

```
GCT CCT GTA CAA AAG GCT TCT ACA CCA GTT TTA ACC AAT AAA ACA GTC        1800
Ala Pro Val Gln Lys Ala Ser Thr Pro Val Leu Thr Asn Lys Thr Val
545                 550                 555                 560

ATT TCT GGA TCG AAA GTC AAA AGT TTA TCA TCT GCG CAA TCG AGC TCA        1848
Ile Ser Gly Ser Lys Val Lys Ser Leu Ser Ser Ala Gln Ser Ser Ser
                565                 570                 575

TCA GGA CCT TCA TCA TCT AGT GAG GAA GAT GAT TCC CGC GAT ATT GAA        1896
Ser Gly Pro Ser Ser Ser Ser Glu Glu Asp Asp Ser Arg Asp Ile Glu
            580                 585                 590

AGC TTG GAT AAG AAA ATA CGT CCT TTA GAA GAA TTA GAA GCA TTA TTA        1944
Ser Leu Asp Lys Lys Ile Arg Pro Leu Glu Glu Leu Glu Ala Leu Leu
        595                 600                 605

AGT AGT GGA AAT ACA AAA CAA TTG AAG AAC AAA GAG GTC GCT GCC TTG        1992
Ser Ser Gly Asn Thr Lys Gln Leu Lys Asn Lys Glu Val Ala Ala Leu
    610                 615                 620

GTT ATT CAC GGT AAG TTA CCT TTG TAC GCT TTG GAG AAA AAA TTA GGT        2040
Val Ile His Gly Lys Leu Pro Leu Tyr Ala Leu Glu Lys Lys Leu Gly
625                 630                 635                 640

GAT ACT ACG AGA GCG GTT GCG GTA CGT AGG AAG GCT CTT TCA ATT TTG        2088
Asp Thr Thr Arg Ala Val Ala Val Arg Arg Lys Ala Leu Ser Ile Leu
                645                 650                 655

GCA GAA GCT CCT GTA TTA GCA TCT GAT CGT TTA CCA TAT AAA AAT TAT        2136
Ala Glu Ala Pro Val Leu Ala Ser Asp Arg Leu Pro Tyr Lys Asn Tyr
            660                 665                 670

GAC TAC GAC CGC GTA TTT GGC GCT TGT TGT GAA AAT GTT ATA GGT TAC        2184
Asp Tyr Asp Arg Val Phe Gly Ala Cys Cys Glu Asn Val Ile Gly Tyr
        675                 680                 685

ATG CCT TTG CCC GTT GGT GTT ATA GGC CCC TTG GTT ATC GAT GGT ACA        2232
Met Pro Leu Pro Val Gly Val Ile Gly Pro Leu Val Ile Asp Gly Thr
    690                 695                 700

TCT TAT CAT ATA CCA ATG GCA ACT ACA GAG GGT TGT TTG GTA GCT TCT        2280
Ser Tyr His Ile Pro Met Ala Thr Thr Glu Gly Cys Leu Val Ala Ser
705                 710                 715                 720

GCC ATG CGT GGC TGT AAG GCA ATC AAT GCT GGC GGT GGT GCA ACA ACT        2328
Ala Met Arg Gly Cys Lys Ala Ile Asn Ala Gly Gly Gly Ala Thr Thr
                725                 730                 735

GTT TTA ACT AAG GAT GGT ATG ACA AGA GGC CCA GTA GTC CGT TTC CCA        2376
Val Leu Thr Lys Asp Gly Met Thr Arg Gly Pro Val Val Arg Phe Pro
            740                 745                 750

ACT TTG AAA AGA TCT GGT GCC TGT AAG ATA TGG TTA GAC TCA GAA GAG        2424
Thr Leu Lys Arg Ser Gly Ala Cys Lys Ile Trp Leu Asp Ser Glu Glu
        755                 760                 765

GGA CAA AAC GCA ATT AAA AAA GCT TTT AAC TCT ACA TCA AGA TTT GCA        2472
Gly Gln Asn Ala Ile Lys Lys Ala Phe Asn Ser Thr Ser Arg Phe Ala
    770                 775                 780

CGT CTG CAA CAT ATT CAA ACT TGT CTA GCA GGA GAT TTA CTC TTC ATG        2520
Arg Leu Gln His Ile Gln Thr Cys Leu Ala Gly Asp Leu Leu Phe Met
785                 790                 795                 800

AGA TTT AGA ACA ACT ACT GGT GAC GCA ATG GGT ATG AAT ATG ATT TCT        2568
Arg Phe Arg Thr Thr Thr Gly Asp Ala Met Gly Met Asn Met Ile Ser
                805                 810                 815

AAA GGT GTC GAA TAC TCA TTA AAG CAA ATG GTA GAA GAG TAT GGC TGG        2616
Lys Gly Val Glu Tyr Ser Leu Lys Gln Met Val Glu Glu Tyr Gly Trp
            820                 825                 830

GAA GAT ATG GAG GTT GTC TCC GTT TCT GGT AAC TAC TGT ACC GAC AAA        2664
Glu Asp Met Glu Val Val Ser Val Ser Gly Asn Tyr Cys Thr Asp Lys
        835                 840                 845

AAA CCA GCT GCC ATC AAC TGG ATC GAA GGT CGT GGT AAG AGT GTC GTC        2712
Lys Pro Ala Ala Ile Asn Trp Ile Glu Gly Arg Gly Lys Ser Val Val
    850                 855                 860
```

-continued

```
GCA GAA GCT ACT ATT CCT GGT GAT GTT GTC AGA AAA GTG TTA AAA AGT   2760
Ala Glu Ala Thr Ile Pro Gly Asp Val Val Arg Lys Val Leu Lys Ser
865                 870                 875                 880

GAT GTT TCC GCA TTG GTT GAG TTG AAC ATT GCT AAG AAT TTG GTT GGA   2808
Asp Val Ser Ala Leu Val Glu Leu Asn Ile Ala Lys Asn Leu Val Gly
                885                 890                 895

TCT GCA ATG GCT GGG TCT GTT GGT GGA TTT AAC GCA CAT GCA GCT AAT   2856
Ser Ala Met Ala Gly Ser Val Gly Gly Phe Asn Ala His Ala Ala Asn
            900                 905                 910

TTA GTG ACA GCT GTT TTC TTG GCA TTA GGA CAA GAT CCT GCA CAA AAT   2904
Leu Val Thr Ala Val Phe Leu Ala Leu Gly Gln Asp Pro Ala Gln Asn
        915                 920                 925

GTT GAA AGT TCC AAC TGT ATA ACA TTG ATG AAA GAA GTG GAC GGT GAT   2952
Val Glu Ser Ser Asn Cys Ile Thr Leu Met Lys Glu Val Asp Gly Asp
    930                 935                 940

TTG AGA ATT TCC GTA TCC ATG CCA TCC ATC GAA GTA GGT ACC ATC GGT   3000
Leu Arg Ile Ser Val Ser Met Pro Ser Ile Glu Val Gly Thr Ile Gly
945                 950                 955                 960

GGT GGT ACT GTT CTA GAA CCA CAA GGT GCC ATG TTG GAC TTA TTA GGT   3048
Gly Gly Thr Val Leu Glu Pro Gln Gly Ala Met Leu Asp Leu Leu Gly
                965                 970                 975

GTA AGA GGC CCG CAT GCT ACC GCT CCT GGT ACC AAC GCA CGT CAA TTA   3096
Val Arg Gly Pro His Ala Thr Ala Pro Gly Thr Asn Ala Arg Gln Leu
            980                 985                 990

GCA AGA ATA GTT GCC TGT GCC GTC TTG GCA GGT GAA TTA TCC TTA TGT   3144
Ala Arg Ile Val Ala Cys Ala Val Leu Ala Gly Glu Leu Ser Leu Cys
        995                1000                1005

GCT GCC CTA GCA GCC GGC CAT TTG GTT CAA AGT CAT ATG ACC CAC AAC   3192
Ala Ala Leu Ala Ala Gly His Leu Val Gln Ser His Met Thr His Asn
    1010                1015                1020

AGG AAA CCT GCT GAA CCA ACA AAA CCT AAC AAT TTG GAC GCC ACT GAT   3240
Arg Lys Pro Ala Glu Pro Thr Lys Pro Asn Asn Leu Asp Ala Thr Asp
1025                1030                1035                1040

ATA AAT CGT TTG AAA GAT GGG TCC GTC ACC TGC ATT AAA TCC           3282
Ile Asn Arg Leu Lys Asp Gly Ser Val Thr Cys Ile Lys Ser
                1045                1050

TAAACTTAGT CATACGTCAT TGGTATTCTC TTGAAAAAGA AGCACAACAG CACCATGTGT 3342

TACGTAAAAT ATTTACTT                                               3360
```

( 2 ) INFORMATION FOR SEQ ID NO:2:

( i ) SEQUENCE CHARACTERISTICS:
( A ) LENGTH: 1054 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Pro Pro Leu Phe Lys Gly Leu Lys Gln Met Ala Lys Pro Ile Ala
 1               5                  10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
 65                 70                  75                  80
```

-continued

Asp Ser Ser Leu Asp Gly Trp Val Ser Ile Thr Ala His Glu Ala Ser
85 90 95

Glu Leu Pro Ala Pro His His Tyr Tyr Leu Leu Asn Leu Asn Phe Asn
100 105 110

Ser Pro Asn Glu Thr Asp Ser Ile Pro Glu Leu Ala Asn Thr Val Phe
115 120 125

Glu Lys Asp Asn Thr Lys Tyr Ile Leu Gln Glu Asp Leu Ser Val Ser
130 135 140

Lys Glu Ile Ser Ser Thr Asp Gly Thr Lys Trp Arg Leu Arg Ser Asp
145 150 155 160

Arg Lys Ser Leu Phe Asp Val Lys Thr Leu Ala Tyr Ser Leu Tyr Asp
165 170 175

Val Phe Ser Glu Asn Val Thr Gln Ala Asp Pro Phe Asp Val Leu Ile
180 185 190

Met Val Thr Ala Tyr Leu Met Met Phe Tyr Thr Ile Phe Gly Leu Phe
195 200 205

Asn Asp Met Arg Lys Thr Gly Ser Asn Phe Trp Leu Ser Ala Ser Thr
210 215 220

Val Val Asn Ser Ala Ser Ser Leu Phe Leu Ala Leu Tyr Val Thr Gln
225 230 235 240

Cys Ile Leu Gly Lys Glu Val Ser Ala Leu Thr Leu Phe Glu Gly Leu
245 250 255

Pro Phe Ile Val Val Val Val Gly Phe Lys His Lys Ile Lys Ile Ala
260 265 270

Gln Tyr Ala Leu Glu Lys Phe Glu Arg Val Gly Leu Ser Lys Arg Ile
275 280 285

Thr Thr Asp Glu Ile Val Phe Glu Ser Val Ser Glu Glu Gly Gly Arg
290 295 300

Leu Ile Gln Asp His Leu Leu Cys Ile Phe Ala Phe Ile Gly Cys Ser
305 310 315 320

Met Tyr Ala His Gln Leu Lys Thr Leu Thr Asn Phe Cys Ile Leu Ser
325 330 335

Ala Phe Ile Leu Ile Phe Glu Leu Ile Leu Thr Pro Thr Phe Tyr Ser
340 345 350

Ala Ile Leu Ala Leu Arg Leu Glu Met Asn Val Ile His Arg Ser Thr
355 360 365

Ile Ile Lys Gln Thr Leu Glu Glu Asp Gly Val Val Pro Ser Thr Ala
370 375 380

Arg Ile Ile Ser Lys Ala Glu Lys Lys Ser Val Ser Ser Phe Leu Asn
385 390 395 400

Leu Ser Val Val Val Ile Ile Met Lys Leu Ser Val Ile Leu Leu Phe
405 410 415

Val Phe Ile Asn Phe Tyr Asn Phe Gly Ala Asn Trp Val Asn Asp Ala
420 425 430

Phe Asn Ser Leu Tyr Phe Asp Lys Glu Arg Val Ser Leu Pro Asp Phe
435 440 445

Ile Thr Ser Asn Ala Ser Glu Asn Phe Lys Glu Gln Ala Ile Val Ser
450 455 460

Val Thr Pro Leu Leu Tyr Tyr Lys Pro Ile Lys Ser Tyr Gln Arg Ile
465 470 475 480

Glu Asp Met Val Leu Leu Leu Leu Arg Asn Val Ser Val Ala Ile Arg
485 490 495

-continued

```
Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
    530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
                565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
        595                 600                 605

Ser Ser Gly Asn Thr Lys Gln Leu Lys Asn Lys Glu Val Ala Ala Leu
    610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
        675                 680                 685

Met Pro Leu Pro Val Gly Val Ile Gly Pro Leu Val Ile Asp Gly Thr
    690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735

Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
        755                 760                 765

Gly Gln Asn Ala Ile Lys Lys Ala Phe Asn Ser Thr Ser Arg Phe Ala
    770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
            820                 825                 830

Glu Asp Met Glu Val Val Ser Val Ser Gly Asn Tyr Cys Thr Asp Lys
        835                 840                 845

Lys Pro Ala Ala Ile Asn Trp Ile Glu Gly Arg Gly Lys Ser Val Val
    850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
```

-continued

```
        915                                        920                                        925

Val Glu Ser Ser Asn Cys Ile Thr Leu Met Lys Glu Val Asp Gly Asp
    930                     935                     940

Leu Arg Ile Ser Val Ser Met Pro Ser Ile Glu Val Gly Thr Ile Gly
945                     950                     955                     960

Gly Gly Thr Val Leu Glu Pro Gln Gly Ala Met Leu Asp Leu Leu Gly
                965                     970                     975

Val Arg Gly Pro His Ala Thr Ala Pro Gly Thr Asn Ala Arg Gln Leu
            980                     985                     990

Ala Arg Ile Val Ala Cys Ala Val Leu Ala Gly Glu Leu Ser Leu Cys
        995                     1000                    1005

Ala Ala Leu Ala Ala Gly His Leu Val Gln Ser His Met Thr His Asn
    1010                    1015                    1020

Arg Lys Pro Ala Glu Pro Thr Lys Pro Asn Asn Leu Asp Ala Thr Asp
1025                    1030                    1035                    1040

Ile Asn Arg Leu Lys Asp Gly Ser Val Thr Cys Ile Lys Ser
                1045                    1050
```

( 2 ) INFORMATION FOR SEQ ID NO:3:

( i ) SEQUENCE CHARACTERISTICS:
( A ) LENGTH: 4768 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 164..2827

( x i ) SEQUENCE DESCRIPTION: SEQ ID NO:3:

```
TGTATGTCTT GTCTTTCTCC TAAGGGGCGT AGGCTCATTG ATAACTCATG TCCTCACCTT      60

GCACTCCTTT TGGAATTATT TGGTTTGAGT GAAGAAGACC GGACCTTCGA GGTTCGCAAC     120

TTAAACAATA GACTTGTGAG GATCCAGGGA CCGAGTGGCT ACA ATG TTG TCA CGA       175
                                                Met Leu Ser Arg
                                                  1

CTT TTC CGT ATG CAT GGC CTC TTT GTG GCC TCC CAT CCC TGG GAA GTT       223
Leu Phe Arg Met His Gly Leu Phe Val Ala Ser His Pro Trp Glu Val
  5                  10                  15                  20

ATT GTG GGG ACG GTG ACA CTT ACC ATC TGT ATG ATG TCC ATG AAC ATG       271
Ile Val Gly Thr Val Thr Leu Thr Ile Cys Met Met Ser Met Asn Met
                 25                  30                  35

TTC ACT GGC AAC AAC AAG ATC TGT GGT TGG AAT TAC GAG TGC CCA AAA       319
Phe Thr Gly Asn Asn Lys Ile Cys Gly Trp Asn Tyr Glu Cys Pro Lys
             40                  45                  50

TTT GAG GAG GAT GTA TTG AGC AGT GAC ATC ATC ATC CTC ACC ATA ACA       367
Phe Glu Glu Asp Val Leu Ser Ser Asp Ile Ile Ile Leu Thr Ile Thr
         55                  60                  65

CGG TGC ATC GCC ATC CTG TAC ATT TAC TTC CAG TTC CAG AAC TTA CGT       415
Arg Cys Ile Ala Ile Leu Tyr Ile Tyr Phe Gln Phe Gln Asn Leu Arg
     70                  75                  80

CAG CTT GGG TCG AAG TAT ATT TTA GGT ATT GCT GGC CTG TTC ACA ATT       463
Gln Leu Gly Ser Lys Tyr Ile Leu Gly Ile Ala Gly Leu Phe Thr Ile
 85                  90                  95                 100

TTC TCA AGT TTT GTC TTT AGT ACA GTC GTC ATT CAC TTC TTA GAC AAA       511
Phe Ser Ser Phe Val Phe Ser Thr Val Val Ile His Phe Leu Asp Lys
                105                 110                 115
```

-continued

```
GAA CTG ACG GGC TTA AAT GAA GCT TTG CCC TTT TTC CTG CTT TTG ATT     559
Glu Leu Thr Gly Leu Asn Glu Ala Leu Pro Phe Phe Leu Leu Leu Ile
            120                 125                 130

GAC CTT TCT AGA GCG AGT GCA CTA GCA AAG TTT GCC CTA AGT TCA AAC     607
Asp Leu Ser Arg Ala Ser Ala Leu Ala Lys Phe Ala Leu Ser Ser Asn
        135                 140                 145

TCT CAG GAT GAA GTA AGG GAA AAT ATA GCT CGC GGA ATG GCA ATT CTG     655
Ser Gln Asp Glu Val Arg Glu Asn Ile Ala Arg Gly Met Ala Ile Leu
    150                 155                 160

GGC CCC ACA TTC ACC CTT GAT GCT CTT GTG GAA TGT CTT GTA ATT GGA     703
Gly Pro Thr Phe Thr Leu Asp Ala Leu Val Glu Cys Leu Val Ile Gly
165                 170                 175                 180

GTT GGC ACC ATG TCA GGG GTG CGT CAG CTT GAA ATC ATG TGC TGC TTT     751
Val Gly Thr Met Ser Gly Val Arg Gln Leu Glu Ile Met Cys Cys Phe
                185                 190                 195

GGC TGC ATG TCT GTG CTT GCC AAC TAC TTC GTG TTC ATG ACA TTT TTC     799
Gly Cys Met Ser Val Leu Ala Asn Tyr Phe Val Phe Met Thr Phe Phe
            200                 205                 210

CCA GCG TGT GTG TCC CTG GTC CTT GAG CTT TCT CGG GAA AGT CGA GAG     847
Pro Ala Cys Val Ser Leu Val Leu Glu Leu Ser Arg Glu Ser Arg Glu
        215                 220                 225

GGT CGT CCA ATT TGG CAG CTT AGC CAT TTT GCC CGA GTT TTG GAA GAA     895
Gly Arg Pro Ile Trp Gln Leu Ser His Phe Ala Arg Val Leu Glu Glu
    230                 235                 240

GAA GAG AAT AAA CCA AAC CCT GTA ACC CAA AGG GTC AAG ATG ATT ATG     943
Glu Glu Asn Lys Pro Asn Pro Val Thr Gln Arg Val Lys Met Ile Met
245                 250                 255                 260

TCT TTA GGT TTG GTT CTT GTT CAT GCT CAC AGT CGA TGG ATA GCT GAT     991
Ser Leu Gly Leu Val Leu Val His Ala His Ser Arg Trp Ile Ala Asp
                265                 270                 275

CCT TCC CCT CAG AAT AGC ACA ACA GAA CAT TCT AAA GTC TCC TTG GGA    1039
Pro Ser Pro Gln Asn Ser Thr Thr Glu His Ser Lys Val Ser Leu Gly
            280                 285                 290

CTG GAT GAA GAT GTG TCC AAG AGA ATT GAA CCA AGT GTT TCT CTC TGG    1087
Leu Asp Glu Asp Val Ser Lys Arg Ile Glu Pro Ser Val Ser Leu Trp
        295                 300                 305

CAG TTT TAT CTC TCC AAG ATG ATC AGC ATG GAC ATT GAA CAA GTG GTT    1135
Gln Phe Tyr Leu Ser Lys Met Ile Ser Met Asp Ile Glu Gln Val Val
    310                 315                 320

ACC CTG AGC TTA GCT TTT CTG TTG GCT GTC AAG TAC ATT TTC TTT GAA    1183
Thr Leu Ser Leu Ala Phe Leu Leu Ala Val Lys Tyr Ile Phe Phe Glu
325                 330                 335                 340

CAA GCA GAG ACA GAG TCC ACA CTG TCT TTA AAA AAT CCT ATC ACG TCT    1231
Gln Ala Glu Thr Glu Ser Thr Leu Ser Leu Lys Asn Pro Ile Thr Ser
                345                 350                 355

CCT GTC GTG ACC CCA AAG AAA GCT CCA GAC AAC TGT TGT AGA CGG GAG    1279
Pro Val Val Thr Pro Lys Lys Ala Pro Asp Asn Cys Cys Arg Arg Glu
            360                 365                 370

CCT CTG CTT GTG AGA AGG AGC GAG AAG CTT TCA TCG GTT GAG GAG GAG    1327
Pro Leu Leu Val Arg Arg Ser Glu Lys Leu Ser Ser Val Glu Glu Glu
        375                 380                 385

CCT GGG GTG AGC CAA GAT AGA AAA GTT GAG GTT ATA AAA CCA TTA GTG    1375
Pro Gly Val Ser Gln Asp Arg Lys Val Glu Val Ile Lys Pro Leu Val
    390                 395                 400

GTG GAA ACT GAG AGT GCA AGC AGA GCT ACA TTT GTG CTT GGC GCC TCT    1423
Val Glu Thr Glu Ser Ala Ser Arg Ala Thr Phe Val Leu Gly Ala Ser
405                 410                 415                 420

GGG ACC AGC CCT CCA GTG GCA GCG AGG ACA CAG GAG CTT GAA ATT GAA    1471
Gly Thr Ser Pro Pro Val Ala Ala Arg Thr Gln Glu Leu Glu Ile Glu
                425                 430                 435
```

-continued

```
CTC CCC AGT GAG CCT CGG CCT AAT GAA GAA TGT CTG CAG ATA CTG GAG     1519
Leu Pro Ser Glu Pro Arg Pro Asn Glu Glu Cys Leu Gln Ile Leu Glu
            440                 445                 450

AGT GCC GAG AAA GGT GCA AAG TTC CTT AGC GAT GCA GAG ATC ATC CAG     1567
Ser Ala Glu Lys Gly Ala Lys Phe Leu Ser Asp Ala Glu Ile Ile Gln
        455                 460                 465

TTG GTC AAT GCC AAG CAC ATC CCA GCC TAC AAA TTG GAA ACC TTA ATG     1615
Leu Val Asn Ala Lys His Ile Pro Ala Tyr Lys Leu Glu Thr Leu Met
    470                 475                 480

GAA ACT CAT GAA CGT GGT GTA TCT ATT CGC CGG CAG CTC CTC TCC ACA     1663
Glu Thr His Glu Arg Gly Val Ser Ile Arg Arg Gln Leu Leu Ser Thr
485                 490                 495                 500

AAG CTT CCA GAG CCT TCT TCT CTG CAG TAC CTG CCT TAC AGA GAT TAT     1711
Lys Leu Pro Glu Pro Ser Ser Leu Gln Tyr Leu Pro Tyr Arg Asp Tyr
                505                 510                 515

AAT TAT TCC CTG GTG ATG GGA GCT TGC TGT GAG AAT GTG ATC GGA TAT     1759
Asn Tyr Ser Leu Val Met Gly Ala Cys Cys Glu Asn Val Ile Gly Tyr
            520                 525                 530

ATG CCC ATC CCT GTC GGA GTA GCA GGG CCT CTG TGC CTG GAT GGT AAA     1807
Met Pro Ile Pro Val Gly Val Ala Gly Pro Leu Cys Leu Asp Gly Lys
        535                 540                 545

GAG TAC CAG GTT CCA ATG GCA ACA ACG GAA GGC TGT CTG GTG GCC AGC     1855
Glu Tyr Gln Val Pro Met Ala Thr Thr Glu Gly Cys Leu Val Ala Ser
    550                 555                 560

ACC AAC AGA GGC TGC AGG GCA ATA GGT CTT GGT GGA GGT GCC AGC AGC     1903
Thr Asn Arg Gly Cys Arg Ala Ile Gly Leu Gly Gly Gly Ala Ser Ser
565                 570                 575                 580

CGG GTC CTT GCA GAT GGG ATG ACC CGG GGC CCA GTG GTG CGT CTT CCT     1951
Arg Val Leu Ala Asp Gly Met Thr Arg Gly Pro Val Val Arg Leu Pro
                585                 590                 595

CGT GCT TGT GAT TCT GCA GAA GTG AAG GCC TGG CTT GAA ACA CCC GAA     1999
Arg Ala Cys Asp Ser Ala Glu Val Lys Ala Trp Leu Glu Thr Pro Glu
            600                 605                 610

GGG TTT GCG GTG ATA AAG GAC GCC TTC GAT AGC ACT AGC AGA TTT GCA     2047
Gly Phe Ala Val Ile Lys Asp Ala Phe Asp Ser Thr Ser Arg Phe Ala
        615                 620                 625

CGT CTA CAG AAG CTT CAT GTG ACC ATG GCA GGG CGC AAC CTG TAC ATC     2095
Arg Leu Gln Lys Leu His Val Thr Met Ala Gly Arg Asn Leu Tyr Ile
    630                 635                 640

CGT TTC CAG TCC AAG ACA GGG GAT GCC ATG GGG ATG AAC ATG ATT TCC     2143
Arg Phe Gln Ser Lys Thr Gly Asp Ala Met Gly Met Asn Met Ile Ser
645                 650                 655                 660

AAG GGC ACT GAG AAA GCA CTT CTG AAG CTT CAG GAG TTC TTT CCT GAA     2191
Lys Gly Thr Glu Lys Ala Leu Leu Lys Leu Gln Glu Phe Phe Pro Glu
                665                 670                 675

ATG CAG ATT CTG GCA GTT AGT GGT AAC TAC TGC ACT GAC AAG AAA CCT     2239
Met Gln Ile Leu Ala Val Ser Gly Asn Tyr Cys Thr Asp Lys Lys Pro
            680                 685                 690

GCC GCC ATA AAC TGG ATC GAG GGA AGA GGA AAG ACA GTT GTG TGT GAA     2287
Ala Ala Ile Asn Trp Ile Glu Gly Arg Gly Lys Thr Val Val Cys Glu
        695                 700                 705

GCT GTT ATT CCA GCC AAG GTG GTG AGA GAA GTA TTA AAG ACA ACT ACG     2335
Ala Val Ile Pro Ala Lys Val Val Arg Glu Val Leu Lys Thr Thr Thr
    710                 715                 720

GAA GCT ATG ATT GAC GTA AAC ATT AAC AAG AAT CTT GTG GGT TCT GCC     2383
Glu Ala Met Ile Asp Val Asn Ile Asn Lys Asn Leu Val Gly Ser Ala
725                 730                 735                 740

ATG GCT GGG AGC ATA GGA GGC TAC AAT GCC CAT GCA GCA AAC ATC GTC     2431
Met Ala Gly Ser Ile Gly Gly Tyr Asn Ala His Ala Ala Asn Ile Val
```

-continued

```
                  745                     750                     755

ACT GCT ATC TAC ATT GCA TGT GGC CAG GAT GCA GCA CAG AAT GTG GGG    2479
Thr Ala Ile Tyr Ile Ala Cys Gly Gln Asp Ala Ala Gln Asn Val Gly
            760                 765                 770

AGT TCA AAC TGT ATT ACT TTA ATG GAA GCA AGT GGT CCC ACG AAT GAA    2527
Ser Ser Asn Cys Ile Thr Leu Met Glu Ala Ser Gly Pro Thr Asn Glu
        775                 780                 785

GAC TTG TAT ATC AGC TGC ACC ATG CCA TCT ATA GAG ATA GGA ACT GTG    2575
Asp Leu Tyr Ile Ser Cys Thr Met Pro Ser Ile Glu Ile Gly Thr Val
    790                 795                 800

GGT GGT GGG ACC AAC CTC CTA CCA CAG CAG GCC TGT CTG CAG ATG CTA    2623
Gly Gly Gly Thr Asn Leu Leu Pro Gln Gln Ala Cys Leu Gln Met Leu
805                 810                 815                 820

GGT GTT CAA GGA GCG TGC AAA GAC AAT CCT GGA GAA AAT GCA CGG CAA    2671
Gly Val Gln Gly Ala Cys Lys Asp Asn Pro Gly Glu Asn Ala Arg Gln
                825                 830                 835

CTT GCC CGA ATT GTG TGT GGT ACT GTA ATG GCT GGG GAG TTG TCC TTG    2719
Leu Ala Arg Ile Val Cys Gly Thr Val Met Ala Gly Glu Leu Ser Leu
            840                 845                 850

ATG GCA GCA TTG GCA GCA GGA CAT CTT GTT AGA AGT CAC ATG GTT CAT    2767
Met Ala Ala Leu Ala Ala Gly His Leu Val Arg Ser His Met Val His
        855                 860                 865

AAC AGA TCG AAG ATA AAT TTA CAA GAT CTG CAA GGA ACG TGC ACC AAG    2815
Asn Arg Ser Lys Ile Asn Leu Gln Asp Leu Gln Gly Thr Cys Thr Lys
    870                 875                 880

AAG TCA GCT TGAGCAGCCT GACAGTATTG AACTGAAACA CGGGCATTGG            2864
Lys Ser Ala
885

GTTCTCAAGG ACTAACATGA AATCTGTGAA TTAAAAATCT CAATGCAGTG TCTTGTGGAA  2924

GATGAATGAA CGTGATCAGT GAGACGCCTG CTTGGTTTCT GGCTCTTTCA GAGACGTCTG  2984

AGGTCCTTTG CTCGGAGACT CCTCAGATCT GGAAACAGTG TGGTCCTTCC CATGCTGTAT  3044

TCTGAAAAGA TCTCATATGG ATGTTGTGCT CTGAGCACCA CAGATGTGAT CTGCAGCTCG  3104

TTTCTGAAAT GATGGAGTTC ATGGTGATCA GTGTGAGACT GGCCTCTCCC AGCAGGTTAA  3164

AAATGGAGTT TTAAATTATA CTGTAGCTGA CAGTACTTCT GATTTTATAT TTATTTAGTC  3224

TGAGTTGTAG AACTTTGCAA TCTAAGTTTA TTTTTTGTAA CCTAATAATT CATTTGGTGC  3284

TGGTCTATTG ATTTTTGGGG GTAAACAATA TTATTCTTCA GAAGGGGACC TACTTCTTCA  3344

TGGGAAGAAT TACTTTTATT CTCAAACTAC AGAACAATGT GCTAAGCAGT GCTAAATTGT  3404

TCTCATGAAG AAAACAGTCA CTGCATTTAT CTCTGTAGGC CTTTTTTCAG AGAGGCCTTG  3464

TCTAGATTTT TGCCAGCTAG GCTACTGCAT GTCTTAGTGT CAGGCCTTAG GAAAGTGCCA  3524

CGCTCTGCAC TAAAGATATC AGAGCTCTTG GTGTTACTTA GACAAGAGTA TGAGCAAGTC  3584

GGACCTCTCA GAGTGTGGGA ACACAGTTTT GAAAGAAAAA CCATTTCTCT AAGCCAATTT  3644

TCTTTAAAGA CATTTTAACT TATTTAGCTG AGTTCTAGAT TTTTCGGGTA AACTATCAAA  3704

TCTGTATATG TTGTAATAAA GTGTCTTATG CTAGGAGTTT ATTCAAAGTG TTTAAGTAAT  3764

AAAAGGACTC AAATTTACAC TGATAAAATA CTCTAGCTTG GGCCAGAGAA GACAGTGCTC  3824

ATTAGCGTTG TCCAGGAAAC CCTGCTTGCT TGCCAAGCCT AATGAAGGGA AAGTCAGCTT  3884

TCAGAGCCAA TGATGGAGGC CACATGAATG GCCCTGGAGC TGTGTGCCTT GTTCTGTGGC  3944

CAGGAGCTTG GTGACTGAAT CATTTACGGG CTCCTTTGAT GGACCCATAA AAGCTCTTAG  4004

CTTCCTCAGG GGGTCAGCAG AGTTGTTGAA TCTTAATTTT TTTTTTAATG TACCAGTTTT  4064

GTATAAATAA TAATAAAGAG CTCCTTATTT TGTATTCTAT CTAATGCTTC GAGTTCAGTC  4124
```

-continued

```
TTGGGAAGCT GACATCTCAT GTAGAAGATG GACTCTGAAA GACATTCCAA GAGTGCAGCG 4184
GCATCATGGG AGCCTCTTAG TGATTGTGTG TCAGTATTAT TGTGGAAGAT TGACTTTGCT 4244
TTTGTATGTG AAGTTTCAGA TTGCTCCTCT TGTGACTTTT TAGCCAGTAA CATTTTATTT 4304
ACCTGAGCTT GTCATGGAAG TGGCAGTGAA AAGTATTGAG TATTCATGCT GGTGACTGTA 4364
ACCAATGTCA TCTTGCTAAA AACTCATGTT TTGTACAATT ACTAAATTGT ATACATTTTG 4424
TTATAGAATA CTTTTTCCAG TTGAGTAAAT TATGAAAGGA AGTTAACATT AACAGGTGTA 4484
AGCGGTGGCT TTTTTAAAAT GAAGGATTAA CCCTAAGCCC GAGACCCAGA AGCTAGCAAA 4544
GTCTGGCAGA GTGGTAAACT GTCCTGCTGG GGCCATCCAA TCATCTCTCT CCATTACACT 4604
TTCTAACTTT GCAGCATTGG TGCTGGCCAG TGTATTGTTT CATTGATCTT CCTTACGCTT 4664
AGAGGGTTTG ATTGGTTCAG ATCTATAATC TCAGCCACAT TGTCTTGGTA TCAGCTGGAG 4724
AGAGTTAAGA GGAAGGGAAA ATAAAGTTCA GATAGCCAAA ACAC                  4768
```

( 2 ) INFORMATION FOR SEQ ID NO:4:

( i ) SEQUENCE CHARACTERISTICS:
( A ) LENGTH: 887 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Leu Ser Arg Leu Phe Arg Met His Gly Leu Phe Val Ala Ser His
1               5                   10                  15

Pro Trp Glu Val Ile Val Gly Thr Val Thr Leu Thr Ile Cys Met Met
            20                  25                  30

Ser Met Asn Met Phe Thr Gly Asn Asn Lys Ile Cys Gly Trp Asn Tyr
        35                  40                  45

Glu Cys Pro Lys Phe Glu Glu Asp Val Leu Ser Ser Asp Ile Ile Ile
    50                  55                  60

Leu Thr Ile Thr Arg Cys Ile Ala Ile Leu Tyr Ile Tyr Phe Gln Phe
65                  70                  75                  80

Gln Asn Leu Arg Gln Leu Gly Ser Lys Tyr Ile Leu Gly Ile Ala Gly
                85                  90                  95

Leu Phe Thr Ile Phe Ser Ser Phe Val Phe Ser Thr Val Val Ile His
            100                 105                 110

Phe Leu Asp Lys Glu Leu Thr Gly Leu Asn Glu Ala Leu Pro Phe Phe
        115                 120                 125

Leu Leu Leu Ile Asp Leu Ser Arg Ala Ser Ala Leu Ala Lys Phe Ala
    130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                165                 170                 175

Leu Val Ile Gly Val Gly Thr Met Ser Gly Val Arg Gln Leu Glu Ile
            180                 185                 190

Met Cys Cys Phe Gly Cys Met Ser Val Leu Ala Asn Tyr Phe Val Phe
        195                 200                 205

Met Thr Phe Phe Pro Ala Cys Val Ser Leu Val Leu Glu Leu Ser Arg
    210                 215                 220

Glu Ser Arg Glu Gly Arg Pro Ile Trp Gln Leu Ser His Phe Ala Arg
225                 230                 235                 240
```

-continued

Val Leu Glu Glu Glu Glu Asn Lys Pro Asn Pro Val Thr Gln Arg Val
245 250 255

Lys Met Ile Met Ser Leu Gly Leu Val Leu Val His Ala His Ser Arg
260 265 270

Trp Ile Ala Asp Pro Ser Pro Gln Asn Ser Thr Thr Glu His Ser Lys
275 280 285

Val Ser Leu Gly Leu Asp Glu Asp Val Ser Lys Arg Ile Glu Pro Ser
290 295 300

Val Ser Leu Trp Gln Phe Tyr Leu Ser Lys Met Ile Ser Met Asp Ile
305 310 315 320

Glu Gln Val Val Thr Leu Ser Leu Ala Phe Leu Leu Ala Val Lys Tyr
325 330 335

Ile Phe Phe Glu Gln Ala Glu Thr Glu Ser Thr Leu Ser Leu Lys Asn
340 345 350

Pro Ile Thr Ser Pro Val Val Thr Pro Lys Lys Ala Pro Asp Asn Cys
355 360 365

Cys Arg Arg Glu Pro Leu Leu Val Arg Arg Ser Glu Lys Leu Ser Ser
370 375 380

Val Glu Glu Glu Pro Gly Val Ser Gln Asp Arg Lys Val Glu Val Ile
385 390 395 400

Lys Pro Leu Val Val Glu Thr Glu Ser Ala Ser Arg Ala Thr Phe Val
405 410 415

Leu Gly Ala Ser Gly Thr Ser Pro Pro Val Ala Ala Arg Thr Gln Glu
420 425 430

Leu Glu Ile Glu Leu Pro Ser Glu Pro Arg Pro Asn Glu Glu Cys Leu
435 440 445

Gln Ile Leu Glu Ser Ala Glu Lys Gly Ala Lys Phe Leu Ser Asp Ala
450 455 460

Glu Ile Ile Gln Leu Val Asn Ala Lys His Ile Pro Ala Tyr Lys Leu
465 470 475 480

Glu Thr Leu Met Glu Thr His Glu Arg Gly Val Ser Ile Arg Arg Gln
485 490 495

Leu Leu Ser Thr Lys Leu Pro Glu Pro Ser Ser Leu Gln Tyr Leu Pro
500 505 510

Tyr Arg Asp Tyr Asn Tyr Ser Leu Val Met Gly Ala Cys Cys Glu Asn
515 520 525

Val Ile Gly Tyr Met Pro Ile Pro Val Gly Val Ala Gly Pro Leu Cys
530 535 540

Leu Asp Gly Lys Glu Tyr Gln Val Pro Met Ala Thr Thr Glu Gly Cys
545 550 555 560

Leu Val Ala Ser Thr Asn Arg Gly Cys Arg Ala Ile Gly Leu Gly Gly
565 570 575

Gly Ala Ser Ser Arg Val Leu Ala Asp Gly Met Thr Arg Gly Pro Val
580 585 590

Val Arg Leu Pro Arg Ala Cys Asp Ser Ala Glu Val Lys Ala Trp Leu
595 600 605

Glu Thr Pro Glu Gly Phe Ala Val Ile Lys Asp Ala Phe Asp Ser Thr
610 615 620

Ser Arg Phe Ala Arg Leu Gln Lys Leu His Val Thr Met Ala Gly Arg
625 630 635 640

Asn Leu Tyr Ile Arg Phe Gln Ser Lys Thr Gly Asp Ala Met Gly Met
645 650 655

-continued

```
Asn Met Ile Ser Lys Gly Thr Glu Lys Ala Leu Leu Lys Leu Gln Glu
            660                 665                 670

Phe Phe Pro Glu Met Gln Ile Leu Ala Val Ser Gly Asn Tyr Cys Thr
        675                 680                 685

Asp Lys Lys Pro Ala Ala Ile Asn Trp Ile Glu Gly Arg Gly Lys Thr
    690                 695                 700

Val Val Cys Glu Ala Val Ile Pro Ala Lys Val Val Arg Glu Val Leu
705                 710                 715                 720

Lys Thr Thr Thr Glu Ala Met Ile Asp Val Asn Ile Asn Lys Asn Leu
                725                 730                 735

Val Gly Ser Ala Met Ala Gly Ser Ile Gly Gly Tyr Asn Ala His Ala
            740                 745                 750

Ala Asn Ile Val Thr Ala Ile Tyr Ile Ala Cys Gly Gln Asp Ala Ala
        755                 760                 765

Gln Asn Val Gly Ser Ser Asn Cys Ile Thr Leu Met Glu Ala Ser Gly
    770                 775                 780

Pro Thr Asn Glu Asp Leu Tyr Ile Ser Cys Thr Met Pro Ser Ile Glu
785                 790                 795                 800

Ile Gly Thr Val Gly Gly Gly Thr Asn Leu Leu Pro Gln Gln Ala Cys
                805                 810                 815

Leu Gln Met Leu Gly Val Gln Gly Ala Cys Lys Asp Asn Pro Gly Glu
            820                 825                 830

Asn Ala Arg Gln Leu Ala Arg Ile Val Cys Gly Thr Val Met Ala Gly
        835                 840                 845

Glu Leu Ser Leu Met Ala Ala Leu Ala Ala Gly His Leu Val Arg Ser
    850                 855                 860

His Met Val His Asn Arg Ser Lys Ile Asn Leu Gln Asp Leu Gln Gly
865                 870                 875                 880

Thr Cys Thr Lys Lys Ser Ala
                885
```

( 2 ) INFORMATION FOR SEQ ID NO:5:

( i ) SEQUENCE CHARACTERISTICS:
( A ) LENGTH: 3348 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 121..3255

( x i ) SEQUENCE DESCRIPTION: SEQ ID NO:5:

```
GGAATATTTT GTACGAGCAA GTTATAGTAA GACACTTCAG TGAGAAATTA ATCTGACTTA      60

CTTTTACTTA ATTGTGTTCT TTCCAAATTA GTTCAACAAG GTTCCCACAT ACAACCTCAA     120

ATG TCA CTT CCC TTA AAA ACG ATA GTA CAT TTG GTA AAG CCC TTT GCT       168
Met Ser Leu Pro Leu Lys Thr Ile Val His Leu Val Lys Pro Phe Ala
  1               5                  10                  15

TGC ACT GCT AGG TTT AGT GCG AGA TAC CCA ATC CAC GTC ATT GTT GTT       216
Cys Thr Ala Arg Phe Ser Ala Arg Tyr Pro Ile His Val Ile Val Val
            20                  25                  30

GCT GTT TTA TTG AGT GCC GCT GCT TAT CTA TCC GTG ACA CAA TCT TAC       264
Ala Val Leu Leu Ser Ala Ala Ala Tyr Leu Ser Val Thr Gln Ser Tyr
        35                  40                  45

CTT AAC GAA TGG AAG CTG GAC TCT AAT CAG TAT TCT ACA TAC TTA AGC       312
```

-continued

```
Leu Asn Glu Trp Lys Leu Asp Ser Asn Gln Tyr Ser Thr Tyr Leu Ser
     50                     55                  60

ATA AAG CCG GAT GAG TTG TTT GAA AAA TGC ACA CAC TAC TAT AGG TCT     360
Ile Lys Pro Asp Glu Leu Phe Glu Lys Cys Thr His Tyr Tyr Arg Ser
 65                 70                  75                  80

CCT GTG TCT GAT ACA TGG AAG TTA CTC AGC TCT AAA GAA GCC GCC GAT     408
Pro Val Ser Asp Thr Trp Lys Leu Leu Ser Ser Lys Glu Ala Ala Asp
                 85                  90                  95

ATT TAT ACC CCT TTT CAT TAT TAT TTG TCT ACC ATA AGT TTT CAA AGT     456
Ile Tyr Thr Pro Phe His Tyr Tyr Leu Ser Thr Ile Ser Phe Gln Ser
            100                 105                 110

AAG GAC AAT TCA ACG ACT TTG CCT TCC CTT GAT GAC GTT ATT TAC AGT     504
Lys Asp Asn Ser Thr Thr Leu Pro Ser Leu Asp Asp Val Ile Tyr Ser
        115                 120                 125

GTT GAC CAT ACC AGG TAC TTA TTA AGT GAA GAG CCA AAG ATA CCA ACT     552
Val Asp His Thr Arg Tyr Leu Leu Ser Glu Glu Pro Lys Ile Pro Thr
    130                 135                 140

GAA CTA GTG TCT GAA AAC GGA ACG AAA TGG AGA TTG AGA AAC AAC AGC     600
Glu Leu Val Ser Glu Asn Gly Thr Lys Trp Arg Leu Arg Asn Asn Ser
145                 150                 155                 160

AAT TTT ATT TTG GAC CTG CAT AAT ATT TAC CGA AAT ATG GTG AAG CAA     648
Asn Phe Ile Leu Asp Leu His Asn Ile Tyr Arg Asn Met Val Lys Gln
                165                 170                 175

TTT TCT AAC AAA ACG AGC GAA TTT GAT CAG TTC GAT TTG TTT ATC ATC     696
Phe Ser Asn Lys Thr Ser Glu Phe Asp Gln Phe Asp Leu Phe Ile Ile
            180                 185                 190

CTA GCT GCT TAC CTT ACT CTT TTT TAT ACT CTC TGT TGC CTG TTT AAT     744
Leu Ala Ala Tyr Leu Thr Leu Phe Tyr Thr Leu Cys Cys Leu Phe Asn
        195                 200                 205

GAC ATG AGG AAA ATC GGA TCA AAG TTT TGG TTA AGC TTT TCT GCT CTT     792
Asp Met Arg Lys Ile Gly Ser Lys Phe Trp Leu Ser Phe Ser Ala Leu
    210                 215                 220

TCA AAC TCT GCA TGC GCA TTA TAT TTA TCG CTG TAC ACA ACT CAC AGT     840
Ser Asn Ser Ala Cys Ala Leu Tyr Leu Ser Leu Tyr Thr Thr His Ser
225                 230                 235                 240

TTA TTG AAG AAA CCG GCT TCC TTA TTA AGT TTG GTC ATT GGA CTA CCA     888
Leu Leu Lys Lys Pro Ala Ser Leu Leu Ser Leu Val Ile Gly Leu Pro
                245                 250                 255

TTT ATC GTA GTA ATT ATT GGC TTT AAG CAT AAA GTT CGA CTT GCG GCA     936
Phe Ile Val Val Ile Ile Gly Phe Lys His Lys Val Arg Leu Ala Ala
            260                 265                 270

TTC TCG CTA CAA AAA TTC CAC AGA ATT AGT ATT GAC AAG AAA ATA ACG     984
Phe Ser Leu Gln Lys Phe His Arg Ile Ser Ile Asp Lys Lys Ile Thr
        275                 280                 285

GTA AGC AAC ATT ATT TAT GAG GCT ATG TTT CAA GAA GGT GCC TAC TTA    1032
Val Ser Asn Ile Ile Tyr Glu Ala Met Phe Gln Glu Gly Ala Tyr Leu
    290                 295                 300

ATC CGC GAC TAC TTA TTT TAT ATT AGC TCC TTC ATT GGA TGT GCT ATT    1080
Ile Arg Asp Tyr Leu Phe Tyr Ile Ser Ser Phe Ile Gly Cys Ala Ile
305                 310                 315                 320

TAT GCT AGA CAT CTT CCC GGA TTG GTC AAT TTC TGT ATT TTG TCT ACA    1128
Tyr Ala Arg His Leu Pro Gly Leu Val Asn Phe Cys Ile Leu Ser Thr
                325                 330                 335

TTT ATG CTA GTT TTC GAC TTG CTT TTG TCT GCT ACT TTT TAT TCT GCC    1176
Phe Met Leu Val Phe Asp Leu Leu Leu Ser Ala Thr Phe Tyr Ser Ala
            340                 345                 350

ATT TTA TCA ATG AAG CTG GAA ATT AAC ATC ATT CAC AGA TCA ACC GTC    1224
Ile Leu Ser Met Lys Leu Glu Ile Asn Ile Ile His Arg Ser Thr Val
        355                 360                 365
```

-continued

```
ATC AGA CAG ACT TTG GAA GAG GAC GGA GTT GTC CCA ACT ACA GCA GAT    1272
Ile Arg Gln Thr Leu Glu Glu Asp Gly Val Val Pro Thr Thr Ala Asp
    370                 375                 380

ATT ATA TAT AAG GAT GAA ACT GCC TCA GAA CCA CAT TTT TTG AGA TCT    1320
Ile Ile Tyr Lys Asp Glu Thr Ala Ser Glu Pro His Phe Leu Arg Ser
385                 390                 395                 400

AAC GTG GCT ATC ATT CTG GGA AAA GCA TCA GTT ATT GGT CTT TTG CTT    1368
Asn Val Ala Ile Ile Leu Gly Lys Ala Ser Val Ile Gly Leu Leu Leu
                405                 410                 415

CTG ATC AAC CTT TAT GTT TTC ACA GAT AAG TTA AAT GCT ACA ATA CTA    1416
Leu Ile Asn Leu Tyr Val Phe Thr Asp Lys Leu Asn Ala Thr Ile Leu
            420                 425                 430

AAC ACG GTA TAT TTT GAC TCT ACA ATT TAC TCG TTA CCA AAT TTT ATC    1464
Asn Thr Val Tyr Phe Asp Ser Thr Ile Tyr Ser Leu Pro Asn Phe Ile
        435                 440                 445

AAT TAT AAA GAT ATT GGC AAT CTC AGC AAT CAA GTG ATC ATT TCC GTG    1512
Asn Tyr Lys Asp Ile Gly Asn Leu Ser Asn Gln Val Ile Ile Ser Val
    450                 455                 460

TTG CCA AAG CAA TAT TAT ACT CCG CTG AAA AAA TAC CAT CAG ATC GAA    1560
Leu Pro Lys Gln Tyr Tyr Thr Pro Leu Lys Lys Tyr His Gln Ile Glu
465                 470                 475                 480

GAT TCT GTT CTA CTT ATC ATT GAT TCC GTT AGC AAT GCT ATT CGG GAC    1608
Asp Ser Val Leu Leu Ile Ile Asp Ser Val Ser Asn Ala Ile Arg Asp
                485                 490                 495

CAA TTT ATC AGC AAG TTA CTT TTT TTT GCA TTT GCA GTT AGT ATT TCC    1656
Gln Phe Ile Ser Lys Leu Leu Phe Phe Ala Phe Ala Val Ser Ile Ser
            500                 505                 510

ATC AAT GTC TAC TTA CTG AAT GCT GCA AAA ATT CAC ACA GGA TAC ATG    1704
Ile Asn Val Tyr Leu Leu Asn Ala Ala Lys Ile His Thr Gly Tyr Met
        515                 520                 525

AAC TTC CAA CCA CAA TCA AAT AAG ATC GAT GAT CTT GTT GTT CAG CAA    1752
Asn Phe Gln Pro Gln Ser Asn Lys Ile Asp Asp Leu Val Val Gln Gln
    530                 535                 540

AAA TCG GCA ACG ATT GAG TTT TCA GAA ACT CGA AGT ATG CCT GCT TCT    1800
Lys Ser Ala Thr Ile Glu Phe Ser Glu Thr Arg Ser Met Pro Ala Ser
545                 550                 555                 560

TCT GGC CTA GAA ACT CCA GTG ACC GCG AAA GAT ATA ATT ATC TCT GAA    1848
Ser Gly Leu Glu Thr Pro Val Thr Ala Lys Asp Ile Ile Ile Ser Glu
                565                 570                 575

GAA ATC CAG AAT AAC GAA TGC GTC TAT GCT TTG AGT TCC CAG GAC GAG    1896
Glu Ile Gln Asn Asn Glu Cys Val Tyr Ala Leu Ser Ser Gln Asp Glu
            580                 585                 590

CCT ATC CGT CCT TTA TCG AAT TTA GTG GAA CTT ATG GAG AAA GAA CAA    1944
Pro Ile Arg Pro Leu Ser Asn Leu Val Glu Leu Met Glu Lys Glu Gln
        595                 600                 605

TTA AAG AAC ATG AAT AAT ACT GAG GTT TCG AAT CTT GTC GTC AAC GGT    1992
Leu Lys Asn Met Asn Asn Thr Glu Val Ser Asn Leu Val Val Asn Gly
    610                 615                 620

AAA CTG CCA TTA TAT TCC TTA GAG AAA AAA TTA GAG GAC ACA ACT CGT    2040
Lys Leu Pro Leu Tyr Ser Leu Glu Lys Lys Leu Glu Asp Thr Thr Arg
625                 630                 635                 640

GCG GTT TTA GTT AGG AGA AAG GCA CTT TCA ACT TTG GCT GAA TCG CCA    2088
Ala Val Leu Val Arg Arg Lys Ala Leu Ser Thr Leu Ala Glu Ser Pro
                645                 650                 655

ATT TTA GTT TCC GAA AAA TTG CCC TTC AGA AAT TAT GAT TAT GAT CGC    2136
Ile Leu Val Ser Glu Lys Leu Pro Phe Arg Asn Tyr Asp Tyr Asp Arg
            660                 665                 670

GTT TTT GGA GCT TGC TGT GAA AAT GTC ATC GGC TAT ATG CCA ATA CCA    2184
Val Phe Gly Ala Cys Cys Glu Asn Val Ile Gly Tyr Met Pro Ile Pro
        675                 680                 685
```

-continued

```
GTT GGT GTA ATT GGT CCA TTA ATT ATT GAT GGA ACA TCT TAT CAC ATA    2232
Val Gly Val Ile Gly Pro Leu Ile Ile Asp Gly Thr Ser Tyr His Ile
    690                 695                 700

CCA ATG GCA ACC ACG GAA GGT TGT TTA GTG GCT TCA GCT ATG CGT GGT    2280
Pro Met Ala Thr Thr Glu Gly Cys Leu Val Ala Ser Ala Met Arg Gly
705                 710                 715                 720

TGC AAA GCC ATC AAT GCT GGT GGT GGT GCA ACA ACT GTT TTA ACC AAA    2328
Cys Lys Ala Ile Asn Ala Gly Gly Gly Ala Thr Thr Val Leu Thr Lys
                725                 730                 735

GAT GGT ATG ACT AGA GGC CCA GTC GTT CGT TTC CCT ACT TTA ATA AGA    2376
Asp Gly Met Thr Arg Gly Pro Val Val Arg Phe Pro Thr Leu Ile Arg
            740                 745                 750

TCT GGT GCC TGC AAG ATA TGG TTA GAC TCG GAA GAG GGA CAA AAT TCA    2424
Ser Gly Ala Cys Lys Ile Trp Leu Asp Ser Glu Glu Gly Gln Asn Ser
        755                 760                 765

ATT AAA AAA GCT TTT AAT TCT ACA TCA AGG TTT GCA CGT TTG CAA CAT    2472
Ile Lys Lys Ala Phe Asn Ser Thr Ser Arg Phe Ala Arg Leu Gln His
    770                 775                 780

ATT CAA ACC TGT CTA GCA GGC GAT TTG CTT TTT ATG AGA TTT CGG ACA    2520
Ile Gln Thr Cys Leu Ala Gly Asp Leu Leu Phe Met Arg Phe Arg Thr
785                 790                 795                 800

ACT ACC GGT GAC GCA ATG GGT ATG AAC ATG ATA TCG AAA GGT GTC GAA    2568
Thr Thr Gly Asp Ala Met Gly Met Asn Met Ile Ser Lys Gly Val Glu
                805                 810                 815

TAC TCT TTG AAA CAA ATG GTA GAA GAA TAT GGT TGG GAA GAT ATG GAA    2616
Tyr Ser Leu Lys Gln Met Val Glu Glu Tyr Gly Trp Glu Asp Met Glu
            820                 825                 830

GTT GTC TCC GTA TCT GGT AAC TAT TGT ACT GAT AAG AAA CCT GCC GCA    2664
Val Val Ser Val Ser Gly Asn Tyr Cys Thr Asp Lys Lys Pro Ala Ala
        835                 840                 845

ATC AAT TGG ATT GAA GGT CGT GGT AAA AGT GTC GTA GCT GAA GCT ACT    2712
Ile Asn Trp Ile Glu Gly Arg Gly Lys Ser Val Val Ala Glu Ala Thr
    850                 855                 860

ATT CCT GGT GAT GTC GTA AAA AGT GTT TTA AAG AGC GAT GTT TCC GCT    2760
Ile Pro Gly Asp Val Val Lys Ser Val Leu Lys Ser Asp Val Ser Ala
865                 870                 875                 880

TTA GTT GAA TTA AAT ATA TCC AAG AAC TTG GTT GGA TCC GCA ATG GCT    2808
Leu Val Glu Leu Asn Ile Ser Lys Asn Leu Val Gly Ser Ala Met Ala
                885                 890                 895

GGA TCT GTT GGT GGT TTC AAC GCG CAC GCA GCT AAT TTG GTC ACT GCA    2856
Gly Ser Val Gly Gly Phe Asn Ala His Ala Ala Asn Leu Val Thr Ala
            900                 905                 910

CTT TTC TTG GCA TTA GGC CAA GAT CCT GCG CAG AAC GTC GAA AGT TCC    2904
Leu Phe Leu Ala Leu Gly Gln Asp Pro Ala Gln Asn Val Glu Ser Ser
        915                 920                 925

AAC TGT ATA ACT TTG ATG AAG GAA GTT GAT GGT GAT TTA AGG ATC TCT    2952
Asn Cys Ile Thr Leu Met Lys Glu Val Asp Gly Asp Leu Arg Ile Ser
    930                 935                 940

GTT TCC ATG CCA TCT ATT GAA GTT GGT ACG ATT GGC GGG GGT ACT GTT    3000
Val Ser Met Pro Ser Ile Glu Val Gly Thr Ile Gly Gly Gly Thr Val
945                 950                 955                 960

CTG GAG CCT CAG GGC GCC ATG CTT GAT CTT CTC GGC GTT CGT GGT CCT    3048
Leu Glu Pro Gln Gly Ala Met Leu Asp Leu Leu Gly Val Arg Gly Pro
                965                 970                 975

CAC CCC ACT GAA CCT GGA GCA AAT GCT AGG CAA TTA GCT AGA ATA ATC    3096
His Pro Thr Glu Pro Gly Ala Asn Ala Arg Gln Leu Ala Arg Ile Ile
            980                 985                 990

GCG TGT GCT GTC TTG GCT GGT GAA CTG TCT CTG TGC TCC GCA CTT GCT    3144
Ala Cys Ala Val Leu Ala Gly Glu Leu Ser Leu Cys Ser Ala Leu Ala
```

-continued 995 1000 1005

GCC GGT CAC CTG GTA CAA AGC CAT ATG ACT CAC AAC CGT AAA ACA AAC 3192
Ala Gly His Leu Val Gln Ser His Met Thr His Asn Arg Lys Thr Asn
1010 1015 1020

AAA GCC AAT GAA CTG CCA CAA CCA AGT AAC AAA GGG CCC CCC TGT AAA 3240
Lys Ala Asn Glu Leu Pro Gln Pro Ser Asn Lys Gly Pro Pro Cys Lys
1025 1030 1035 1040

ACC TCA GCA TTA TTA TAACTCTTGT AGTTTACATG GTGATACTTT ATATCTTTGT 3295
Thr Ser Ala Leu Leu
1045

ATTGTCTAGC TATTCTAAAT CATCTGCATG TAATAAGAAG TTGATCAAAA TGA 3348

( 2 ) INFORMATION FOR SEQ ID NO:6:

( i ) SEQUENCE CHARACTERISTICS:
( A ) LENGTH: 1045 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Ser Leu Pro Leu Lys Thr Ile Val His Leu Val Lys Pro Phe Ala
1 5 10 15

Cys Thr Ala Arg Phe Ser Ala Arg Tyr Pro Ile His Val Ile Val Val
20 25 30

Ala Val Leu Leu Ser Ala Ala Ala Tyr Leu Ser Val Thr Gln Ser Tyr
35 40 45

Leu Asn Glu Trp Lys Leu Asp Ser Asn Gln Tyr Ser Thr Tyr Leu Ser
50 55 60

Ile Lys Pro Asp Glu Leu Phe Glu Lys Cys Thr His Tyr Tyr Arg Ser
65 70 75 80

Pro Val Ser Asp Thr Trp Lys Leu Leu Ser Ser Lys Glu Ala Ala Asp
85 90 95

Ile Tyr Thr Pro Phe His Tyr Tyr Leu Ser Thr Ile Ser Phe Gln Ser
100 105 110

Lys Asp Asn Ser Thr Thr Leu Pro Ser Leu Asp Asp Val Ile Tyr Ser
115 120 125

Val Asp His Thr Arg Tyr Leu Leu Ser Glu Glu Pro Lys Ile Pro Thr
130 135 140

Glu Leu Val Ser Glu Asn Gly Thr Lys Trp Arg Leu Arg Asn Asn Ser
145 150 155 160

Asn Phe Ile Leu Asp Leu His Asn Ile Tyr Arg Asn Met Val Lys Gln
165 170 175

Phe Ser Asn Lys Thr Ser Glu Phe Asp Gln Phe Asp Leu Phe Ile Ile
180 185 190

Leu Ala Ala Tyr Leu Thr Leu Phe Tyr Thr Leu Cys Cys Leu Phe Asn
195 200 205

Asp Met Arg Lys Ile Gly Ser Lys Phe Trp Leu Ser Phe Ser Ala Leu
210 215 220

Ser Asn Ser Ala Cys Ala Leu Tyr Leu Ser Leu Tyr Thr Thr His Ser
225 230 235 240

Leu Leu Lys Lys Pro Ala Ser Leu Leu Ser Leu Val Ile Gly Leu Pro
245 250 255

Phe Ile Val Val Ile Ile Gly Phe Lys His Lys Val Arg Leu Ala Ala
260 265 270

-continued

```
Phe Ser Leu Gln Lys Phe His Arg Ile Ser Ile Asp Lys Lys Ile Thr
        275                 280                 285

Val Ser Asn Ile Ile Tyr Glu Ala Met Phe Gln Glu Gly Ala Tyr Leu
    290                 295                 300

Ile Arg Asp Tyr Leu Phe Tyr Ile Ser Ser Phe Ile Gly Cys Ala Ile
305                 310                 315                 320

Tyr Ala Arg His Leu Pro Gly Leu Val Asn Phe Cys Ile Leu Ser Thr
                325                 330                 335

Phe Met Leu Val Phe Asp Leu Leu Leu Ser Ala Thr Phe Tyr Ser Ala
            340                 345                 350

Ile Leu Ser Met Lys Leu Glu Ile Asn Ile Ile His Arg Ser Thr Val
        355                 360                 365

Ile Arg Gln Thr Leu Glu Glu Asp Gly Val Val Pro Thr Thr Ala Asp
    370                 375                 380

Ile Ile Tyr Lys Asp Glu Thr Ala Ser Glu Pro His Phe Leu Arg Ser
385                 390                 395                 400

Asn Val Ala Ile Ile Leu Gly Lys Ala Ser Val Ile Gly Leu Leu Leu
                405                 410                 415

Leu Ile Asn Leu Tyr Val Phe Thr Asp Lys Leu Asn Ala Thr Ile Leu
            420                 425                 430

Asn Thr Val Tyr Phe Asp Ser Thr Ile Tyr Ser Leu Pro Asn Phe Ile
        435                 440                 445

Asn Tyr Lys Asp Ile Gly Asn Leu Ser Asn Gln Val Ile Ile Ser Val
    450                 455                 460

Leu Pro Lys Gln Tyr Tyr Thr Pro Leu Lys Lys Tyr His Gln Ile Glu
465                 470                 475                 480

Asp Ser Val Leu Leu Ile Ile Asp Ser Val Ser Asn Ala Ile Arg Asp
                485                 490                 495

Gln Phe Ile Ser Lys Leu Leu Phe Phe Ala Phe Ala Val Ser Ile Ser
            500                 505                 510

Ile Asn Val Tyr Leu Leu Asn Ala Ala Lys Ile His Thr Gly Tyr Met
        515                 520                 525

Asn Phe Gln Pro Gln Ser Asn Lys Ile Asp Asp Leu Val Val Gln Gln
    530                 535                 540

Lys Ser Ala Thr Ile Glu Phe Ser Glu Thr Arg Ser Met Pro Ala Ser
545                 550                 555                 560

Ser Gly Leu Glu Thr Pro Val Thr Ala Lys Asp Ile Ile Ile Ser Glu
                565                 570                 575

Glu Ile Gln Asn Asn Glu Cys Val Tyr Ala Leu Ser Ser Gln Asp Glu
            580                 585                 590

Pro Ile Arg Pro Leu Ser Asn Leu Val Glu Leu Met Glu Lys Glu Gln
        595                 600                 605

Leu Lys Asn Met Asn Asn Thr Glu Val Ser Asn Leu Val Val Asn Gly
    610                 615                 620

Lys Leu Pro Leu Tyr Ser Leu Glu Lys Lys Leu Glu Asp Thr Thr Arg
625                 630                 635                 640

Ala Val Leu Val Arg Arg Lys Ala Leu Ser Thr Leu Ala Glu Ser Pro
                645                 650                 655

Ile Leu Val Ser Glu Lys Leu Pro Phe Arg Asn Tyr Asp Tyr Asp Arg
            660                 665                 670

Val Phe Gly Ala Cys Cys Glu Asn Val Ile Gly Tyr Met Pro Ile Pro
        675                 680                 685

Val Gly Val Ile Gly Pro Leu Ile Ile Asp Gly Thr Ser Tyr His Ile
```

-continued 690 695 700

Pro Met Ala Thr Thr Glu Gly Cys Leu Val Ala Ser Ala Met Arg Gly
705 710 715 720

Cys Lys Ala Ile Asn Ala Gly Gly Gly Ala Thr Thr Val Leu Thr Lys
725 730 735

Asp Gly Met Thr Arg Gly Pro Val Val Arg Phe Pro Thr Leu Ile Arg
740 745 750

Ser Gly Ala Cys Lys Ile Trp Leu Asp Ser Glu Glu Gly Gln Asn Ser
755 760 765

Ile Lys Lys Ala Phe Asn Ser Thr Ser Arg Phe Ala Arg Leu Gln His
770 775 780

Ile Gln Thr Cys Leu Ala Gly Asp Leu Leu Phe Met Arg Phe Arg Thr
785 790 795 800

Thr Thr Gly Asp Ala Met Gly Met Asn Met Ile Ser Lys Gly Val Glu
805 810 815

Tyr Ser Leu Lys Gln Met Val Glu Glu Tyr Gly Trp Glu Asp Met Glu
820 825 830

Val Val Ser Val Ser Gly Asn Tyr Cys Thr Asp Lys Lys Pro Ala Ala
835 840 845

Ile Asn Trp Ile Glu Gly Arg Gly Lys Ser Val Val Ala Glu Ala Thr
850 855 860

Ile Pro Gly Asp Val Val Lys Ser Val Leu Lys Ser Asp Val Ser Ala
865 870 875 880

Leu Val Glu Leu Asn Ile Ser Lys Asn Leu Val Gly Ser Ala Met Ala
885 890 895

Gly Ser Val Gly Gly Phe Asn Ala His Ala Ala Asn Leu Val Thr Ala
900 905 910

Leu Phe Leu Ala Leu Gly Gln Asp Pro Ala Gln Asn Val Glu Ser Ser
915 920 925

Asn Cys Ile Thr Leu Met Lys Glu Val Asp Gly Asp Leu Arg Ile Ser
930 935 940

Val Ser Met Pro Ser Ile Glu Val Gly Thr Ile Gly Gly Gly Thr Val
945 950 955 960

Leu Glu Pro Gln Gly Ala Met Leu Asp Leu Leu Gly Val Arg Gly Pro
965 970 975

His Pro Thr Glu Pro Gly Ala Asn Ala Arg Gln Leu Ala Arg Ile Ile
980 985 990

Ala Cys Ala Val Leu Ala Gly Glu Leu Ser Leu Cys Ser Ala Leu Ala
995 1000 1005

Ala Gly His Leu Val Gln Ser His Met Thr His Asn Arg Lys Thr Asn
1010 1015 1020

Lys Ala Asn Glu Leu Pro Gln Pro Ser Asn Lys Gly Pro Pro Cys Lys
1025 1030 1035 1040

Thr Ser Ala Leu Leu
1045

( 2 ) INFORMATION FOR SEQ ID NO:7:

( i ) SEQUENCE CHARACTERISTICS:

( A ) LENGTH: 22 base pairs ( B ) TYPE: nucleic acid ( C ) STRANDEDNESS: single ( D ) TOPOLOGY: linear ( i i ) MOLECULE TYPE: DNA (genomic)

( x i ) SEQUENCE DESCRIPTION: SEQ ID NO:7:

GATCCGTCGA CGCATGCCTG CA 22

( 2 ) INFORMATION FOR SEQ ID NO:8:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

GGCATGCGTC GACG 14

( 2 ) INFORMATION FOR SEQ ID NO:9:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CCGGATCCGG 10

( 2 ) INFORMATION FOR SEQ ID NO:10:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

AGCTTTCGCG AGCTCGAGAT CTAGATATCG ATG 33

( 2 ) INFORMATION FOR SEQ ID NO:11:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

AATTCATCGA TATCTAGATC TCGAGCTCGC GA 32

( 2 ) INFORMATION FOR SEQ ID NO:12:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

TATCGAATTC AAGCTTGGTA CCGA 24

-continued ( 2 ) INFORMATION FOR SEQ ID NO:13:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

TATCGGTACC AAGCTTGAAT TCGA 24

( 2 ) INFORMATION FOR SEQ ID NO:14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

GATCCAGCTG TGTAC 15

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

CCCGGGATCG ATCACGT 17

( 2 ) INFORMATION FOR SEQ ID NO:16:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GATCGATCCC GGGACGT 17

( 2 ) INFORMATION FOR SEQ ID NO:17:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

ATAAAGACAT TGTTTTTAGA TCTGTTGTAA 30

( 2 ) INFORMATION FOR SEQ ID NO:18:

( i ) SEQUENCE CHARACTERISTICS:

-continued ( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

GATTTATCTT CGTTTCCTGC AAGTTTTTGT TC 32

( 2 ) INFORMATION FOR SEQ ID NO:19:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

AGCTTCGAAG AACGAAGGAA GGAGCACAGA CTTAG 35

( 2 ) INFORMATION FOR SEQ ID NO:20:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

ATTGGTATAT ATACGCATAT TGCGGCCGCG GTAC 34

( 2 ) INFORMATION FOR SEQ ID NO:21:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CGCGGCCGCA ATATGCGTAT ATATAC 26

( 2 ) INFORMATION FOR SEQ ID NO:22:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

CAATCTAAGT CTGTGCTCCT TCCTTCGTTC TTCGA 35

( 2 ) INFORMATION FOR SEQ ID NO:23:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear -continued ( i i ) MOLECULE TYPE: DNA (genomic)

( x i ) SEQUENCE DESCRIPTION: SEQ ID NO:23:

CTTTATGAGG GTAACATGAA TTCAAGAAGG 30

( 2 ) INFORMATION FOR SEQ ID NO:24:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

GCCAAGTAGT TTTTACTCTT CAAGACAGAT AATTTGCTGA CA 42